United States Patent
Xiang et al.

(10) Patent No.: US 11,420,955 B2
(45) Date of Patent: *Aug. 23, 2022

(54) COMPOUNDS AS NEURONAL HISTAMINE RECEPTOR-3 ANTAGONISTS AND USES THEREOF

(71) Applicant: XWPHARMA LTD., Grand Cayman (KY)

(72) Inventors: Jia-Ning Xiang, Wuhan (CN); Xuesong Xu, Wuhan (CN); Yi Feng, Wuhan (CN); Wai-Si Eng, Maple Glen, PA (US)

(73) Assignee: XWPHARMA LTD., Grand Cayman (KY)

(*) Notice: Subject to any disclaimer, the term of this patent is extended or adjusted under 35 U.S.C. 154(b) by 0 days.

This patent is subject to a terminal disclaimer.

(21) Appl. No.: 17/193,678

(22) Filed: Mar. 5, 2021

(65) Prior Publication Data

US 2021/0188808 A1 Jun. 24, 2021

Related U.S. Application Data

(60) Continuation of application No. 16/909,779, filed on Jun. 23, 2020, now Pat. No. 10,968,202, which is a continuation of application No. 16/793,139, filed on Feb. 18, 2020, now Pat. No. 10,730,853, which is a division of application No. 16/587,344, filed on Sep. 30, 2019, now Pat. No. 10,618,886, which is a continuation of application No. PCT/CN2018/109115, filed on Sep. 30, 2018.

(51) Int. Cl.
*A61K 31/517* (2006.01)
*C07D 401/12* (2006.01)

(52) U.S. Cl.
CPC .................. *C07D 401/12* (2013.01)

(58) Field of Classification Search
CPC ......... A61K 31/517; A61P 25/00; A61P 25/28
USPC ...................................... 514/266.2
See application file for complete search history.

(56) References Cited

U.S. PATENT DOCUMENTS

| | | | |
|---|---|---|---|
| 4,370,338 A | 1/1983 | Mizoule et al. | |
| 6,489,350 B1 | 12/2002 | Benedyk et al. | |
| 7,482,429 B2 | 1/2009 | Albericio et al. | |
| 7,521,455 B2 | 4/2009 | Nagase et al. | |
| 7,960,561 B2 | 6/2011 | Sorensen et al. | |
| 8,802,673 B2 | 8/2014 | Galley et al. | |
| 9,309,182 B2 | 4/2016 | Tung et al. | |
| 10,457,627 B2 | 10/2019 | Xiang et al. | |
| 10,501,401 B2 | 12/2019 | Xiang et al. | |
| 10,730,853 B2* | 8/2020 | Xiang .................. | C07D 403/12 |
| 10,968,202 B2* | 4/2021 | Xiang .................. | C07D 403/12 |
| 2005/0182045 A1 | 8/2005 | Nagase et al. | |
| 2006/0210630 A1 | 9/2006 | Liang et al. | |
| 2010/0144869 A1 | 6/2010 | Nudelman et al. | |
| 2012/0283300 A1 | 11/2012 | Kim et al. | |
| 2016/0052862 A1 | 2/2016 | Frost et al. | |
| 2019/0047966 A1 | 2/2019 | Arai et al. | |

FOREIGN PATENT DOCUMENTS

| | | |
|---|---|---|
| CN | 1422278 | 6/2003 |
| CN | 101511388 | 9/2006 |
| CN | 102076342 | 5/2011 |
| CN | 102834098 | 12/2012 |
| CN | 103370289 | 10/2013 |
| CN | 103443074 | 12/2013 |
| CN | 108602780 | 9/2018 |
| DE | 852392 | 10/1952 |
| FR | 2662695 | 12/1991 |
| JP | 2002513394 | 5/2002 |
| JP | 2004059452 | 2/2004 |
| RU | 2142800 | 12/1999 |
| WO | 99/41275 | 8/1999 |
| WO | 99/51613 | 10/1999 |
| WO | 2005/077905 | 8/2005 |
| WO | 2005/115993 | 12/2005 |
| WO | 2005/123731 | 12/2005 |
| WO | 2006/085692 | 8/2006 |
| WO | 2009/040331 | 4/2009 |

(Continued)

OTHER PUBLICATIONS

Search Report for European Application No. 18934682.8, dated Aug. 11, 2021, 8 pages.
Sowaileh et al., "Application of the Pentafluorosulfanyl Group as a Bioisosteric Replacement", ChemMedChem Communications, Sep. 2017, vol. 12, No. 18, pp. 1481-1490.
Hudkins, R. et al., "4-Phenoxypiperidine pyridazin-3-one histamine H3 receptor inverse agonists demonstrating potent and robust wake promoting activity", Bioorganic & Medicinal Chemistry Letters, 2012, vol. 22, pp. 1504-159.
Nagase, T. et al., Synthesis, Structure—Activity Relationships, and Biological Profiles of a Quinazolinone Class of Histamine H3 Receptor Inverse Agonists, Journal of Medicinal Chemistry, 2008, VI. 51, pp. 4780-4789.

(Continued)

*Primary Examiner* — Charanjit Aulakh

(57) ABSTRACT

The present invention relates compounds of Formula (A) as H3R antagonists, as well as their preparation and uses, and further relates pharmaceutical compositions comprising these compounds and their uses as modulators of Histamine 3 Receptor (H3R) functions. The present invention also relates to the uses of the compounds or pharmaceutical compositions in treating or preventing certain disorders and diseases which relate to H3R functions in humans.

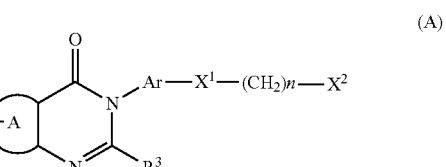

(A)

14 Claims, 4 Drawing Sheets

(56) References Cited

FOREIGN PATENT DOCUMENTS

| WO | 2009/102462 | 8/2009 |
| WO | 2009/137717 | 11/2009 |
| WO | 2010/124046 | 10/2010 |
| WO | 2013/019561 | 2/2013 |
| WO | 2013/163244 | 10/2013 |
| WO | 2014/031840 | 2/2014 |
| WO | 2014/152263 | 9/2014 |
| WO | 2014/205393 | 12/2014 |
| WO | 2015/057884 | 4/2015 |
| WO | 2015/083129 | 6/2015 |
| WO | 2018/098472 | 5/2018 |

OTHER PUBLICATIONS

Sirci, F. et al., "Virtual Fragment Screening: Discovery of Histamine H3 receptor Ligands Using Ligand-Based and Protein-Based Molecular Fingerprints", Journal of Chemical Information and Modeling, 2012, vol. 52, pp. 3308-3324.
International Search Report and Written Opinion for International Application No. PCT/CN2018/090151, dated Feb. 20, 2019, 14 pages.
International Search Report and Written Opinion for International Application No. PCT/CN2018/097241, dated Apr. 28, 2019, 11 pages.
International Search Report and Written Opinion for International Application No. PCT/CN2018/118565, dated Jul. 8, 2019, dated Apr. 28, 2019, 13 pages.
International Search Report and Written Opinion for International Application No. PCT/CN2016/099763, dated Jan. 3, 2017, 15 pages.
International Search Report and Written Opinion for International Application No. PCT/CN2017/078873, dated Jan. 9, 2018, 12 pages.
International Search Report and Written Opinion for International Application No. PCT/CN2018/109115, dated Jul. 8, 2019, 11 pages.
Non-Final Office Action for U.S. Appl. No. 16/587,571, dated Nov. 19, 2019, 23 pages.
Non-Final Office Action for U.S. Appl. No. 16/831,086, dated Apr. 13, 2020, 8 pages.
Non-Final Office Action for U.S. Appl. No. 16/791,243, dated Apr. 8, 2020, 20 pages.
Search Report for Australia Application No. 2017406159, dated Feb. 28, 2020, 6 pages.
Search Report for Australia Application No. 2016328150, dated Mar. 27, 2020, 4 pages.
Search Report for Russia Application No. 2019134607, dated Feb. 11, 2020, 7 pages.
Ahn et al., "Hapten and Antibody Production for a Sensitive immunoassay Determining a Human Urinary Metabolite of the Pyrethroid Insecticide Permethrin," J. Agriculture Food Chemistry, Jun. 2004, vol. 52, No. 15, p. 4583-4594.
Arnulf, Isabelle. "Excessive daytime sleepiness in parkinsonism", Sleep Medicine Reviews, 2005, vol. 9, p. 185-200.
Arnulf, Isabelle. "Results of clinical trials of tripolisant in narcolepsy and Parkinson's disease", Eur Neuropsychopharmacol 19: S204, 2009, DOI: 10.1016/S0924-977X(09)/70268-8.
Dauvilliers, Y. et al., "Pitolisant for Daytime Sleepiness in Patients with Obstructive Sleep Apnea Who Refuse Continuous Positive Airway Pressure Treatment—A Randomized Trial", American Journal of Respiratory and Critical Care Medicine, May 2020, vol. 201, No. 9, p. 1136-1145.
Harwell, V. et al., "Pitolisant and Other Histamine-3 Receptor Antagonists—An Update on Therapeutic Potentials and Clinical Prospects", Medicines, 2020, vol. 7, No. 55, 16 pages.
Jiang, et al., Copper-Catalyzed Aerobic Oxidative Regioselective Thiocyanation of Aromatics and Heteroaromatics. J. Org. Chem. 2017, 82, 18, 9312-9320.
Jimonet et al., "Riluzole series. Synthesis and in vivo "antiglutamate" activity of 6-substituted-2-benzothiazolamines and 3-substituted-2-imino-benzothiazolines", Journal of Medical Chemistry, 1999, vol. 42, p. 2828-2843.
Jordan, et al., Efficient Conversion of Substituted Aryl Thioureas to 2-Aminobenzothiazoles Using Benzyltrimethylammonium Tribromide. J. Org. Chem. 2003, 68, 22, 8693-8696.
Kaname et al., "One-pot copper-catalyzed tandem addition-cyclization of 2-iodoanilines with isoselenocyanates for the practical preparation of 2-aminobenzoselenazoles," Tetrahedron Letters, Nov. 2010, vol. 52, p. 505-508.
Lee et al., "Development of an Immunoassay for the Residues of the Herbicide Bensulfuron-Methyl," Journal of Agricultural and Food Chemistry, Mar. 2002, vol. 50, No. 7, p. 1791-1803.
McGeer et al., "Pharmacologic Approaches to the Treatment of Amyotrophic Lateral Sclerosis", Drug Mechanisms and Targets, 2006, vol. 19, No. 1, p. 31-37.
Passani et al., "The histamine H3 receptor as a novel therapeutic target for cognitive and sleep disorders", Trends in Pharmacological Sciences, Dec. 2004, vol. 25, No. 12, p. 618-625.
Patani et al., "Bioisosterism: A Rational Approach in Drug Design", Chemical Reviews, 1996, vol. 96, p. 3147-3176.
Rothweiler, et al., Probing the ATP-Binding Pocket of Protein Kinase DYRK1A with Benzothiazole Fragment Molecules. J. Med. Chem. 2016, 59, 21, 9814-9824.
Rynearson et al., "2-Aminobenzoxazole ligands of the hepatitis C virus internal ribosome entry site," Bioorganic & Medicinal Chemistry Letters, Jun. 2014, vol. 24, p. 3521-3525.
Sankaranarayanan et al., "Naphtho[1,2-d]thiazol-2-ylamine (SKA-31), a new activator of KCa2 and KCa3.1 potassium channels, potentiates the endothelium-derived hyperpolarizing factor response and lowers blood pressure", Molecular Pharmacology, 2009, vol. 75, p. 281-295.
Schwartz, Jean-Charles. "The histamine H3 receptor: from discovery to clinical trials with pitolisant", British Journal of Pharmacology, 2011, vol. 163, p. 713-721.
Singh, J.K. et al., "Development of time-resolved fluorescent based [Eu]-GTP binding assay for selection of human Histamine 3 receptor antagonists/inverse agonist: a potential target for Alzheimer's treatment", Annals of Neurosciences, Apr. 2012, vol. 19, No. 2, p. 71-75.
Staldweiser et al., "Combinatorial Solid-Phase Synthesis of Structurally Complex Thiazolylhydantoines," Agnew Chern Int. Ed., Dec. 1998, col. 37, No. 10, p. 1402-1404.
Szakacs, Z. et al., "Safety and efficacy of pitolisant on cataplexy in patients with narcolepsy: a randomised, double-blind, placebo-controlled trial", Lancet Neurology, 2017, vol. 16, p. 200-207.
Ward et al., "Discovery of an Orally Bioavailable Nki Receptor Antagonist, (2S, 3S)-(2-Methoxy-5-tetrazol-1-ylbenzyl)(2-phenylpiperidin-3-yl)amine (GR203040), with Potent Antiemetic Activity," Journal of Med. Chem., 1995, vol. 38, p. 4985-4992.
Chemical Abstracts Registry No. 1744-22-5, indexed in the Registry file Nov. 16, 1984.
Chemical Abstracts Registry No. 1243631-58-4, indexed in the Registry file Sep. 29, 2010.
Chemical Abstracts Registry No. 60388-38-7, indexed in the Registry file Nov. 16, 1984.
Chemical Abstracts Registry No. 60176-62-7, indexed in the Registry file Nov. 16, 1984.
Chemical Abstracts Registry No. 326-45-4, indexed in the Registry file Nov. 16, 1984.
Chemical Abstracts Registry No. 142229-71-8, indexed in the Registry file Jul. 3, 1992.
STN Columbus, Registry Jul. 21, 1990, 81055-72-3, 128321-03-9.
STN Columbus, Registry Dec. 4, 2015, CAS No. 1822708-15-5.
RN 1211588-05-4, STN REG, Mar. 19, 2010.
RN 1354448-66-0, STN REG, Jan. 25, 2012.
RN 1206250-52-3, STN REG, Feb. 12, 2010.
RN 1206250-51-2, STN REG, Feb. 12, 2010.
RN 1206250-54-5, STN REG, Feb. 12, 2010.
RN 1206248-58-9, STN REG, Feb. 12, 2010.
RN 747353-65-6, STN REG, Sep. 17, 2004.
RN 60176-63-8, STN REG, Nov. 16, 1984.

* cited by examiner

COMPOUNDS AS NEURONAL HISTAMINE RECEPTOR-3 ANTAGONISTS AND USES THEREOF

This application is a continuation of U.S. application Ser. No. 16/909,779, filed on Jun. 23, 2020, now allowed, which is a continuation of U.S. application Ser. No. 16/793,139, filed on Feb. 18, 2020, which issued as U.S. Pat. No. 10,730,853, which is a divisional of U.S. application Ser. No. 16/587,344, which issued as U.S. Pat. No. 10,618,886, which is a continuation under 35 U.S.C. § 111(a) of PCT International Application No. PCT/CN2018/109115 filed on Sep. 30, 2018, which is incorporated by reference in its entirety.

FIELD

The present invention relates to the field of medicinal technology, in particular, to certain compounds, their preparation and uses, as well as pharmaceutical compositions comprising such compounds. As exemplified, the present invention relates to certain compounds, their preparation, and the corresponding pharmaceutical compositions that can be potentially used in the manufacture of a medicament for preventing, treating, ameliorating certain disorder or a disease in a patient, which includes, CNS disorders or narcolepsy. It is believed that the compounds and/or pharmaceutical compositions of the present invention exert their therapeutic benefits by, among other things, acting to modulate (e.g., antagonizing) neuronal histamine receptor-3 (H3R).

BACKGROUND

Binding of postsynaptic histamine onto its H3R limits fluxes of not only histamine but also a variety of other important neurotransmitters, e.g., acetylcholine, dopamine, glutamate, noradrenaline, serotonin, GABA, etc. (e.g., T. A. Esbenshade, et. al, *Mol. Intervention*, v. 6, pp. 77-88 2006). In contrast, H3R antagonists (also known as inverse agonists) could increase these neural transmitting fluxes for treating diverse groups of CNS disorders (e.g. cognitive, psychiatric, neuro-motor, pain, etc). (http://molphann.aspetjournals.org/content/molphann/90/5/649.full.pdf, accessed Feb. 26, 2017; a review of recent patent application on H3R antagonist, D. Lazewska et. al., *Expert Opin. Therapeutic Patents*, v. 28, pp. 175-196 2018 and references cited therein).

Ongoing clinical trials of H3R antagonists to treat narcolepsy over the past decade (e.g. review-https://www.ncbi.nlm.nih.gov/pmc/articles/PMC5344488/pdf/nss-9-039.pdf accessed Feb. 26, 2018) led to EU sales approval of the 1$^{st}$ H3R antagonist-pitolisant (brand name=Wakix; http://www.ema.europa.eu/ema/index.jsp?curl=pages/medicines/human/medicines/002616/human_med_001955.jsp&mid=WC0b01ac058001d124, accessed Feb. 26, 2018). While Wakix and sodium oxybate (brand name-Xyrem; its EU sales approval: http://www.ema.europa.eu/ema/index.jsp?curl=pages/medicines/human/medicines/000593/human_med_001163.jsp&mid=WC0b01ac058001d124, accessed Feb. 26, 2018) are the current drugs sold to specifically treat narcolepsy and cataplexy (afflicts ~70% of the narcoleptic patients), significant fractions (~20-40%) of initially titrated patients discontinue further drug dosing due to poor efficacy and/or toxicity (respectively https://www.ncbi.nlm.nih.gov/pmc/articles/PMC5414617/pdf/nss-9-127.pdf and https://www.ncbi.nlm.nih.gov/pmc/articles/PMC5727622/pdf/main.pdf both accessed on Feb. 26, 2018). Thus, and like patients affected by some other CNS disorders, narcoleptic patients urgently need for better drugs in order to significantly lower these fractions.

The compounds and pharmaceutical formulations disclosed in the present application are believed to exert their therapeutic benefits by, among other things, acting to antagonize H3R.

SUMMARY

The following is only an overview of some aspects of the present invention, but is not limited thereto. All references of this specification are incorporated herein by reference in their entirety. When the disclosure of this specification is different with citations, the disclosure of this specification shall prevail. The present invention provides compounds and pharmaceutical compositions, which modulate antagonize H3R, their preparation, and the corresponding pharmaceutical compositions. The compounds and/or pharmaceutical compositions of the present invention can be potentially used in the manufacture of a medicament for preventing, treating, ameliorating certain disorder or a disease related to H3R in a patient, which includes, CNS disorders or narcolepsy.

Specifically, in one aspect, the present invention relates to a compound having Formula (A) or pharmaceutically acceptable salt thereof,

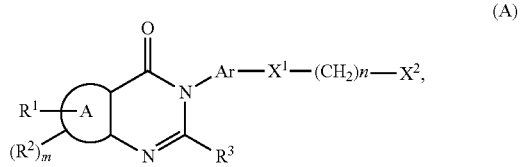

(A)

wherein,
R$^1$ and R$^2$ is independently H or SF$_5$, with the provision of one of R$^1$ and R$^2$ is SF$_5$ at least;
R$^3$ is C$_{1-6}$ alkyl or C$_{3-6}$ cycloalkyl;
Ring A is a C$_{6-8}$ aryl;
Ar is C$_{5-6}$ aryl, wherein the C$_{5-6}$ aryl is optionally substituted with 1, 2, 3 or 4 R$^e$;
R$^e$ is H, halogen, CN, NO$_2$, OH, C$_{1-6}$ alkoxy or C$_{1-6}$ alkyl;
X is S or O;
X$^2$ is

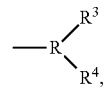

wherein R is N or C;
R$^3$ and R$^4$ is C$_{1-6}$ alkyl, or R$^3$ and R$^4$ together with R to which they are attached, form a C$_{3-7}$ carbocyclic ring, 3- to 7-membered heterocyclic ring, and wherein each of the C$_{3-7}$ carbocyclic ring, 3- to 7-membered heterocyclic ring is independently optionally substituted with 1, 2, 3, 4, 5 or 6 R$^f$;
R$^f$ is C$_{1-6}$ alkyl, C$_{3-6}$ cycloalkyl, —C(=O)R$^a$, and wherein each of the C$_{1-6}$ alkyl, C$_{3-6}$ cycloalkyl, —C(=O)R$^a$ is independently optionally substituted with C$_{1-6}$ alkyl;

$R^a$ is $C_{1-6}$ alkyl, $C_{3-6}$ cycloalkyl or 3- to 7-membered heterocyclic ring;

m is an integer from 0 to 3;

n is an integer from 0 to 5.

In one embodiment, $R^3$ is $C_{1-4}$ alkyl or $C_{3-6}$ cycloalkyl

In one embodiment, A is phenyl.

In one embodiment, Ar is phenyl, wherein the phenyl is optionally substituted with 1, 2, 3 or 4 $R^e$.

In one embodiment, Ar is the following sub-formula:

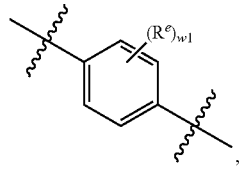

(W-1a)

wherein w1 is 0, 1, 2, 3 or 4.

In one embodiment, $R^e$ is H, F, Cl, Br, I, CN, $NO_2$, OH, methyl, ethyl, i-propyl, n-propyl, n-butyl, t-butyl, methoxy, ethoxy.

In one embodiment, $R^3$ and $R^4$ is $C_{1-4}$ alkyl.

In one embodiment, R is N, $R^3$ and $R^4$ together with the nitrogen atom to which they are attached, form a 3- to 7-membered heterocyclic ring, and wherein the 3- to 7-membered heterocyclic ring is independently optionally substituted with 1, 2, 3, 4 or 5 $R^f$.

In one embodiment, R is C, $R^3$ and $R^4$ together with the carbon atom to which they are attached, form a $C_{3-7}$ carbocyclic ring, 3- to 7-membered heterocyclic ring, and wherein each of the $C_{3-7}$ carbocyclic ring, 3- to 7-membered heterocyclic ring is independently optionally substituted with 1, 2, 3, 4 or 5 $R^f$.

In one embodiment, $R^f$ is $C_{1-4}$ alkyl, $C_{3-6}$ cycloalkyl, —C(=O)$R^a$.

In one embodiment, $R^f$ is —C(=O)$R^a$, methyl, ethyl, i-propyl,

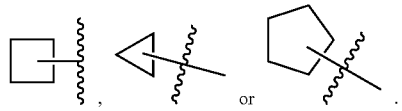

In one embodiment, $R^a$ is methyl, ethyl,

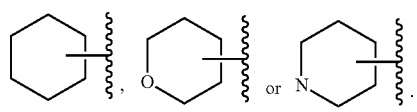

In one embodiment, $X^2$ is one of the following sub-formulae:

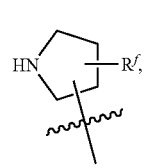

(X-1a)

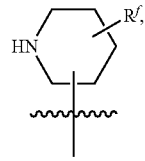

(X-2a)

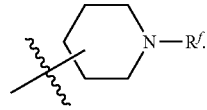

(X-3a)

In one embodiment, $X^2$ is one of the following sub-formulae:

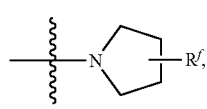

(X-1b)

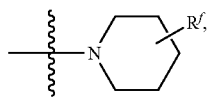

(X-2b)

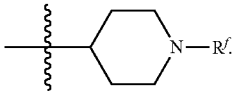

(X-3b)

In one embodiment, provided herein is a compound having the Formula (B),

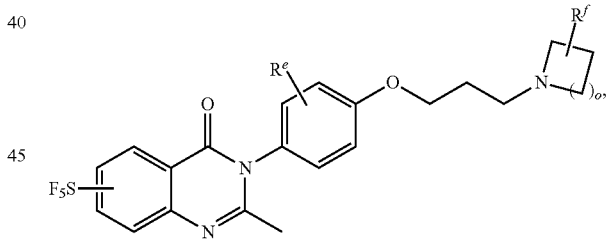

(B)

wherein o is an integer from 0 to 4; and $R^e$, $R^f$ are as defined herein.

In one embodiment, provided herein is a compound having the Formula (C),

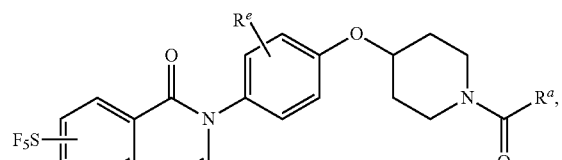

(C)

where $R^e$, $R^a$ are as defined herein.

In one embodiment, provided herein is a compound having the Formula (D),

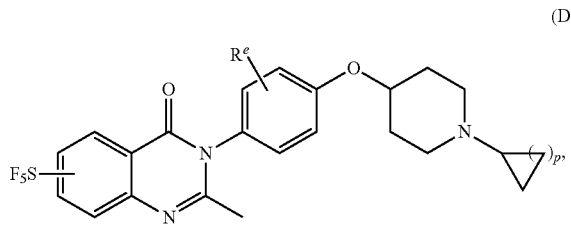

wherein p is an integer from 1 to 5; and
R$^e$ is as defined herein.

In another aspect, provided herein is a pharmaceutical composition comprising the compound of the present invention.

In one embodiment, the pharmaceutical composition further comprising a pharmaceutically acceptable carrier, adjuvant, vehicle or a combination thereof.

In one embodiment, the pharmaceutical composition further comprising one or more other therapeutic agents, and wherein the other therapeutic agent is used in treating CNS disorders or narcolepsy.

In one embodiment, the CNS disorders is cognitive, psychiatric, neuro-motor or pain.

In one embodiment, the other therapeutic agent is further comprising: an active ingredient selected from the group consisting of dopamine receptor antagonists, serotonin-norepinephrine reuptake inhibitors, selective serotonin reuptake inhibitors, noradrenergic reuptake inhibitors, non-selective serotonin re-uptake inhibitors, and acetylcholinesterase inhibitors.

In another aspect, provided herein is use of the compound or the pharmaceutical composition in the manufacture of a medicament for preventing, managing, treating or lessening CNS disorders or narcolepsy in a patient.

In another aspect, provided herein is use of the compound or the pharmaceutical composition in the manufacture of a medicament for antagonizing H3 receptor.

In another aspect, provided herein is the compound or the pharmaceutical composition for use in preventing, managing, treating or lessening CNS disorders or narcolepsy caused by a virus infection in a patient.

In another aspect, provided herein is the compound or the pharmaceutical composition for use in antagonizing H3 receptor.

In another aspect, provided herein is a method of preventing, managing, treating or lessening CNS disorders or narcolepsy in a patient, comprising administering to the patient in need thereof a therapeutically effective amount of the compound or the pharmaceutical composition.

In another aspect, provided herein is a method of antagonizing H3 receptor in a patient, comprising administering to the patient in need thereof a therapeutically effective amount of the compound or the pharmaceutical composition.

In yet another aspect, the present invention is directed to methods of making compounds of Formula (A) (D) and pharmaceutically acceptable salts thereof.

In certain embodiments of the compounds, pharmaceutical compositions, and methods of the invention, the compound of Formula (A) (D) is a compound selected from those species described or exemplified in the detailed description below, or is a pharmaceutically acceptable salt of such a compound.

Another preferred embodiment, the present invention is directed to methods of preparing pharmaceutical compositions each comprising an effective amount of at least one compound of Formula (A) (D) or a pharmaceutically acceptable salt of a compound of Formula (A) (D). Pharmaceutical compositions according to the invention may further comprise at least one pharmaceutically acceptable excipient, carrier, adjuvant, solvent, support or a combination thereof.

If formulated as a fixed dose, such combination products employ the compounds of this invention within the dosage range described herein (or as known to those skilled in the art) and the other pharmaceutically active agents or treatments within its dosage range. The compounds of the invention may also be administered sequentially with known anti-CNS disorders or narcolepsy agents when a combination formulation is inappropriate. In any combination treatment, the invention is not limited in the sequence of administration; compounds of Formula (A) (D) may be administered either prior to or after administration of the known anti-CNS disorders or narcolepsy agent. Such techniques are within the skills of persons skilled in the art as well as attending physicians.

Yet another embodiment is a method for administering a compound of the instant invention to a subject (e.g., a human) in need thereof by administering to the subject the pharmaceutical formulation of the present invention.

Yet another embodiment is a method of preparing a pharmaceutical formulation of the present invention by mixing at least one pharmaceutically acceptable compound of the present invention, and, optionally, one or more pharmaceutically acceptable additives or excipients.

For preparing pharmaceutical compositions from the compounds described by this invention, inert, pharmaceutically acceptable carriers can be either solid or liquid. Solid form preparations include powders, tablets, dispersible granules, capsules, beads, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18$^{th}$ Edition, (1990), Mack Publishing Co., Easton, Pa.

Liquid form preparations include solutions, suspensions and emulsions. For example, there are water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g., nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally or intravenously.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 1000 mg, preferably from about 1 mg to about 500 mg, more preferably from about 1 mg to about 300 mg, still more preferably from about 1 mg to about 200 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required. The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 10 mg/day to 200 mg/day, in one to two divided doses.

Any embodiment disclosed herein can be combined with other embodiments as long as they are not contradictory to one another, even though the embodiments are described under different aspects of the invention. In addition, any technical feature in one embodiment can be applied to the corresponding technical feature in other embodiments as long as they are not contradictory to one another, even though the embodiments are described under different aspects of the invention.

The foregoing merely summarizes certain aspects disclosed herein and is not intended to be limiting in nature. These aspects and other aspects and embodiments are described more fully below.

BRIEF DESCRIPTION OF THE DRAWINGS

These and other aspects and advantages of embodiments of the present disclosure will become apparent and more readily appreciated from the following descriptions made with reference the accompanying schemes and drawings, in which.

DETAILED DESCRIPTION

Figure 1B:
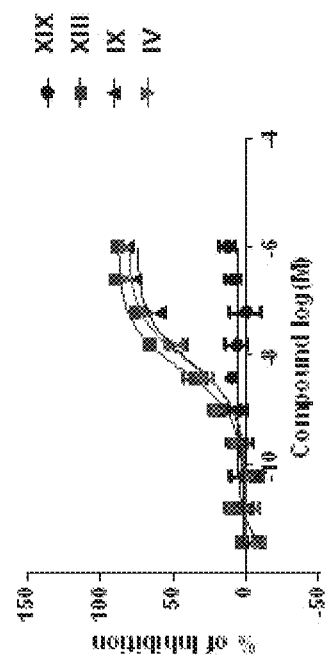
FIG. 1A and FIG. 1B show histamine H3 GTPγS binding curves and % inhibition curves in the inverse agonist mode for Compounds (IV), (XIII), (IX), and (XIX), respectively.

For the sake of brevity, the disclosures of the publications cited in this specification, including patents and patent applications, are herein incorporated by reference in their entirety.

Most chemical names were generated using IUPAC nomenclature herein. Some chemical names were generated using different nomenclatures or alternative or commercial names known in the art. In the case of conflict between names and structures, the structures prevail.

Reference will now be made in detail to certain embodiments of the invention, examples of which are illustrated in the accompanying structures and formulas. The invention is intended to cover all alternatives, modifications and equivalents which may be included within the scope of the present invention as defined by the claims. One skilled in the art will recognize many methods and materials similar or equivalent to those described herein, which could be used in the practice of the present invention. The present invention is in no way limited to the methods and materials described herein. In the event that one or more of the incorporated literatures, patents, and similar materials differs from or contradicts this application, including but not limited to defined terms, term usage, described techniques, or the like, this application controls.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable sub-combination.

Unless defined otherwise, all technical and scientific terms used herein have the same meaning as are commonly understood by one skilled in the art to which this invention belongs. All patents and publications referred to herein are incorporated by reference in their entirety.

As used herein, the following definitions shall apply unless otherwise indicated. For purposes of this invention, the chemical elements are identified in accordance with the Periodic Table of the Elements, CAS version, and the Handbook of Chemistry and Physics, 75th Ed. 1994. Additionally, general principles of organic chemistry are described in "Organic Chemistry", Thomas Sorrell, University Science Books, Sausalito: 1999, and "March's Advanced Organic Chemistry" by Michael B. Smith and Jerry March, John Wiley & Sons, New York: 2007, the entire contents of which are hereby incorporated by reference.

As used above, and throughout this disclosure, the following terms, unless otherwise indicated, shall be understood to have the following meanings. If a definition is missing, the conventional definition as known to one skilled in the art controls. If a definition provided herein conflicts or is different from a definition provided in any cited publication, the definition provided herein controls.

As used herein, the terms "including", "containing", and "comprising" are used in their open, non-limiting sense.

As used herein, the singular forms "a", "an", and "the" include plural referents unless the context clearly dictates otherwise.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

As used herein, "alkyl" refers to a saturated, straight- or branched-chain hydrocarbon group having from 1 to 12 carbon atoms. Representative alkyl groups include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, n-pentyl, isopentyl, neopentyl, n-hexyl, and the like, and longer alkyl groups, such as heptyl, octyl, and the like.

At various places in the present specification, substituents of compounds disclosed herein are disclosed in groups or in ranges. It is specifically intended that the invention include each and every individual sub-combination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

The term "halogen" or "halo" are used interchangeably in this invention, and refers to Fluoro (F), Chloro (Cl), Bromo (Br), or Iodo (I).

The term "alkoxy" refers to an alkyl group, as previously defined, attached to the parent molecular moiety via an oxygen atom. Unless otherwise specified, the alkoxy group contains 1-12 carbon atoms. In one embodiment, the alkoxy group contains 1-6 carbon atoms. In other embodiment, the alkoxy group contains 1-4 carbon atoms. In still other embodiment, the alkoxy group contains 1-3 carbon atoms. The alkoxy group may be optionally substituted with one or more substituents disclosed herein. As used herein, "alkoxy-alkyl" means -(alkylenyl)-O-(alkyl), wherein each "alkyl" is independently an alkyl group defined above.

"Aryl" means a mono-, bi-, or tricyclic aromatic group, wherein all rings of the group are aromatic. For bi- or tricyclic systems, the individual aromatic rings are fused to one another. Exemplary aryl groups include, but are not limited to, phenyl, naphthalene, and anthracene.

The term "cyanoalkyl" denotes an alkyl group as defined above wherein a hydrogen atom of the alkyl group is replaced by a cyano (—CN) group. The alkyl portion of the cyanoalkyl group provides the connection point to the remainder of the molecule.

The term "deuterium" as used herein means a stable isotope of hydrogen having one proton and one neutron.

The terms "carbocyclyl" and "carbocycle" as used interchangeably herein, refer to a monovalent or multivalent ring having 3 to 12 carbon atoms as a monocyclic, bicyclic or tricyclic ring system, which is saturated or contains one or more degrees of unsaturation, but an aromatic ring can not exist in the carbocyclyl group.

The term "hydroxy" means an —OH group.

The terms "heterocyclyl" and "heterocycle" as used interchangeably herein refer to a monovalent or multivalent monocyclic, bicyclic or tricyclic ring containing 3-12 carbon atoms, wherein each one or more atoms in the ring is independently replaced with heteroatom, the heteroatom is as defined herein, and the ring may be saturated or contains one or more degrees of unsaturations, but an aromatic ring can not exist in the aromatic ring.

The term "cycloalkyl" refers to a monovalent or multivalent saturated ring having 3 to 12 ring carbon atoms as a monocyclic, bicyclic, or tricyclic ring system.

Those skilled in the art will recognize that the species of heteroaryl, and cycloalkyl groups listed or illustrated above are not exhaustive, and that additional species within the scope of these defined terms may also be selected.

As described herein, compounds disclosed herein may optionally be substituted with one or more substituents, or as exemplified by particular classes, subclasses, and species of the invention.

As used herein, the term "substituted" means that the specified group or moiety bears one or more suitable substituents. As used herein, the term "unsubstituted" means that the specified group bears no substituents. As used herein, the term "optionally substituted" means that the specified group is unsubstituted or substituted by the specified number of substituents. Where the term "substituted" is used to describe a structural system, the substitution is meant to occur at any valency-allowed position on the system.

As used herein, the expression "one or more substituents" denotes one to maximum possible number of substitution(s) that can occur at any valency-allowed position on the system. In a certain embodiment, one or more substituent means 1, 2, 3, 4, or 5 substituents. In another embodiment, one or more substituent means 1, 2, or 3 substituents.

Any atom that is represented herein with an unsatisfied valence is assumed to have the sufficient number of hydrogen atoms to satisfy the atom's valence.

When any variable (e.g., alkyl, alkylenyl, heteroaryl, $R^1$, $R^2$, or $R^a$) appears in more than one place in any formula or description provided herein, the definition of that variable on each occurrence is independent of its definition at every other occurrence.

Numerical ranges, as used herein, are intended to include sequential whole numbers. For example, a range expressed as "from 0 to 4" or "0-4" includes 0, 1, 2, 3 and 4, while a range expressed as "10-20%" includes 10%, 11%, 12%, 13%, 14%, 15%, 16%, 17%, 18%, 19% and 20%. Similarly, numerical ranges are also intended to include sequential fractional integers. For example, a range expressed as "1-2%" would include 1.0%, 1.1%, 1.2%, 1.3%, 1.4%, 1.5%, 1.6%, 1.7%, 1.8%, 1.9% and 2.0%.

When a multifunctional moiety is shown, the point of attachment to the core is indicated by a line or hyphen. For example, aryloxy—refers to a moiety in which an oxygen atom is the point of attachment to the core molecule while aryl is attached to the oxygen atom.

As used herein, the term "subject" encompasses mammals and non-mammals. Examples of mammals include, but are not limited to, any member of the Mammalian class: humans; non-human primates such as chimpanzees, and other apes and monkey species; farm animals such as cattle, horses, sheep, goats, swine; domestic animals such as rabbits, dogs, and cats; and laboratory animals including rodents, such as rats, mice and guinea pigs, and the like. Examples of non-mammals include, but are not limited to, birds, fish and the like. In one embodiment of the present invention, the mammal is a human.

"Patient" includes both human and animals.

The term "inhibitor" refers to a molecule such as a compound, a drug, an enzyme activator, or a hormone that blocks or otherwise interferes with a particular biologic activity.

The term "modulator" refers to a molecule, such as a compound of the present invention, that increases or decreases, or otherwise affects the activity of a given protein, receptor and/or ion channels.

The terms "effective amount" or "therapeutically effective amount" refer to a sufficient amount of the agent to provide the desired biological result. That result can be reduction and/or alleviation of the signs, symptoms, or causes of a disease or medical condition, or any other desired alteration of a biological system. For example, an "effective amount" for therapeutic use is the amount of a compound, or of a composition comprising the compound, that is required to provide a clinically relevant change in a disease state, symptom, or medical condition. An appropriate "effective" amount in any individual case may be determined by one of ordinary skill in the art using routine experimentation. Thus, the expression "effective amount" generally refers to the quantity for which the active substance has a therapeutically desired effect.

As used herein, the terms "treat" or "treatment" encompass both "preventative" and "curative" treatment. "Preventative" treatment is meant to indicate a postponement of development of a disease, a symptom of a disease, or medical condition, suppressing symptoms that may appear, or reducing the risk of developing or recurrence of a disease or symptom. "Curative" treatment includes reducing the severity of or suppressing the worsening of an existing disease, symptom, or condition. Thus, treatment includes ameliorating or preventing the worsening of existing disease symptoms, preventing additional symptoms from occurring, ameliorating or preventing the underlying metabolic causes of symptoms, inhibiting the disorder or disease, e.g., arresting the development of the disorder or disease, relieving the disorder or disease, causing regression of the disorder or disease, relieving a condition caused by the disease or disorder, or stopping the symptoms of the disease or disorder.

As used herein, the terms "administration of" and "administering a" compound should be understood to mean providing a compound of the invention, pharmaceutical composition comprising a compound or a prodrug of a compound of the invention to an individual in need thereof. It is recognized that one skilled in the non-limiting art can treat a patient presently afflicted with neurological and psychiatric disorders or by prophylactically treat a patient afflicted with the disorders with an effective amount of the compound of the present invention.

The term "composition" as used herein is intended to encompass a product comprising the specified ingredients in the specified amounts, as well as any product which results, directly or indirectly, from combinations of the specified ingredients in the specified amounts. Such term in relation to pharmaceutical composition, is intended to encompass a product comprising the active ingredient(s) and the inert ingredient(s) that make up the carrier, as well as any product which results, directly or indirectly, from a combination, complexation or aggregation of any two or more of the ingredients, or from the other types of reactions or interactions such as to cause the dissociation of one or more of the ingredients. Accordingly, the pharmaceutical compositions of the present invention encompass any composition made by mixing a compound of the present invention and a pharmaceutically acceptable carrier.

Any formula given herein is intended to represent compounds having structures depicted by the structural formula as well as certain variations or forms. For example, compounds of any formula given herein may have asymmetric or chiral centers and therefore exist in different stereoisomeric forms. All stereoisomers, including optical isomers, enantiomers, and diastereomers, of the compounds of the general formula, and mixtures thereof, are considered to fall within the scope of the formula. Furthermore, certain structures may exist as geometric isomers (i.e., cis and trans isomers), as tautomers, or as atropisomers. All such isomeric forms, and mixtures thereof, are contemplated herein as part of the present invention. Thus, any formula given herein is intended to represent a racemate, one or more enantiomeric forms, one or more diastereomeric forms, one or more tautomeric or atropisomeric forms, and mixtures thereof.

"Stereoisomer" refers to compounds which have identical chemical constitution, but differ with regard to the arrangement of the atoms or groups in space. Stereoisomers include enantiomer, diastereomers, conformer (rotamer), geometric (cis/trans) isomer, atropisomer etc.

"Chiral" refers to molecules which have the property of non-superimposability of the mirror image partner, while the term "achiral" refers to molecules which are superimposable on their mirror image partner.

"Enantiomers" refers to two stereoisomers of a compound which are non-superimposable mirror images of one another.

"Diastereomer" refers to a stereoisomer with two or more centers of chirality and whose molecules are not mirror images of one another. Diastereomers have different physical properties, e.g., melting points, boiling points, spectral properties or biological activities. A mixture of diastereomers may be separated under high resolution analytical procedures such as electrophoresis and chromatography such as HPLC.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994.

Many organic compounds exist in optically active forms, i.e., they have the ability to rotate the plane of polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. A specific stereoisomer may be referred to as an enantiomer, and a mixture of such stereoisomers is called an enantiomeric mixture. A 50:50 mixture of enantiomers is referred to as a racemic mixture or a racemate, which may occur where there has been no stereoselection or stereospecificity in a chemical reaction or process.

Any asymmetric atom (e.g., carbon or the like) of the compound(s) disclosed herein can be in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration.

Depending on the choice of the starting materials and procedures, the compounds can be present in the form of one of the possible stereoisomers or as mixtures thereof, such as racemates and diastereoisomer mixtures, depending on the number of asymmetric carbon atoms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, a cycloalkyl substituent may have a cis- or trans-configuration relative to another substituent of the same cycloalkyl frame.

Any resulting mixtures of stereoisomers can be separated on the basis of the physicochemical differences of the constituents, into the pure or substantially pure geometric isomers, enantiomers, diastereomers, for example, by chromatography and/or fractional crystallization. Any resulting racemates of final products or intermediates can be resolved into the optical antipodes by methods known to those skilled in the art, e.g., by separation of the diastereomeric salts thereof. Racemic products can also be resolved by chiral chromatography, e.g., high performance liquid chromatography (HPLC) using a chiral adsorbent. Preferred enantiomers can also be prepared by asymmetric syntheses. See, for example, Jacques, et al., Enantiomers, Racemates and Resolutions (Wiley Interscience, New York, 1981); *Principles of Asymmetric Synthesis* (2nd Ed. Robert E. Gawley, Jeffrey Aubé, Elsevier, Oxford, UK, 2012); Eliel, E. L. Stereochemistry of Carbon Compounds (McGraw-Hill, N Y, 1962); Wilen, S. H. Tables of Resolving Agents and Optical Resolutions p. 268 (E. L. Eliel, Ed., Univ. of Notre Dame Press, Notre Dame, Ind. 1972); Chiral Separation Techniques: A Practical Approach (Subramanian, G. Ed., Wiley-VCH Verlag GmbH & Co. KGaA, Weinheim, Germany, 2007).

Diastereomeric mixtures may be separated into their individual diastereomers on the basis of their physical chemical differences by methods well known to those skilled in the art, such as, for example, by chromatography and/or fractional crystallization. Enantiomers may be separated by converting the enantiomeric mixture into a diastereomeric mixture by reaction with an appropriate optically active compound (e.g., chiral auxiliary such as a chiral alcohol or Mosher's acid chloride, or formation of a mixture of diastereomeric salts), separating the diastereomers and converting (e.g., hydrolyzing or de-salting) the individual diastereomers to the corresponding pure enantiomers. Enantiomers may also be separated by use of chiral HPLC column.

The compounds of the invention can form pharmaceutically acceptable salts, which are also within the scope of this invention. A "pharmaceutically acceptable salt" refers to a salt of a free acid or base of a compound of Formula A that is non-toxic, is physiologically tolerable, is compatible with the pharmaceutical composition in which it is formulated, and is otherwise suitable for formulation and/or administration to a subject. Reference to a compound herein is understood to include reference to a pharmaceutically acceptable salt of said compound unless otherwise indicated.

Compound salts include acidic salts formed with inorganic and/or organic acids, as well as basic salts formed with inorganic and/or organic bases. In addition, where a given compound contains both a basic moiety, such as, but not limited to, a pyridine or imidazole, and an acidic moiety, such as, but not limited to, a carboxylic acid, one of skill in the art will recognize that the compound may exist as a zwitterion ("inner salt"); such salts are included within the term "salt" as used herein. Salts of the compounds of the invention may be prepared, for example, by reacting a compound with an amount of a suitable acid or base, such as an equivalent amount, in a medium such as one in which the salt precipitates or in an aqueous medium followed by lyophilization.

Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate ("mesylate"), ethanesulfonate, benzenesulfonate, p-toluenesulfonate, and pamoate (i.e., 1,1'-methylene-bis(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counterions. Hence, a pharmaceutically acceptable salt can have one or more charged atoms and/or one or more counter ion.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, tert-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

Additionally, acids and bases which are generally considered suitable for the formation of pharmaceutically useful salts from pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; and in The Orange Book (Food & Drug Administration, MD, available from FDA). These disclosures are incorporated herein by reference thereto.

Additionally, any compound described herein is intended to refer also to any unsolvated form, or a hydrate, solvate, or polymorph of such a compound, and mixtures thereof, even if such forms are not listed explicitly. "Solvate" means a physical association of a compound of the invention with one or more solvent molecules. This physical association involves varying degrees of ionic and covalent bonding, including hydrogen bonding. In certain instances, the solvate will be capable of isolation, for example when one or more solvent molecules are incorporated in the crystal lattice of a crystalline solid. "Solvate" encompasses both solution-phase and isolatable solvates. Suitable solvates include those formed with pharmaceutically acceptable solvents such as water, ethanol, and the like. In some embodiments, the solvent is water and the solvates are hydrates.

One or more compounds of the invention may optionally be converted to a solvate. Methods for the preparation of solvates are generally known. Thus, for example, M. Caira et al., J. Pharmaceutical Sci., 93(3), 601-611 (2004), describes the preparation of the solvates of the antifungal fluconazole in ethyl acetate as well as from water. Similar preparations of solvates, hemisolvate, hydrates, and the like are described by E. C. van Tonder et al, AAPS PharmSciTech., 5(1), article 12 (2004); and A. L. Bingham et al., *Chem. Commun.*, 603-604 (2001). A typical, non-limiting process involves dissolving the compound of the invention in a suitable amount of the solvent (organic solvent or water or a mixture thereof) at a higher than ambient temperature and cooling the solution at a rate sufficient to form crystals which are then isolated by standard methods. Analytical techniques such as, for example, infrared spectroscopy, show the presence of the solvent (or water) in the crystals as a solvate (or hydrate).

The present invention also relates to pharmaceutically active metabolites of compounds of Formula (A), and uses of such metabolites in the methods of the invention. A "pharmaceutically active metabolite" means a pharmacologically active product of metabolism in the body of a compound of Formula (A) or salt thereof. Active metabolites of a compound may be determined using routine techniques known or available in the art. See, e.g., Bertolini et al., *J. Med. Chem.* 1997, 40, 2011-2016; Shan et al., *J. Pharm. Sci.* 1997, 86 (7), 765-767; Bagshawe, *Drug Dev. Res.* 1995, 34, 220-230; Bodor, *Adv. Drug Res.* 1984, 13, 255-331; Bundgaard, Design of Prodrugs (Elsevier Press, 1985); and Larsen, Design and Application of Prodrugs, Drug Design and Development (Krogsgaard-Larsen et al., eds., Harwood Academic Publishers, 1991).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{125}I$, respectively. Such isotopically labelled compounds are useful in metabolic studies (for example with $^{14}C$), reaction kinetic studies (with, for example $^{2}H$ or $^{3}H$), detection or imaging techniques [such as positron emission tomography (PET) or single-photon emission computed tomography (SPECT) including drug or substrate tissue distribution assays, or in radioactive treatment of patients. In particular, an $^{18}F$ or $^{11}C$ labeled compound may be particularly suitable for PET or SPECT studies. Further, substitution with heavier isotopes such as deuterium (i.e., $^{2}H$) may afford certain therapeutic advantages resulting from greater metabolic stability, for example increased in vivo half-life or reduced dosage requirements. Isotopically labeled compounds of this invention can generally be prepared by carrying out the procedures disclosed in the schemes or in the examples and preparations described below by substituting a readily available isotopically labeled reagent for a non-isotopically labeled reagent.

The use of the terms "salt," "solvate," "polymorph," and the like, with respect to the compounds described herein is intended to apply equally to the salt, solvate, and polymorph forms of enantiomers, stereoisomers, rotamers, tautomers, atropisomers, and racemates of the compounds of the invention.

The present invention relates to particular molecules and pharmaceutically acceptable salts or isomers thereof. The invention further relates to molecules which are useful in modulating H3R and pharmaceutically acceptable salts, solvates, esters, or isomers thereof.

The invention is directed to compounds as described herein and pharmaceutically acceptable salts, solvates, esters, or isomers thereof, and pharmaceutical compositions comprising one or more compounds as described herein and pharmaceutically acceptable salts or isomers thereof. One aspect of this invention is the provision of compounds, compositions, kits, and antidotes for modulating H3R in mammals having a compound of the Formula (A) or pharmaceutically acceptable salt thereof,

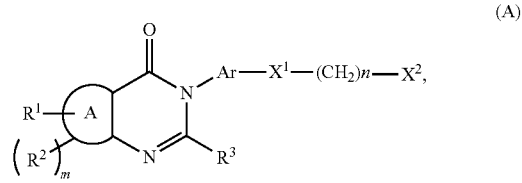

(A)

wherein, $R^1$ and $R^2$ is independently H or $SF_5$, with the provision of one of $R^1$ and $R^2$ is $SF_5$ at least;
$R^3$ is $C_{1-6}$ alkyl or $C_{3-6}$ cycloalkyl;
Ring A is a $C_{6-8}$ aryl; Ar is $C_{5-6}$ aryl, wherein the $C_{5-6}$ aryl is optionally substituted with 1, 2, 3 or 4 $R^e$;
$R^e$ is H, halogen, CN, $NO_2$, OH, $C_{1-6}$ alkoxy or $C_{1-6}$ alkyl;
$X^1$ is S or O;
$X^2$ is

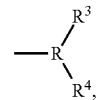

wherein R is N or C;
$R^3$ and $R^4$ is $C_{1-6}$ alkyl, or $R^3$ and $R^4$ together with R to which they are attached, form a $C_{3-7}$ carbocyclic ring, 3- to 7-membered heterocyclic ring, and wherein each of the $C_{3-7}$ carbocyclic ring, 3- to 7-membered heterocyclic ring is independently optionally substituted with 1, 2, 3, 4, 5 or 6 $R^f$;
$R^f$ is $C_{1-6}$ alkyl, $C_{3-6}$ cycloalkyl, $-C(=O)R^a$, and wherein each of the $C_{1-6}$ alkyl, $C_{3-6}$ cycloalkyl, $-C(=O)R^a$ is independently optionally substituted with $C_{1-6}$ alkyl;
$R^a$ is $C_{1-6}$ alkyl, $C_{3-6}$ cycloalkyl or 3- to 7-membered heterocyclic ring;
m is an integer from 0 to 3;
n is an integer from 0 to 5.
In one embodiment, $R^3$ is $C_{1-4}$ alkyl or $C_{3-6}$ cycloalkyl
In one embodiment, A is phenyl.
In one embodiment, Ar is phenyl, wherein the phenyl is optionally substituted with 1, 2, 3 or 4 $R^e$.
In one embodiment, Ar is the following sub-formula:

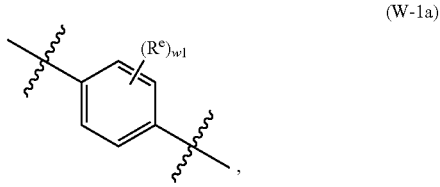

(W-1a)

wherein w1 is 0, 1, 2, 3 or 4.
In one embodiment, $R^e$ is H, F, Cl, Br, I, CN, $NO_2$, OH, methyl, ethyl, i-propyl, n-propyl, n-butyl, t-butyl, methoxy, ethoxy.

In one embodiment, $R^3$ and $R^4$ is $C_{1-4}$ alkyl.

In one embodiment, R is N, $R^3$ and $R^4$ together with the nitrogen atom to which they are attached, form a 3- to 7-membered heterocyclic ring, and wherein the 3- to 7-membered heterocyclic ring is independently optionally substituted with 1, 2, 3, 4 or 5 $R^f$.

In one embodiment, R is C, $R^3$ and $R^4$ together with the carbon atom to which they are attached, form a $C_{3-7}$ carbocyclic ring, 3- to 7-membered heterocyclic ring, and wherein each of the $C_{3-7}$ carbocyclic ring, 3- to 7-membered heterocyclic ring is independently optionally substituted with 1, 2, 3, 4 or 5 $R^f$.

In one embodiment, $R^f$ is $C_{1-4}$ alkyl, $C_{3-6}$ cycloalkyl, —C(=O)$R^a$.

In one embodiment, R is —C(=O)$R^a$, methyl, ethyl t-propyl,

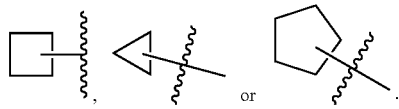

In one embodiment, $R^a$ is methyl, ethyl,

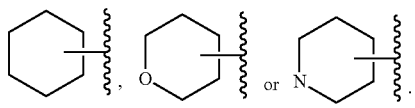

In one embodiment, $X^2$ is one of the following sub-formulae:

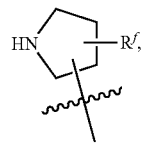

(X-1a)

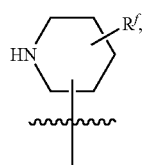

(X-2a)

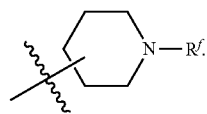

(X-3a)

In one embodiment, $X^2$ is one of the following sub-formulae:

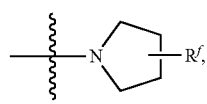

(X-1b)

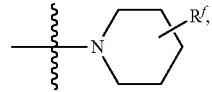

(X-2b)

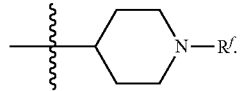

(X-3b)

In one embodiment, provided herein is a compound having the Formula (B),

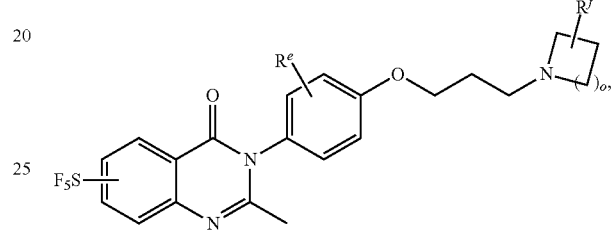

(B)

wherein o is an integer from 0 to 4; and $R^e$, $R^f$ are as defined herein.

In one embodiment, provided herein is a compound having the Formula (C),

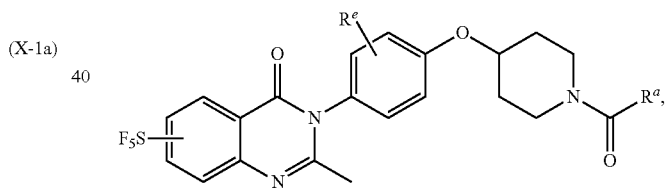

(C)

$R^e$, $R^a$ are as defined herein.

In one embodiment, provided herein is a compound having the Formula (D),

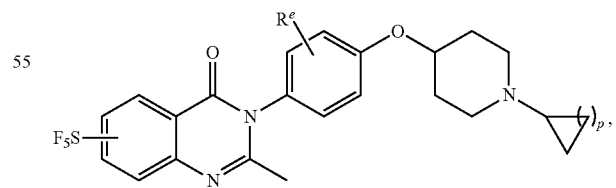

(D)

wherein p is an integer from 1 to 5; and $R^e$ is as defined herein.

In yet another embodiment, provided herein is a compound having one of the following structures or a pharmaceutically acceptable salt,

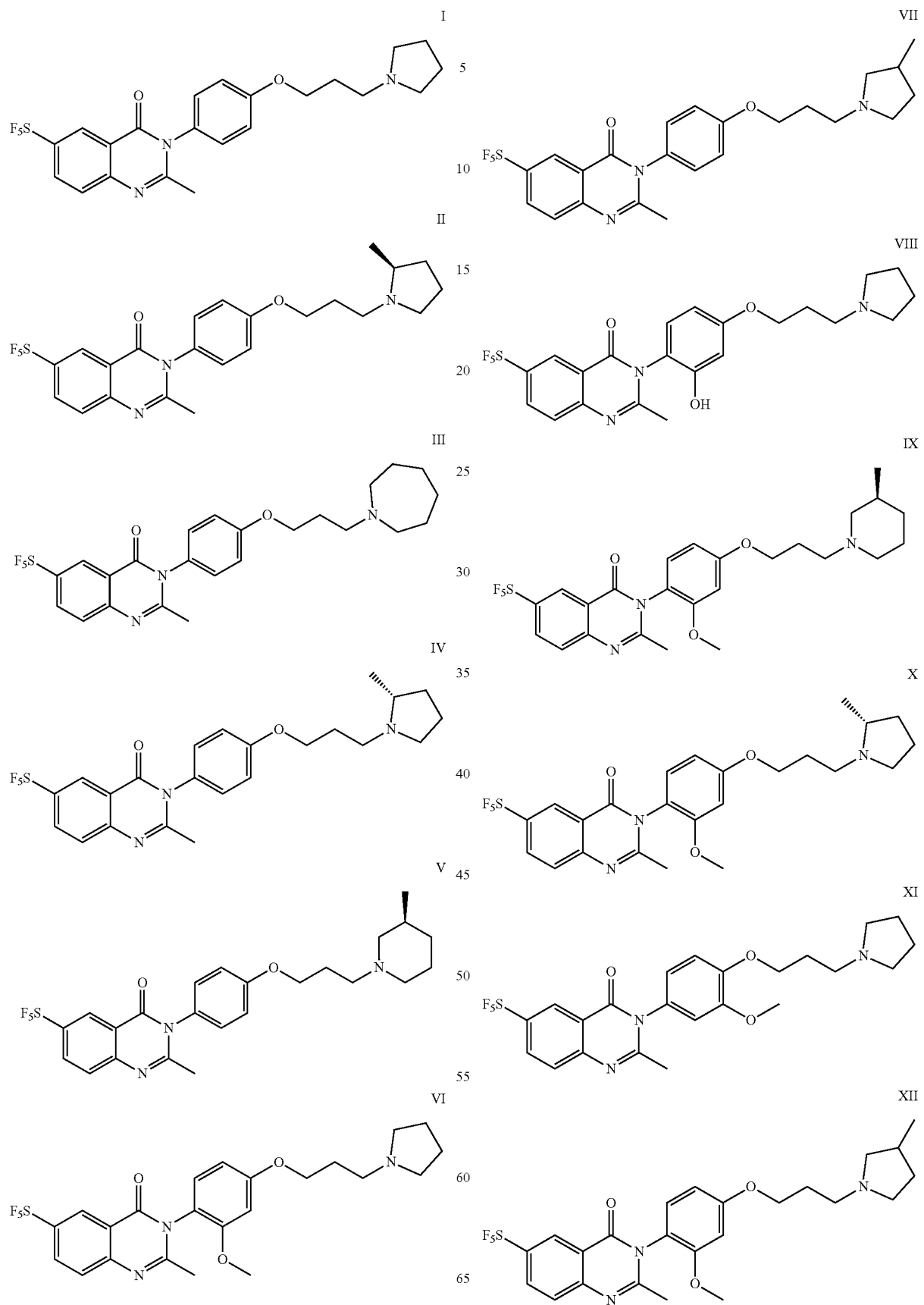

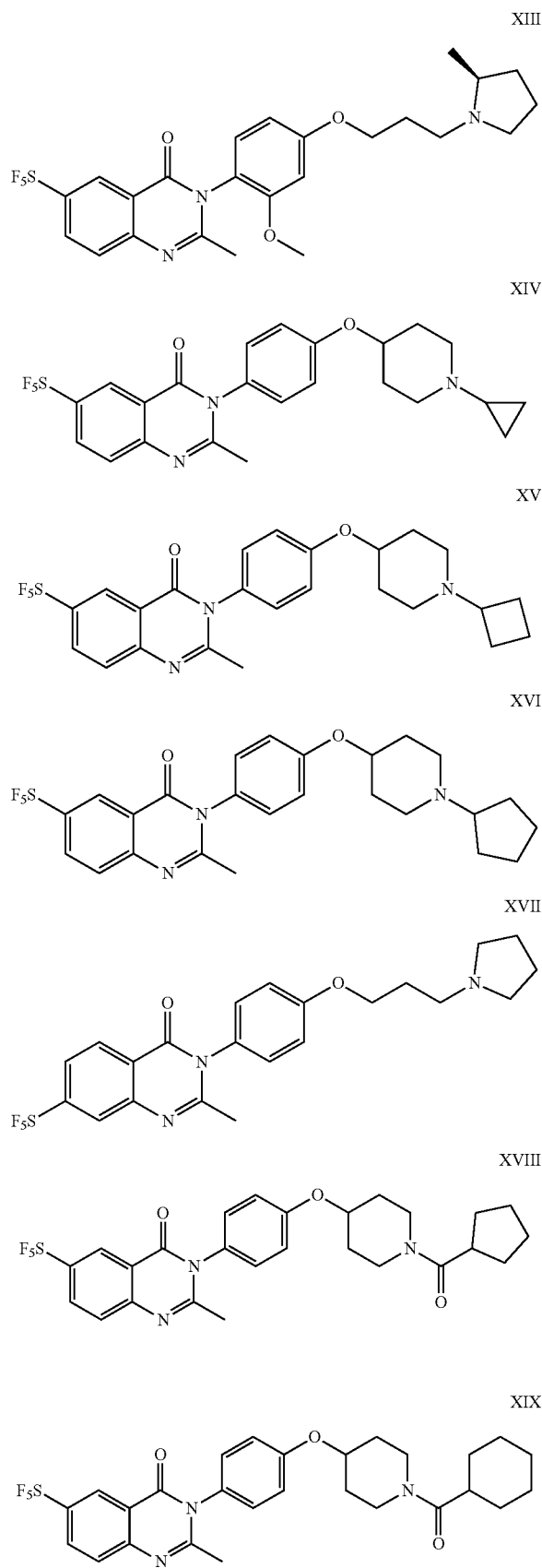
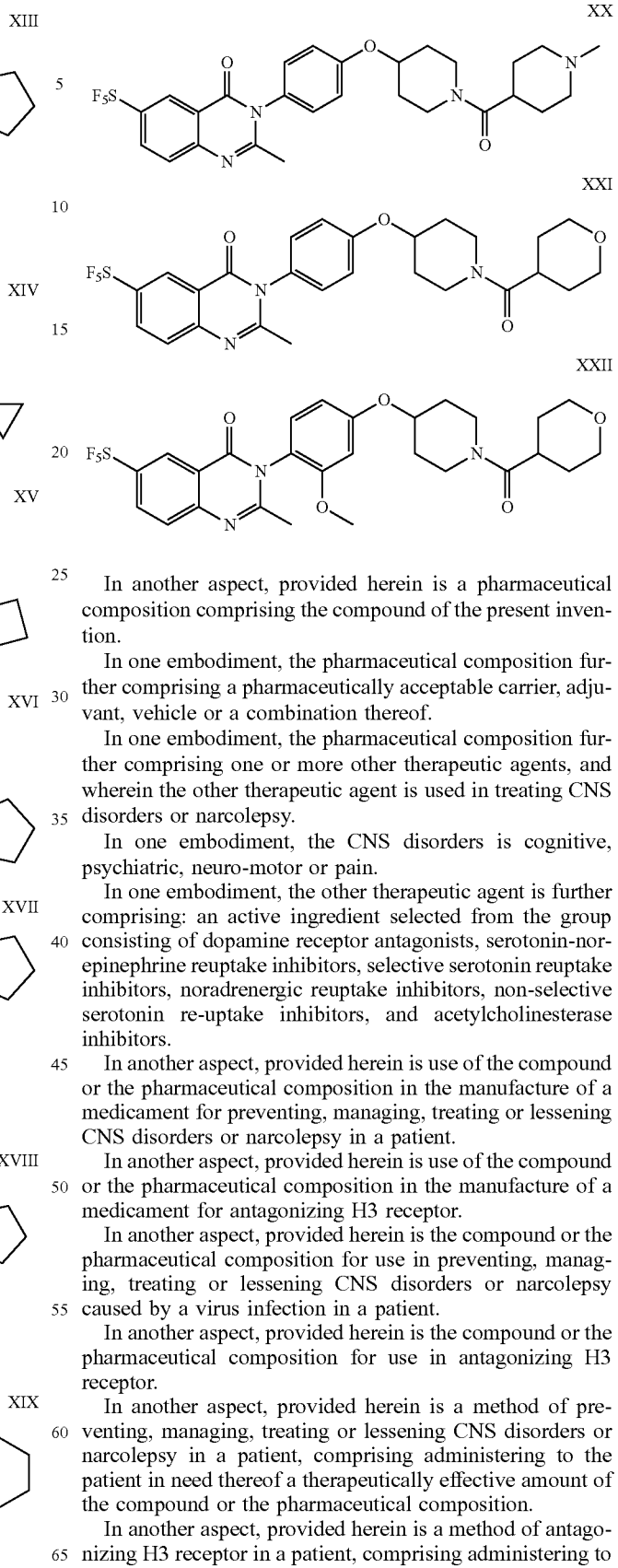

In another aspect, provided herein is a pharmaceutical composition comprising the compound of the present invention.

In one embodiment, the pharmaceutical composition further comprising a pharmaceutically acceptable carrier, adjuvant, vehicle or a combination thereof.

In one embodiment, the pharmaceutical composition further comprising one or more other therapeutic agents, and wherein the other therapeutic agent is used in treating CNS disorders or narcolepsy.

In one embodiment, the CNS disorders is cognitive, psychiatric, neuro-motor or pain.

In one embodiment, the other therapeutic agent is further comprising: an active ingredient selected from the group consisting of dopamine receptor antagonists, serotonin-norepinephrine reuptake inhibitors, selective serotonin reuptake inhibitors, noradrenergic reuptake inhibitors, non-selective serotonin re-uptake inhibitors, and acetylcholinesterase inhibitors.

In another aspect, provided herein is use of the compound or the pharmaceutical composition in the manufacture of a medicament for preventing, managing, treating or lessening CNS disorders or narcolepsy in a patient.

In another aspect, provided herein is use of the compound or the pharmaceutical composition in the manufacture of a medicament for antagonizing H3 receptor.

In another aspect, provided herein is the compound or the pharmaceutical composition for use in preventing, managing, treating or lessening CNS disorders or narcolepsy caused by a virus infection in a patient.

In another aspect, provided herein is the compound or the pharmaceutical composition for use in antagonizing H3 receptor.

In another aspect, provided herein is a method of preventing, managing, treating or lessening CNS disorders or narcolepsy in a patient, comprising administering to the patient in need thereof a therapeutically effective amount of the compound or the pharmaceutical composition.

In another aspect, provided herein is a method of antagonizing H3 receptor in a patient, comprising administering to the patient in need thereof a therapeutically effective amount of the compound or the pharmaceutical composition.

In yet another aspect, the present invention is directed to methods of making compounds of Formula (A) (D) and pharmaceutically acceptable salts thereof.

The present invention provides a pharmaceutical composition comprising compounds of the present invention, e.g., example compounds. According to the specific examples of the present invention, the pharmaceutical composition can further comprise pharmaceutically acceptable excipient, carrier, adjuvant, solvent and a combination thereof.

The present invention provides a method of treating, preventing or ameliorating a disease or disorder, comprising administrating a safe and effective amount of a combination of drugs containing compounds of the invention and one or more therapeutic active agents. Among them, the combination of drugs comprises one or more additional drugs for treatment of CNS disorders or narcolepsy.

Other drugs for treatment of CNS disorders or narcolepsy include, but are not limited to: further comprising: an active ingredient selected from the group consisting of dopamine receptor antagonists, serotonin-norepinephrine reuptake inhibitors, selective serotonin reuptake inhibitors, noradrenergic reuptake inhibitors, non-selective serotonin re-uptake inhibitors, and acetylcholinesterase inhibitors.

The amount of the compound of the pharmaceutical composition disclosed herein refers to an amount which can be effectively detected to modulate dysfunctional H3R of biology samples and in a patient. The active ingredient may be administered to subjects in need of such treatment in dosage that will provide optimal pharmaceutical efficacy, which is not limited to the desired therapeutic effects, on the route of administration, and on the duration of the treatment. The dosage will vary from patient to patient depending upon the nature and severity of disease, the patient's weight, special diet then being followed by a patient, concurrent medication, and other factors which those skilled in the art will recognize. The quantity of active compound in a unit dose of preparation may be varied or adjusted from about 1 mg to about 1000 mg, preferably from about 1 mg to about 500 mg, more preferably from about 1 mg to about 300 mg, still more preferably from about 1 mg to about 200 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required. The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 10 mg/day to 200 mg/day, which may be administered in single or multiple doses. In yet another embodiment about 1 mg to 50 mg per patient per day.

It will also be appreciated that certain of the compounds of the present invention can exist in free form for treatment, or where appropriate, as a pharmaceutically acceptable derivative or a prodrug thereof. A pharmaceutically acceptable derivative includes pharmaceutically acceptable salts, esters, salts of such esters, or any other adduct or derivative which upon administration to a patient in need thereof provide, directly or indirectly, a compound as otherwise described herein, or a therapeutically effective metabolite or residue thereof.

The pharmaceutical compositions of the invention may be prepared and packaged in bulk form wherein a safe and effective amount of a compound of Formula (A) disclosed herein can be extracted and then given to the patient, such as with powders or syrups. Generally, dosage levels of between 0.0001 to 10 mg/kg of body weight daily are administered to the patient to obtain effective modulation of dysfunctional H3R. Alternatively, the pharmaceutical compositions of the invention may be prepared and packaged in unit dosage form wherein each physically discrete unit contains a safe and effective amount of a compound of Formula (A) disclosed herein. When prepared in unit dosage form, the pharmaceutical compositions of the invention commonly contain from about 0.5 mg to 1 g, or 1 mg to 500 mg, or 5 mg to 200 mg, or more preferably, 25 mg to 100 mg of the compound of the invention.

When the pharmaceutical compositions of the present invention also contain one or more other active ingredients, in addition to a compound of the present invention, the weight ratio of the compound of the present invention to the second active ingredient may be varied and depend upon the effective dose of each ingredient. Thus, for example, when a compound of the present invention is combined with another agent, the weight ratio of the compound of the present invention to the other agent will generally range from about 1000:1 to about 1:1000, such as about 200:1 to 1:200. Combinations of a compound of the present invention and other active ingredients will generally also be within the aforementioned range, but in each case, an effective dose of each active ingredient in the combination should be used.

"Pharmaceutically acceptable excipient" as used herein means a pharmaceutically acceptable material, composition or vehicle involved in giving form or consistency to the pharmaceutical composition. Each excipient must be compatible with the other ingredients of the pharmaceutical composition when commingled, such that interactions which would substantially reduce the efficacy of the compound of the invention when administered to a patient and would result in pharmaceutically unacceptable compositions. In addition, each excipient must of course be of sufficiently high purity to render it pharmaceutically acceptable.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting the compound of the present invention once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, humectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are resources that are available to the skilled artisan that describe pharmaceutically acceptable excipients and may be useful in selecting suitable pharmaceutically acceptable excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

In Remington: The Science and Practice of Pharmacy, 21st edition, 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

The pharmaceutical compositions of the invention are prepared using techniques and methods known to those skilled in the art. Some of the methods commonly used in the art are described in Remington's Pharmaceutical Sciences (Mack Publishing Company).

Therefore, another aspect of the present invention is related to a method for preparing a pharmaceutical composition. The pharmaceutical composition contains the compound disclosed herein and pharmaceutically acceptable excipient, carrier, adjuvant, vehicle or a combination thereof, the method comprises mixing various ingredients. The pharmaceutical composition containing the compound disclosed herein can be prepared for example at normal ambient temperature and pressure.

The compound of the invention will typically be formulated into a dosage form adapted for administration to the patient by the desired route of administration. For example, dosage forms include those adapted for (1) oral administration such as tablets, capsules, caplets, pills, troches, powders, syrups, elixirs, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

The pharmaceutical compositions provided herein may be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenylsalicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and ascorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art to modify or sustain dissolution of the active ingredient.

The pharmaceutical compositions provided herein may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquids or solvent, emulsifying agent, and preservative. Suspensions may include a pharmaceutically acceptable suspending agent and preservative. Aqueous alcoholic solutions may include a pharmaceutically acceptable acetal, such as a di(lower alkyl)acetal of a lower alkyl aldehyde, e.g., acetaldehyde diethyl acetal; and a water-miscible solvent having one or more hydroxy groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

Where appropriate, dosage unit formulations for oral administration can be microencapsulated. The formulation can also be prepared to prolong or sustain the release as for example by coating or embedding particulate material in polymers, wax, or the like.

The pharmaceutical compositions provided herein for oral administration may be also provided in the forms of liposomes, micelles, microspheres, or nanosystems. Micellar dosage forms can be prepared as described in U.S. Pat. No. 6,350,458.

The pharmaceutical compositions provided herein may be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all above dosage forms.

The compounds disclosed herein can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, polyepsilon-caprolactone, polyhydroxybutyric acid, polyorthoesters, polyacetals, polydihydroxypyrans, polycyanoacrylates and crosslinked or amphipathic block copolymers of hydrogels.

The pharmaceutical compositions provided herein may be formulated as immediate or modified release dosage forms, including delayed, sustained, pulsed, controlled, targeted, and programmed-release forms.

The pharmaceutical compositions provided herein may be co-formulated with other active ingredients which do not impair the desired therapeutic action, or with substances that supplement the desired action.

The pharmaceutical compositions provided herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

The pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, Remington: The Science and Practice of Pharmacy, supra).

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylceluose, hydroxypropyl methylcellulose, and polyvinylpyrrolidone. Suitable emulsifying agents include those described herein, including polyoxyethylene sorbitan monolaurate, polyoxyethylene sorbitan monooleate 80 and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL, CyDex, Lenexa, Kans.).

The pharmaceutical compositions provided herein may be formulated for single or multiple dosage administration. The single dosage formulations are packaged in an ampoule, a vial, or a syringe. The multiple dosage parenteral formulations must contain an antimicrobial agent at bacteriostatic or fungistatic concentrations. All parenteral formulations must be sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a sterile vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions may be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

In other aspect, the pharmaceutical composition of the invention is prepared to a dosage form adapted for administration to a patient by inhalation, for example as a dry powder, an aerosol, a suspension, or a solution composition. In one embodiment, the invention is directed to a dosage form adapted for administration to a patient by inhalation as a dry powder. In one embodiment, the invention is directed to a dosage form adapted for administration to a patient by inhalation as a dry powder. Dry powder compositions for delivery to the lung by inhalation typically comprise a compound disclosed herein or a pharmaceutically acceptable salt thereof as a finely divided powder together with one or more pharmaceutically-acceptable excipients as finely divided powders. Pharmaceutically-acceptable excipients particularly suited for use in dry powders are known to those skilled in the art and include lactose, starch, mannitol, and mono-, di-, and polysaccharides. The finely divided powder may be prepared by, for example, micronization and milling. Generally, the size-reduced (e.g. micronized) compound can be defined by a $D_{50}$ value of about 1 to about 10 microns (for example as measured using laser diffraction).

Aerosols may be formed by suspending or dissolving a compound disclosed herein or a pharmaceutically acceptable salt thereof in a liquified propellant. Suitable propellants include halocarbons, hydrocarbons, and other liquefied gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising a compound of formula (A) or a pharmaceutically acceptable salt thereof will typically be administered to a patient via a metered dose inhaler (MDI). Such devices are known to those skilled in the art.

The aerosol may contain additional pharmaceutically-acceptable excipients typically used with MDIs such as surfactants, lubricants, cosolvents and other excipients to improve the physical stability of the formulation, to improve valve performance, to improve solubility, or to improve taste.

Pharmaceutical compositions adapted for transdermal administration may be presented as discrete patches intended to remain in intimate contact with the epidermis of the patient for a prolonged period of time. For example, the active ingredient may be delivered from the patch by iontophoresis as generally described in *Pharmaceutical Research*, 3(6), 318 (1986).

Pharmaceutical compositions adapted for topical administration may be formulated as ointments, creams, suspensions, lotions, powders, solutions, pastes, gels, sprays, aerosols or oils. Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminum stearate, cetostearyl alcohol, polyethylene glycols, woolfat, beeswax, carboxypolymethylene and cellulose derivatives, and/or glyceryl monostearate and/or nonionic emulsifying agents.

Lotions may be formulated with an aqueous or oily base and will in general also contain one or more emulsifying agents, stabilizing agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilizing agents, suspending agents or preservatives.

Topical preparations may be administered via one or more applications per day to the affected area; over skin areas occlusive dressings may advantageously be used. Continuous or prolonged delivery may be achieved via an adhesive reservoir system.

Compounds or pharmaceutical compositions of the invention disclosed herein can be used in the manufacture of a medicament for treating, preventing, ameliorating or mitigating a disorder or disease in a subject, as well as other medicaments for modulating (e.g., antagonizing) H3R, and the compounds of this invention have superior pharmacokinetic and pharmacodynamic properties, fewer toxic side-effect.

Specifically, the amount of the compound of compositions of the present invention can effectively and detectably modulate (e.g., antagonizing) H3R. The compounds or pharmaceutical compositions of the invention may be used for preventing, treating or alleviating diseases relating to H3R, wherein such diseases which includes, CNS disorders or narcolepsy.

In one embodiment, the therapies disclosed herein comprise administrating a safe and effective amount of the compound of the invention or the pharmaceutical composition containing the compound of the invention to patients in need. Each example disclosed herein comprises the method of treating the diseases above comprising administrating a safe and effective amount of the compound of the invention or the pharmaceutical composition containing the compound of the invention to patients in need.

In one embodiment, the compound of the invention or the pharmaceutical composition thereof may be administered by any suitable route of administration, including both systemic administration and topical administration. Systemic administration includes oral administration, parenteral administration, transdermal administration and rectal administration. Parenteral administration refers to routes of administration other than enteral or transdermal, and is typically by injection or infusion. Parenteral administration includes intravenous, intramuscular, and subcutaneous injection or infusion. Topical administration includes application to the skin as well as intraocular, intravaginal, inhaled and intranasal administration. In one embodiment, the compound of the invention or the pharmaceutical composition thereof may be administered orally. In another embodiment, the compound of the invention or the pharmaceutical composition thereof may be administered by inhalation. In a further embodiment, the compound of the invention or the pharmaceutical composition thereof may be administered intranasal.

In one embodiment, the compound of the invention or the pharmaceutical composition thereof may be administered once or according to a dosing regimen wherein multiple doses are administered at varying intervals of time for a given period of time. For example, doses may be administered one, two, three, or four times per day. In one embodiment, a dose is administered once per day. In a further embodiment, a dose is administered twice per day. Doses may be administered until the desired therapeutic effect is achieved or indefinitely to maintain the desired therapeutic effect. Suitable dosing regimens for the compound of the invention or the pharmaceutical composition thereof depend on the pharmacokinetic properties of that compound, such as its absorption, distribution, and half-lives of metabolism and elimination, which can be determined by the skilled artisan. In addition, suitable dosing regimens, including the duration such regimens are administered, for the compound of the invention or the pharmaceutical composition thereof depend on the disorder being treated, the severity of the disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's tolerance to the dosing regimen or over time as individual patient needs change.

The compounds of the present invention may be administered either simultaneously with, or before or after, one or more other therapeutic agents. The compounds of the present invention may be administered separately, by the same or different route of administration, or together in the same pharmaceutical composition as the other agents.

The pharmaceutical composition or combination of the present invention can be in unit dosage of about 1-1000 mg of active ingredients for a subject of about 50-70 kg, preferably about 1-500 mg or about 1-250 mg or about 1-150 mg or about 0.5-100 mg or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties can be correlated with in vitro and in vivo tests using advantageously mammals, e.g., mice, rats, dogs, non-human primates, such as monkeys or isolated organs, tissues and preparations thereof. The compounds of the present invention can be applied in vitro in the form of solutions, e.g., preferably aqueous solutions, and in vivo via topically, inhalingly, enterally or parenterally, advantageously intravenously, e.g., as a suspension or in aqueous solution.

In one embodiment, a therapeutically effective dosage of the compound disclosed herein from about 0.1 mg to about 1,000 mg per day. The pharmaceutical compositions should provide a dosage of from about 0.1 mg to about 1,000 mg of the compound. In a special embodiment, pharmaceutical dosage unit forms are prepared to provide from about 1 mg to about 1,000 mg, about 10 mg to about 500 mg, about 20 mg to about 200 mg, about 25 mg to about 100 mg, or about 30 mg to about 60 mg of the active ingredient or a combination of essential ingredients per dosage unit form. In a special embodiment, pharmaceutical dosage unit forms are prepared to provide about 1 mg, 5 mg, 10 mg, 20 mg, 25 mg, 50 mg, 100 mg, 250 mg, 500 mg, 1000 mg of the active ingredient.

The following examples are provided so that the invention might be more fully understood. However, it should be understood that these embodiments merely provide a method of practicing the present invention, and the present invention is not limited to these embodiments.

Generally, the compounds disclosed herein may be prepared by methods described herein, wherein the substituents are as defined for Formula (A) above, except where further noted. The following non-limiting schemes and examples are presented to further exemplify the invention.

Professionals skilled in the art will recognize that the chemical reactions described may be readily adapted to prepare a number of other compounds disclosed herein, and alternative methods for preparing the compounds disclosed herein are deemed to be within the scope disclosed herein. Those having skill in the art will recognize that the starting materials may be varied and additional steps employed to produce compounds encompassed by the present inventions, as demonstrated by the following examples. In some cases, protection of certain reactive functionalities may be necessary to achieve some of the above transformations. In general, such need for protecting groups, as well as the conditions necessary to attach and remove such groups, will be apparent to those skilled in the art of organic synthesis. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, the known reaction conditions or the reaction disclosed in the present invention will be recognized as having applicability for preparing other compounds disclosed herein.

In the examples described below, unless otherwise indicated all temperatures are set forth in degrees Celsius. Reagents were purchased from commercial suppliers such as Aldrich Chemical Company, Arcos Chemical Company, Alfa Aesar Chemical Company and J&K Chemical Company, and were used without further purification unless otherwise indicated.

Compounds of the present invention, including salts, esters, hydrates, or solvates thereof, can be prepared using any known organic synthesis techniques and can be synthesized according to any of numerous possible synthetic routes.

The reactions for preparing compounds of the present invention can be carried out in suitable solvents, which can be readily selected by one skilled in the art of organic synthesis. Suitable solvents can be substantially non-reactive with the starting materials (reactants), the intermediates, or products at the temperatures at which the reactions are carried out, e.g., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected by a skilled artisan.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high-performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) ("Preparative LC-MS Purification: Improved Compound Specific Method Optimization" Karl F. Blom, Brian Glass, Richard Sparks, Andrew P. Combs *J. Combi. Chem.* 2004, 6(6), 874-883, which is incorporated herein by reference in its entirety) and normal phase silica chromatography.

Compounds of the present invention can be synthesized using the methods described below, together with synthetic methods known in the art of synthetic organic chemistry, or variations thereon as appreciated by those skilled in the art. Preferred methods include but are not limited to those methods described below. Specifically, the compounds of the present invention of Formula (B D) can be synthesized by following the steps outlined in the exemplary general synthetic schemes listed below, and the abbreviations for the reactants or for the chemical groups of the reactants included in the synthetic schemes are defined in the Examples.

General synthetic schemes (1-7) towards compounds having Formula (B), (C) and (D) are shown as follows.

Scheme 1
General synthesis of compound having Formula (B)

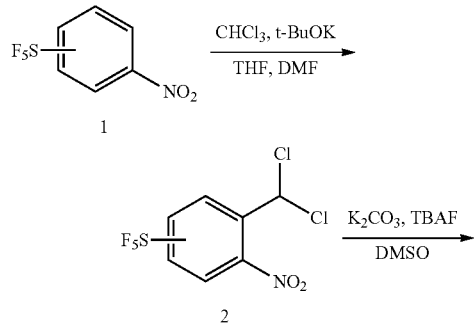

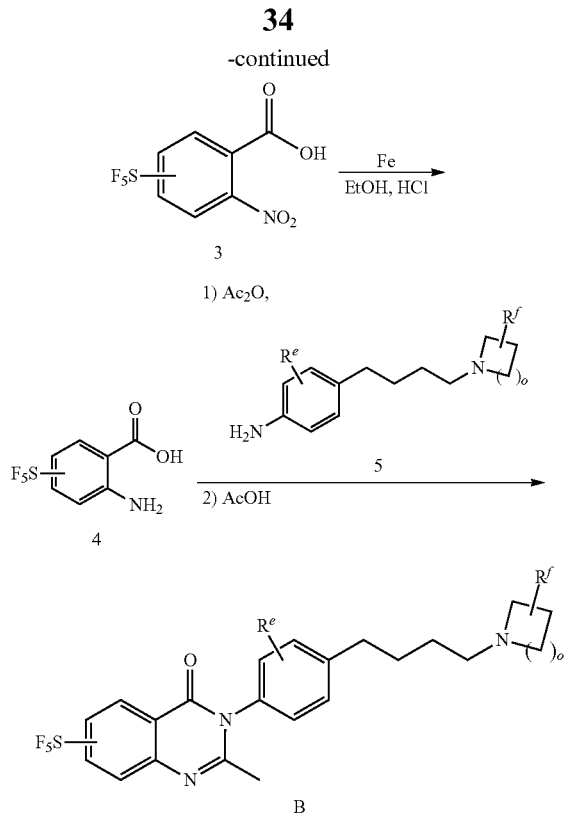

Following scheme 1, the synthesis towards compounds having Formula (B) can be conducted according to the relevant procedures disclosed in references (*Journal of Organic Chemistry*, 2011, 76, 4781-4786; *Tetrahedron Letters*, 2004, 45, 1071-1074; *Organic Letters*, 2009, 11, 15, 3230-3233; *Journal of Medicinal Chemistry*, 2008, 51, 4780-4789; and U.S. Application Publication No. 2005182045A1), but is not limited to these disclosed procedures. A nitrobenzene derivative 1 is alkalized with chloroform and then hydrolyzed to form acid 3, which is reduced by Fe in HCl to give aniline 4. Thus, the condensation of acid 4 with 5 followed by cyclization reaction affords compound (B).

Scheme 2
Synthesis of intermediate compound 5

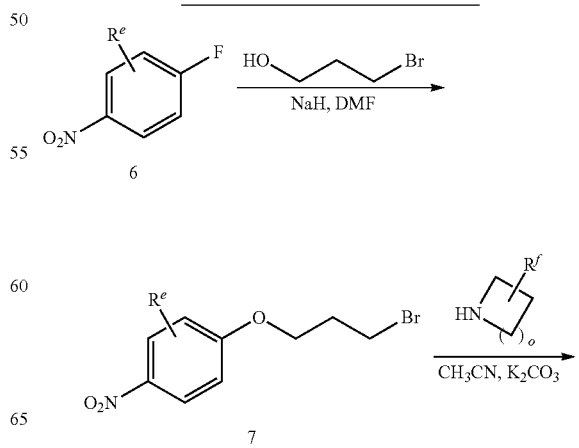

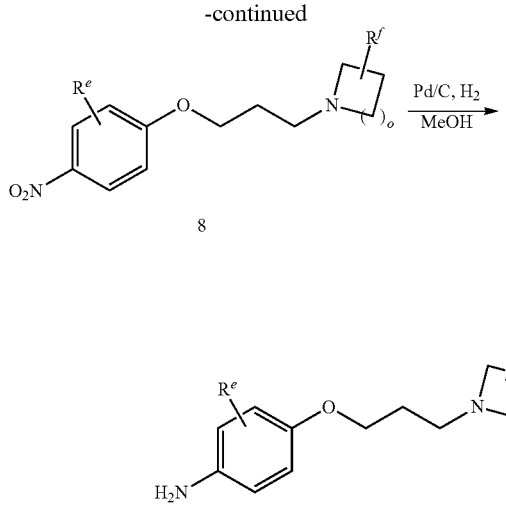

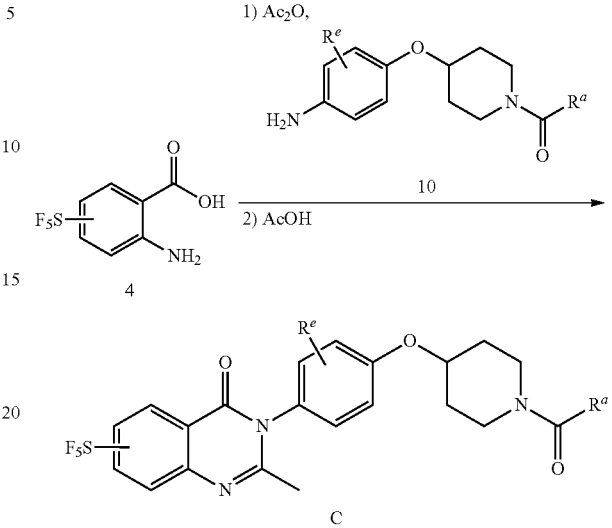

Scheme 4
General synthesis of compound having Formula (C)

Following scheme 2, the synthesis towards compounds having Formula (5) can be conducted according to the relevant procedures disclosed in references (U.S. Application Publication No. 2005182045A1; and PCT International Application No. WO 2017201161A1), but is not limited to these disclosed procedures. A fluorobenzene derivative 6 is substituted by hydroxyalkyl bromide to give phenyl ether 7, which is then aminated to compound 8. Thus, the subsequent hydrogenation in the presence of Pd/C affords intermediate 5.

Following scheme 4, the synthesis towards compounds having Formula (C) can be conducted according to the relevant procedures disclosed in references (U.S. Application Publication No. 2005182045A1; and PCT International Application No. WO 2017201161A1), but is not limited to these disclosed procedures. An aniline derivative 4 is cyclized with 10 to afford compound (C).

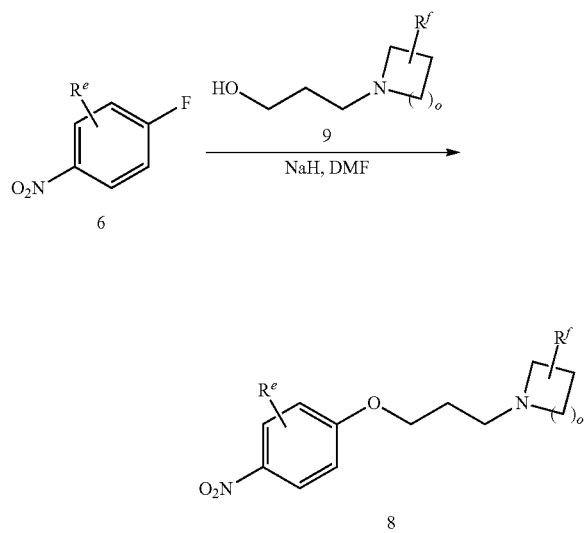

Scheme 3
Alternative synthesis of intermediate compound 8

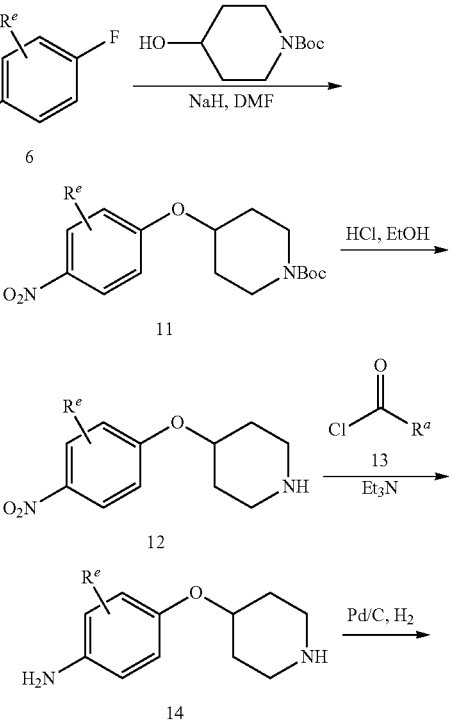

Scheme 5
Synthesis of intermediate compound 10

Alternatively, following scheme 3, the synthesis towards compounds having Formula (8) can be conducted according to the relevant procedures disclosed in references (U.S. Application Publication No. 2005182045A1; and PCT International Publication No. WO 2017201161A1), but is not limited to these disclosed procedures. A fluorobenzene derivative 6 is substituted by an alcohol derivative 9 to form phenyl ether compound 8.

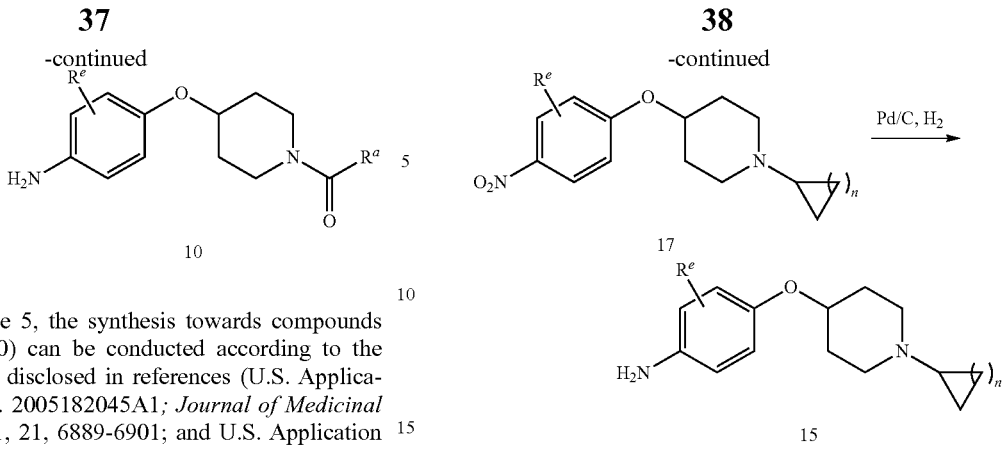

Following scheme 5, the synthesis towards compounds having Formula (10) can be conducted according to the relevant procedures disclosed in references (U.S. Application Publication No. 2005182045A1; *Journal of Medicinal Chemistry*, 2008, 51, 21, 6889-6901; and U.S. Application Publication No. 2009306375A1), but is not limited to these disclosed procedures. A fluorobenzene derivative 6 is substituted by N-Boc-piperdine-4-ol to form nitrobenzene derivative 11, which undergoes deprotection to give amine 12. Thus, compound 12 is acylated followed by reduction to afford compound 10.

Scheme 6
General synthesis of compound having Formula (D)

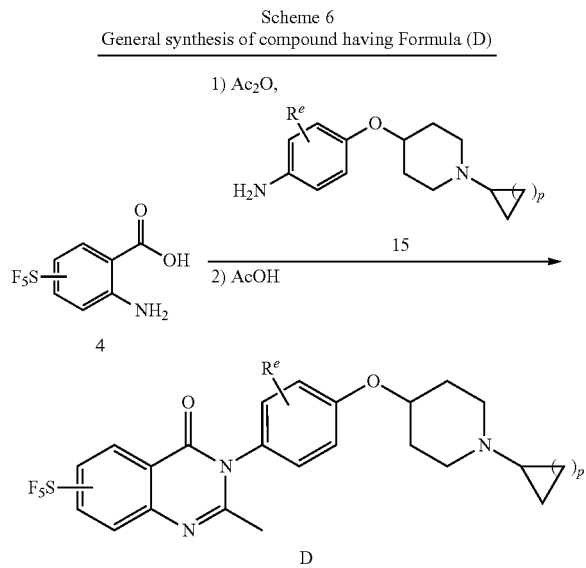

Following scheme 6, the synthesis towards compounds having Formula (D) can be conducted according to the relevant procedures disclosed in references (U.S. Application Publication No. 2005182045A1; and PCT International Application No. WO 2017201161A1), but is not limited to these disclosed procedures. An aniline derivative 4 is cyclized with compound 15 to afford compound D.

Scheme 7
Synthesis of intermediate compound 15

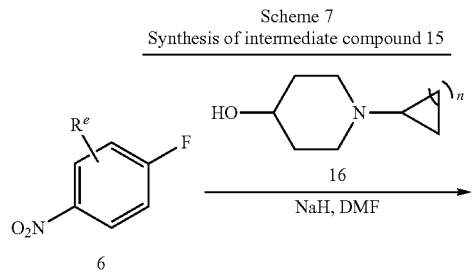

Following scheme 7, the synthesis towards compounds having Formula (15) can be conducted according to the relevant procedures disclosed in reference (U.S. Application Publication No. 2005182045A1), but is not limited to these disclosed procedures. A fluorobenzene derivative 6 is substituted by an alcohol derivative 16 to form phenyl ether 17, which is reduced to afford compound 15.

Compounds encompassed in the present disclosure may be prepared via different schemes. Detailed preparation processes of 22 exemplary compounds via various schemes are described below and the characterization results are listed as well.

Unless stated otherwise, all reagents were purchased from commercial suppliers without further purification. Solvent drying by standard methods was employed when necessary. The plates used for thin-layer chromatography (TLC) were E. Merck silica gel 60F254 (0.24 nm thickness) precoated on aluminum plates, and then visualized under UV light (365 nm and 254 nm) or through staining with a 5% of dodecamolybdophosphoric acid in ethanol and subsequent heating. Column chromatography was performed using silica gel (200-400 mesh) from commercial suppliers. $^1$H-NMR spectra were recorded on an Agilent 400-MR NMR spectrometer (400.00 MHz for 1H) at room temperature. Solvent signal was used as reference for $^1$H-NMR (CDCl$_3$, 7.26 ppm; CD$_3$OD, 3.31 ppm; DMSO-d$_6$, 2.50 ppm; D$_2$O, 4.79 ppm). The following abbreviations were used to explain the multiplicities: s=singlet, d=doublet, t=triplet, q=quartet, br. s.=broad singlet, dd=double doublet, td=triple doublet, dt=double triplet, dq=double quartet, m=multiplet. Other abbreviations used in the experimental details are as follows: δ=chemical shift in parts per million downfield from tetramethylsilane, Ar=aryl, Ac=acyl, Boc=tert-butyloxy carbonyl, Bn=Benzyl, DCM=dichloromethane, DCE=dichloroethane, DMF=N,N'-dimethylformamide, NMP=N-methyl-2-pyrrolidone, DIBAL-H=diisobutyl aluminium hydride, DIPEA=diisopropylethylamine, DMAP=4-(dimethylamino) pyridine, DMSO=dimethyl sulphoxide, EA=ethyl acetate, Et=ethyl, Me=methyl, Hz=hertz, HPLC=high performance liquid chromatography, J=coupling constant (in NMR), min=minute(s), h=hour(s), NMR=nuclear magnetic resonance, prep=preparative, PE=petroleum ether, t-Bu=tert-butyl, iPr=isopropyl, TBAF=tetrabutylammonium fluoride, tert=tertiary, TFA=trifluoroacetic acid, THF=tetrahydrofuran, TLC=thin-layer chromatography.

ASPECTS OF THE INVENTION

The invention is further defined by the following aspects.

Aspect 1. A compound having Formula (I):

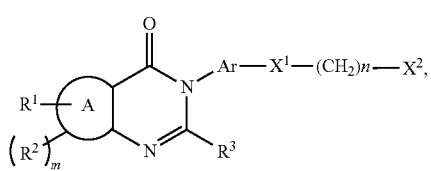

(A)

or a pharmaceutically acceptable salt, wherein, $R^1$ and $R^2$ is independently H or $SF_5$, with the provision of one of $R^1$ and $R^2$ is $SF_5$ at least;

$R^3$ is $C_{1-6}$ alkyl or $C_{3-6}$ cycloalkyl;

Ring A is a $C_{6-8}$ aryl;

Ar is $C_{5-6}$ aryl, wherein the $C_{5-6}$ aryl is optionally substituted with 1, 2, 3 or 4 $R^e$;

$R^e$ is H, halogen, CN, $NO_2$, OH, $C_{1-6}$ alkoxy or $C_{1-6}$ alkyl;

X is S or O;

$X^2$ is

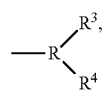

wherein R is N or C;

$R^3$ and $R^4$ is $C_{1-6}$ alkyl, or $R^3$ and $R^4$ together with R to which they are attached, form a $C_{3-7}$ carbocyclic ring, 3- to 7-membered heterocyclic ring, and wherein each of the $C_{3-7}$ carbocyclic ring, 3- to 7-membered heterocyclic ring is independently optionally substituted with 1, 2, 3, 4, 5 or 6 $R^f$;

$R^f$ is $C_{1-6}$ alkyl, $C_{3-6}$ cycloalkyl, —C(=O)$R^a$, and wherein each of the $C_{1-6}$ alkyl, $C_{3-6}$ cycloalkyl, —C(=O)$R^a$ is independently optionally substituted with $C_{1-6}$ alkyl;

$R^a$ is $C_{1-6}$ alkyl, $C_{3-6}$ cycloalkyl or 3- to 7-membered heterocyclic ring;

m is an integer from 0 to 3;

n is an integer from 0 to 5.

Aspect 2. The compound of aspect 1, wherein $R^3$ is $C_{1-4}$ alkyl or $C_{3-6}$ cycloalkyl.

Aspect 3. The compound of any one of aspects 1 to 2, wherein A is phenyl.

Aspect 4. The compound of any one of aspects 1 to 3, wherein Ar is phenyl, wherein the phenyl is optionally substituted with 1, 2, 3 or 4 $R^e$.

Aspect 5. The compound of any one of aspects 1 to 3, wherein Ar is the following sub-formula:

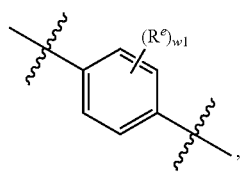

(W-1a)

wherein w1 is 0, 1, 2, 3 or 4.

Aspect 6. The compound of any one of aspects 1 to 5, wherein $R^e$ is H, F, Cl, Br, I, CN, $NO_2$, OH, methyl, ethyl, i-propyl, n-propyl, n-butyl, t-butyl, methoxy, ethoxy.

Aspect 7. The compound of any one of aspects 1 to 6, wherein $R^3$ and $R^4$ is $C_{1-4}$ alkyl.

Aspect 8. The compound of any one of aspects 1 to 6, R is N, $R^3$ and $R^4$ together with the nitrogen atom to which they are attached, form a 3- to 7-membered heterocyclic ring, and wherein the 3- to 7-membered heterocyclic ring is independently optionally substituted with 1, 2, 3, 4 or 5 $R^f$;

Aspect 9. The compound of any one of aspects 1 to 6, R is C, $R^3$ and $R^4$ together with the carbon atom to which they are attached, form a $C_{3-7}$ carbocyclic ring, 3- to 7-membered heterocyclic ring, and wherein each of the $C_{3-7}$ carbocyclic ring, 3- to 7-membered heterocyclic ring is independently optionally substituted with 1, 2, 3, 4 or 5 $R^f$.

Aspect 10. The compound of anyone of aspects 1 to 9, $R^f$ is $C_{1-4}$ alkyl, $C_{3-6}$ cycloalkyl, —C(=O)$R^a$.

Aspect 11. The compound of any one of aspects 1 to 9, wherein $R^f$ is —C(=O)$R^a$, methyl, ethyl, i-propyl,

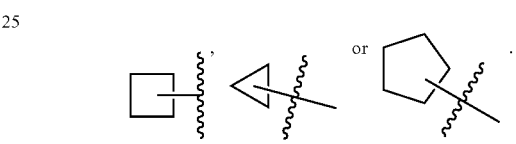

Aspect 12. The compound of any one of aspects 1 to 11, wherein $R^a$ is methyl, ethyl,

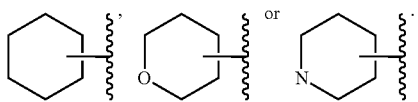

Aspect 13. The compound of any one of aspects 1 to 12, wherein $X^2$ is one of the following sub-formulae:

(X-1a)

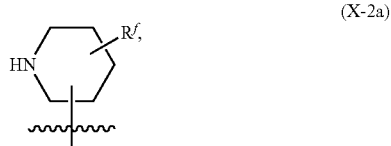

(X-2a)

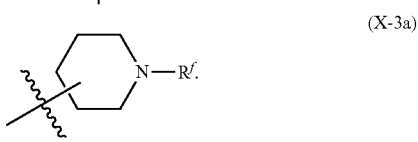

(X-3a)

Aspect 14. The compound of any one of aspects 1 to 12, wherein $X^2$ is one of the following sub-formulae:

Aspect 15. The compound of aspect 1 having any one of Formula (B)-(D), (B)

(C)

(D)

wherein o is an integer from 0 to 4; p is an integer from 1 to 5.

Aspect 16. The compound of any of aspects 1 to 15, wherein any of the carbon-hydrogen bond can be replaced with a carbon-deuterium bond.

Aspect 17. A compound having one of the following structures,

I

II

III

IV

V

VI

VII
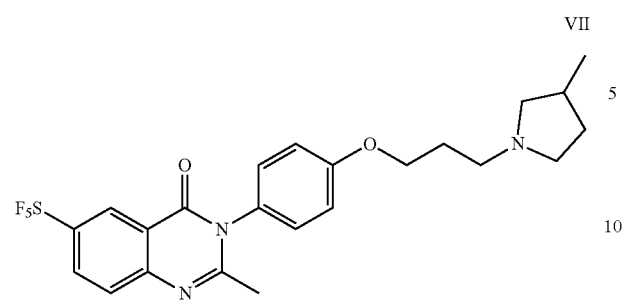
VIII
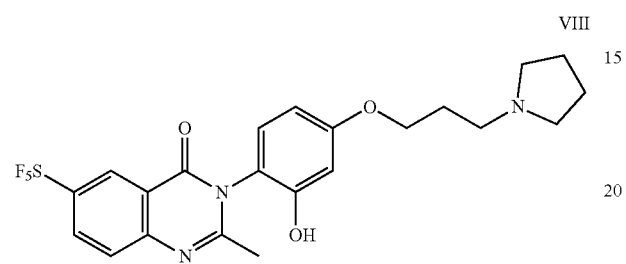
IX
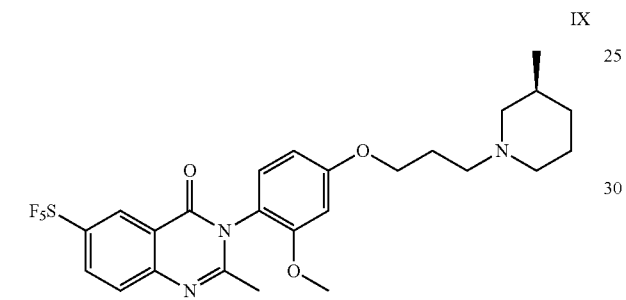
X
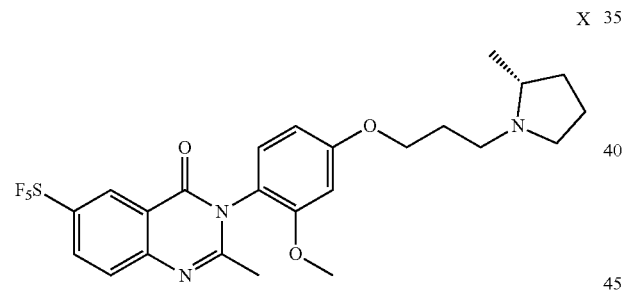
XI
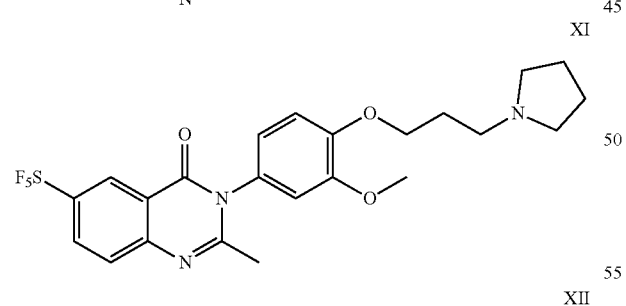
XII
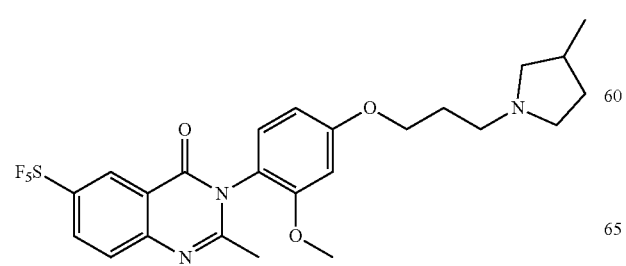
XIII
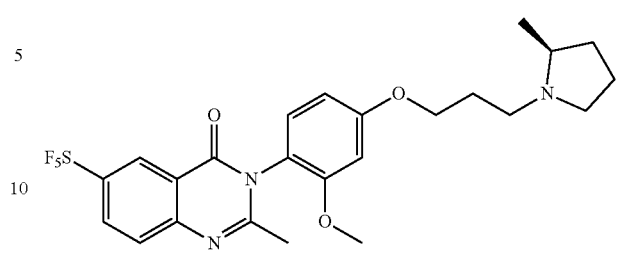
XIV
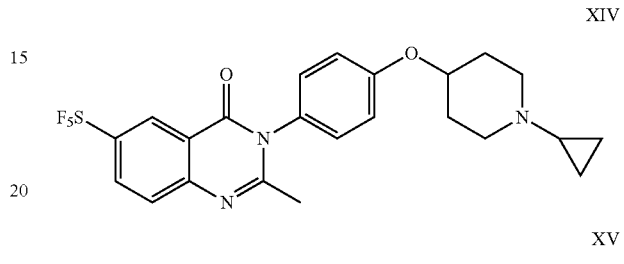
XV
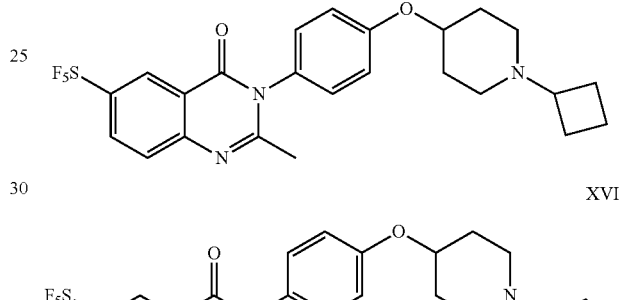
XVI
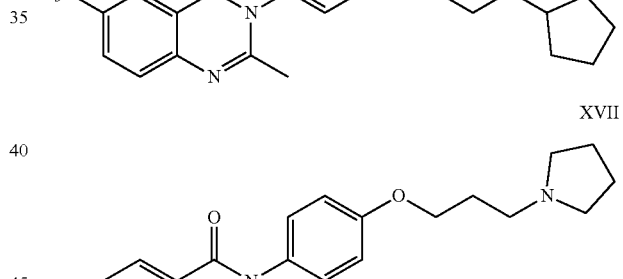
XVII
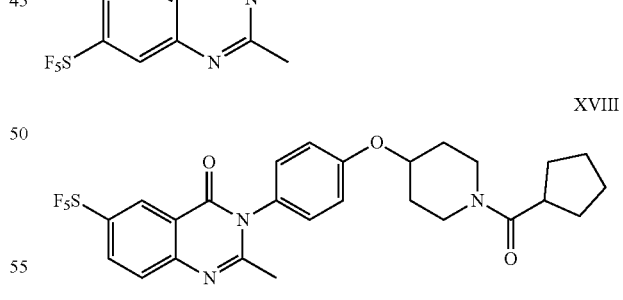
XVIII
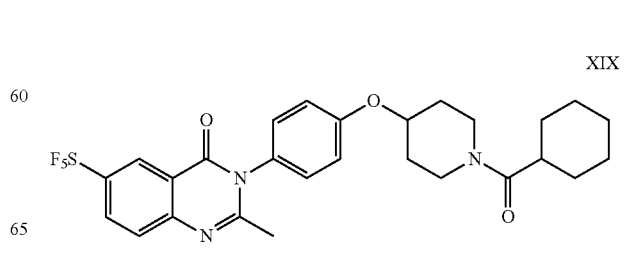
XIX
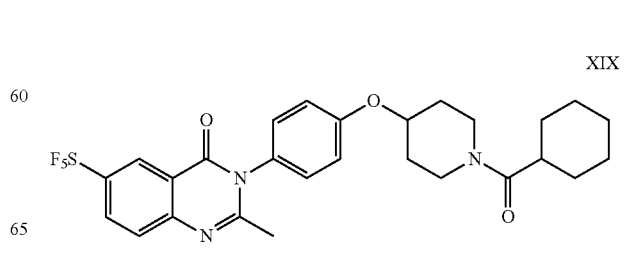

XX
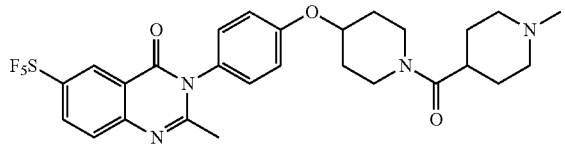

XXI
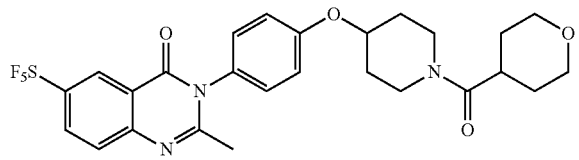

XXII
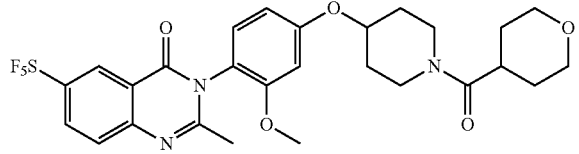

or a pharmaceutically acceptable salt.

Aspect 18. A pharmaceutical composition comprising the compound of any one of aspects 1 to 17.

Aspect 19. The pharmaceutical composition of aspect 18 further comprising a pharmaceutically acceptable carrier, adjuvant, vehicle or a combination thereof.

Aspect 20. The pharmaceutical composition of aspect 18 further comprising one or more other therapeutic agents, and wherein the other therapeutic agent is used in treating CNS disorders or narcolepsy.

Aspect 21. The pharmaceutical composition of aspect 20, wherein CNS disorders is cognitive, psychiatric, neuromotor or pain.

Aspect 22. The pharmaceutical composition of aspect 20, wherein the other therapeutic agent is further comprising: an active ingredient selected from the group consisting of dopamine receptor antagonists, serotonin-norepinephrine reuptake inhibitors, selective serotonin reuptake inhibitors, noradrenergic reuptake inhibitors, non-selective serotonin re-uptake inhibitors, and/or acetylcholinesterase inhibitors.

Aspect 23. Use of the compound of any one of aspects 1 to 17 or the pharmaceutical composition of any one of aspects 18 to 22 in the manufacture of a medicament for preventing, managing, treating or lessening CNS disorders or narcolepsy in a patient.

Aspect 24. Use of the compound of any one of aspects 1 to 17 or the pharmaceutical composition of any one of aspects 18 to 22 in the manufacture of a medicament for antagonizing H3 receptor.

Aspect 25. The compound of any one of aspects 1 to 17 or the pharmaceutical composition of any one of aspects 18 to 22 for use in preventing, managing, treating or lessening CNS disorders or narcolepsy caused by a virus infection in a patient.

Aspect 26. The compound of any one of aspects 1 to 17 or the pharmaceutical composition of any one of aspects 18 to 22 for use in antagonizing H3 receptor.

Aspect 27. A method of preventing, managing, treating or lessening CNS disorders or narcolepsy in a patient, comprising administering to the patient in need thereof a therapeutically effective amount of the compound of any one of aspects 1 to 17 or the pharmaceutical composition of any one of aspects 18 to 22.

Aspect 28. A method of antagonizing H3 receptor in a patient, comprising administering to the patient in need thereof a therapeutically effective amount of the compound of any one of aspects 1 to 17 or the pharmaceutical composition of any one of aspects 18 to 22.

EXAMPLES

It should be noted that embodiments of the present invention described in detail below are exemplary for explaining the present invention only, and not be construed as limiting the present invention. Examples without a specific technology or condition can be implemented according to technology or condition in the documentation of the art or according to the product instructions. The reagents or instruments without manufacturers are available through conventional purchase. Those having skill in the art will recognize that the starting materials may be varied and additional steps employed to produce compounds encompassed by the present inventions, as demonstrated by the following examples.

I
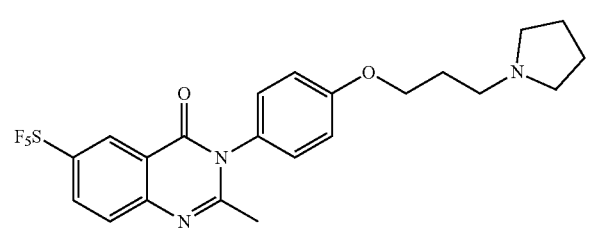

II
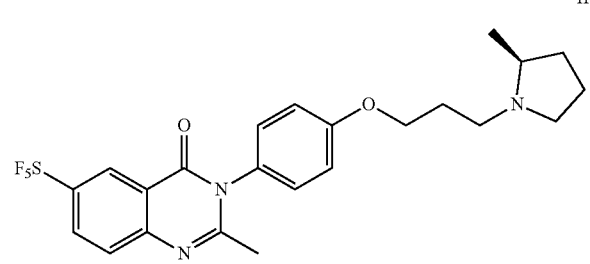

III
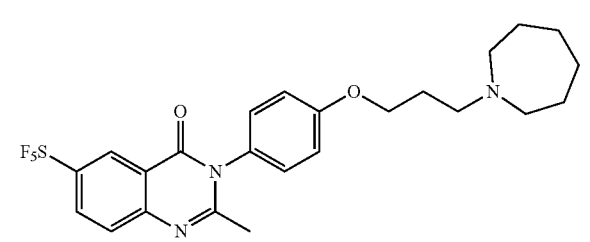

IV
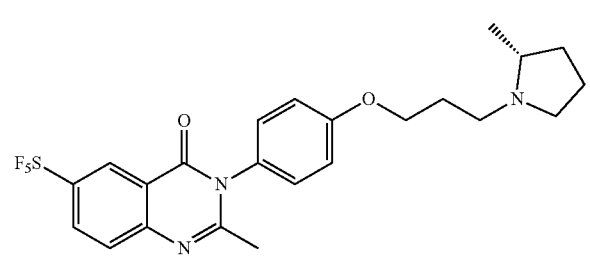

-continued

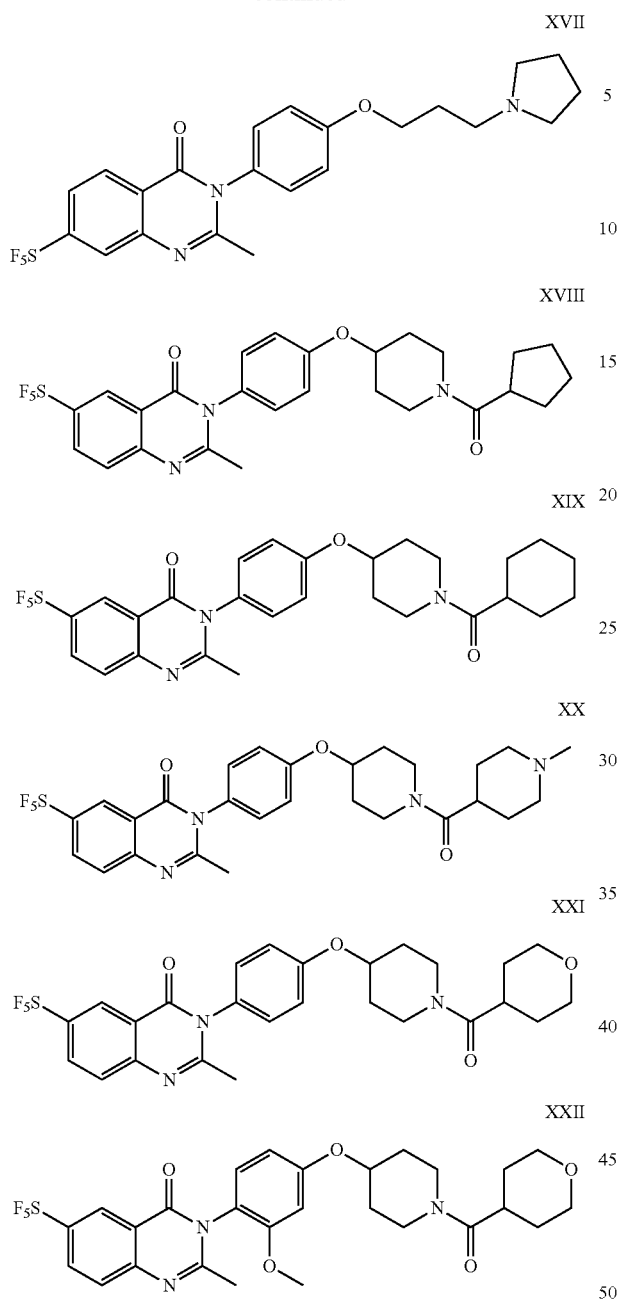

Example 1

2-methyl-3-(4-(3-(pyrrolidin-1-yl)propoxy)phenyl)-6-(pentafluorosulfanyl) quinazolin-4(3H)-one (1)

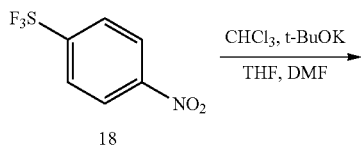

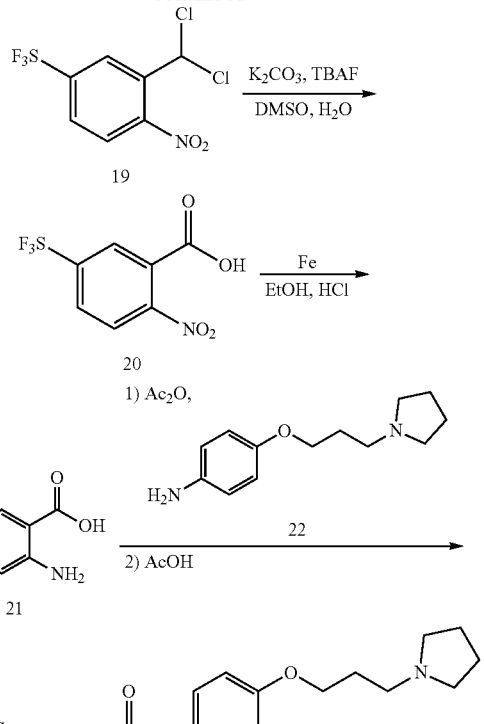

Step 1: 2-(dichloromethyl)-1-nitro-4-(pentafluorosulfanyl)benzene (19)

To a solution of t-BuOK (8.1 g, 72.2 mmol) in dry DMF (60 mL) and THF (60 mL) was added a solution of 1-nitro-4-(pentafluorosulfanyl)benzene (18) (6.0 g, 24.1 mmol) and CHCl$_3$ (3.0 g, 25.3 mmol) in DMF (30 mL) dropwise at −78° C. under N$_2$ atmosphere. The reaction was stirred at −78° C. for 0.5 h and then quenched with aqueous HCl solution (2 M) until pH=4. The resulting mixture was diluted with water (200 mL) and extracted with EA (2×100 mL). The combined organic phase was washed with brine (100 mL), dried over anhydrous Na$_2$SO$_4$, filtered and concentrated. The residue was purified by column chromatography (silica gel, PE/EA=100:1) to afford the titled compound 19 (6.0 g, 75%) as a yellow oil. $^1$H-NMR (400 MHz, CDCl$_3$) δ=8.56 (s, 1H), 8.09 (d, J=9.2 Hz, 1H), 7.96 (dd, J=2.0, 8.8 Hz, 1H), 7.52 (s, 1H).

Step 2: 2-nitro-5-(pentafluorosulfanyl)benzoic acid (20)

To a stirred solution of 2-(dichloromethyl)-1-nitro-4-(pentafluorosulfanyl)benzene (19) (0.5 g, 1.5 mmol) in DMSO (5 mL) were added K$_2$CO$_3$ (0.6 g, 4.5 mmol) and TBAF (72.3 mg, 0.3 mmol). The reaction was stirred at 25° C. for 16 h and then acidified with aqueous HCl solution (1 M) to pH=4. The resulting mixture was extracted with EA (2×5 mL). The combined organic phase was washed with brine (10 mL), dried over anhydrous MgSO$_4$, filtered and concentrated. The residue was purified by column chromatography (silica gel, PE/EA=5:1 and DCM/MeOH=10:1) to afford the titled compound 20 (0.2 g, 50%) as an off-white solid. $^1$H-NMR (400 MHz, CDCl$_3$) δ=8.31 (s, 1H), 8.07 (d, J=8.8 Hz, 1H), 7.92 (d, J=8.8 Hz, 1H).

Step 3: 2-amino-5-(pentafluorosulfanyl)benzoic acid (21)

To a stirred suspension of 2-nitro-5-(pentafluorosulfanyl) benzoic acid (20) (0.2 g, 0.7 mmol) in EtOH (1 mL) and concentrated HCl (0.3 mL) was added Fe powder (123.0 mg, 2.2 mmol) in one portion. The reaction was heated under reflux for 1 h and then concentrated. The residue was dissolved in water (5 mL) and extracted with EA (2×5 mL). The combined organic phase was washed with brine (10 mL), dried over anhydrous MgSO$_4$, filtered and concentrated to afford the titled compound 21 (190 mg, 98%) as a brown solid. $^1$H-NMR (400 MHz, CD$_3$OD) δ=8.20 (d, J=2.4 Hz, 1H), 7.58 (dd, J=2.8, 9.2 Hz, 1H), 6.77 (d, J=9.2 Hz, 1H); MS (ESI): [M+H]$^+$=263.7.

Step 4: 2-methyl-3-(4-(3-(pyrrolidin-1-yl)propoxy) phenyl)-6-(pentafluorosulfanyl) quinazolin-4(3H)-one (I)

A solution of 2-amino-5-(pentafluorosulfanyl)benzoic acid (21) (0.2 g, 0.8 mmol) in Ac$_2$O (2 mL) was heated under reflux for 4 h and then concentrated. To the residue were added 4-(3-(pyrrolidin-1-yl)propoxy)aniline (22) (0.2 g, 0.9 mmol) and AcOH (2 mL). The reaction was stirred at 80° C. for 2 h and then concentrated. The residue was purified by prep-HPLC to afford the titled compound I (120 mg, 32%) as a gray solid. $^1$H-NMR (400 MHz, CD$_3$OD) δ=8.65 (d, J=2.4 Hz, 1H), 8.40 (dd, J=2.4, 9.0 Hz, 1H), 7.91 (d, J=8.8 Hz, 1H), 7.39 (d, J=8.8 Hz, 2H), 7.21 (d, J=8.8 Hz, 2H), 4.23 (t, J=5.6 Hz, 2H), 3.78-3.69 (m, 2H), 3.51-3.42 (m, 2H), 3.22-3.09 (m, 2H), 2.46 (s, 3H), 2.35-2.25 (m, 2H), 2.25-2.15 (m, 2H), 2.13-2.01 (m, 2H); MS (ESI): [M+H]$^+$=489.9.

Example 2

(S)-2-methyl-3-(4-(3-(2-methylpyrrolidin-1-yl) propoxy)phenyl)-6-(pentafluorosulfanyl)quinazolin-4(3H)-one (II)

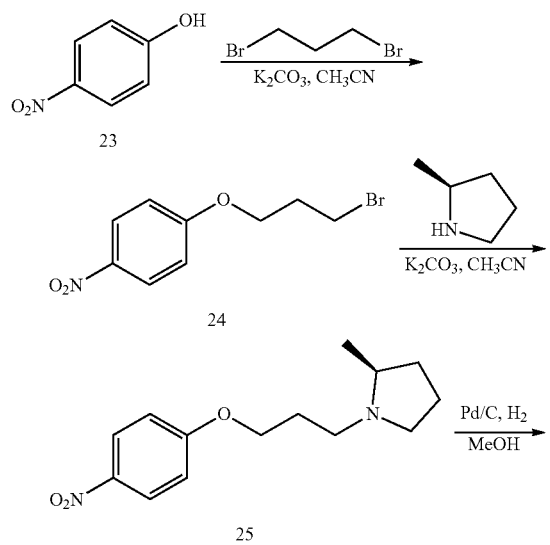

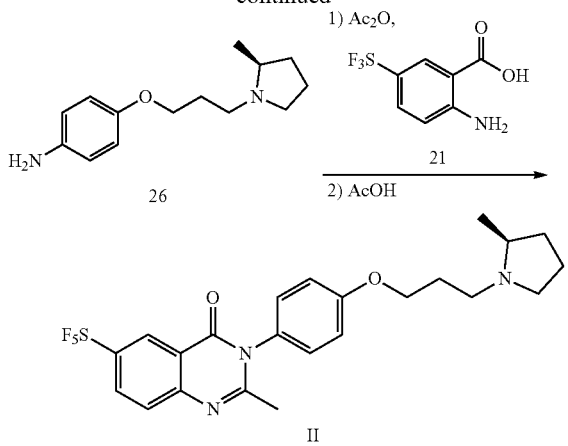

Step 1: 1-(3-bromopropoxy)-4-nitrobenzene (24)

To a stirred suspension of 4-nitrophenol (23) (2.0 g, 14.4 mmol) in CH$_3$CN (30 mL) was added 1,3-dibromopropane (5.8 g, 28.8 mmol) and K$_2$CO$_3$ (6.0 g, 43.2 mmol) at 25° C. The reaction was stirred at 80° C. for 16 h and then concentrated. The residue was partitioned between EA (20 mL) and water (10 mL). The organic phase was washed with brine (10 mL), dried over anhydrous Na$_2$SO$_4$, filtered and concentrated. The residue was purified by column chromatography (silica gel, PE/EA=10:1) to afford the titled compound 24 (2.1 g, 57%) as an off-white solid.

Step 2: (S)-2-methyl-1-(3-(4-nitrophenoxy)propyl) pyrrolidine (25)

To a stirred suspension of 1-(3-bromopropoxy)-4-nitrobenzene (24) (260 mg, 1.0 mmol) in CH$_3$CN (4 mL) were added K$_2$CO$_3$ (276 mg, 2.0 mmol) and (S)-2-methylpyrrolidine (170 mg, 2.0 mmol) at 25° C. The reaction was stirred at 80° C. for 16 h and then concentrated. The residue was partitioned between EA (10 mL) and water (5 mL). The organic phase was washed with brine (5 mL), dried over anhydrous Na$_2$SO$_4$, filtered and concentrated. The residue was purified by column chromatography (silica gel, DCM/MeOH=10:1) to afford the titled compound 25 (251 mg, 95%) as a yellow oil. MS (ESI): [M+H]$^+$=264.9.

Step 3: (S)-4-(3-(2-methylpyrrolidin-1-yl)propoxy) aniline (26)

To a stirred suspension of (S)-2-methyl-1-(3-(4-nitrophenoxy)propyl)pyrrolidine (25) (251 mg, 1.0 mmol) in MeOH (5 mL) was added Pd/C (25 mg, 10%) in one portion at 25° C. The reaction was stirred at 25° C. under H$_2$ atmosphere for 16 h and then filtered through Celite®. The filtered cake was washed with MeOH (5 mL). The combined filtrate was concentrated to afford the titled compound 26 (222 mg, 100%) as a red oil. MS (ESI): [M+H]$^+$=234.9.

Step 4: (S)-2-methyl-3-(4-(3-(2-methylpyrrolidin-1-yl)propoxy)phenyl)-6-(pentafluorosulfanyl)quinazolin-4(3H)-one (II)

A solution of 2-amino-5-(pentafluorosulfanyl)benzoic acid (21) (50 mg, 0.2 mmol) in Ac$_2$O (1 mL) was heated under reflux for 4 h and then concentrated. To the residue were added (S)-4-(3-(2-methylpyrrolidin-1-yl)propoxy)aniline (26) (54 mg, 0.2 mmol) and AcOH (1 mL) at 25° C. The reaction was stirred at 80° C. for 1 h and then concentrated. The residue was partitioned between EA (10 mL) and saturated aqueous $NaHCO_3$ solution (5 mL). The organic phase was washed with brine (5 mL), dried over anhydrous $Na_2SO_4$, filtered and concentrated. The residue was purified by prep-HPLC to afford the titled compound II (40 mg in HCl salt, 35%) as a brown solid. $^1$H-NMR (400 MHz, DMSO-$d_6$) δ=10.52 (br. s., 1H), 8.42 (d, J=2.4 Hz, 1H), 8.33 (dd, J=2.6, 9.0 Hz, 1H), 7.87 (d, J=8.8 Hz, 1H), 7.40 (d, J=8.8 Hz, 2H), 7.13 (d, J=8.8 Hz, 2H), 4.19-4.13 (m, 2H), 3.49-3.37 (m, 2H), 3.13-3.05 (m, 2H), 2.36-2.08 (m, 7H), 1.99-1.90 (m, 2H), 1.69-1.61 (m, 1H), 1.41 (d, J=6.8 Hz, 3H); MS (ESI): [M+H$^+$]=504.1.

Example 3

3-(4-(3-(azepan-1-yl)propoxy)phenyl)-2-methyl-6-(pentafluorosulfanyl) quinazolin-4(3H)-one (III)

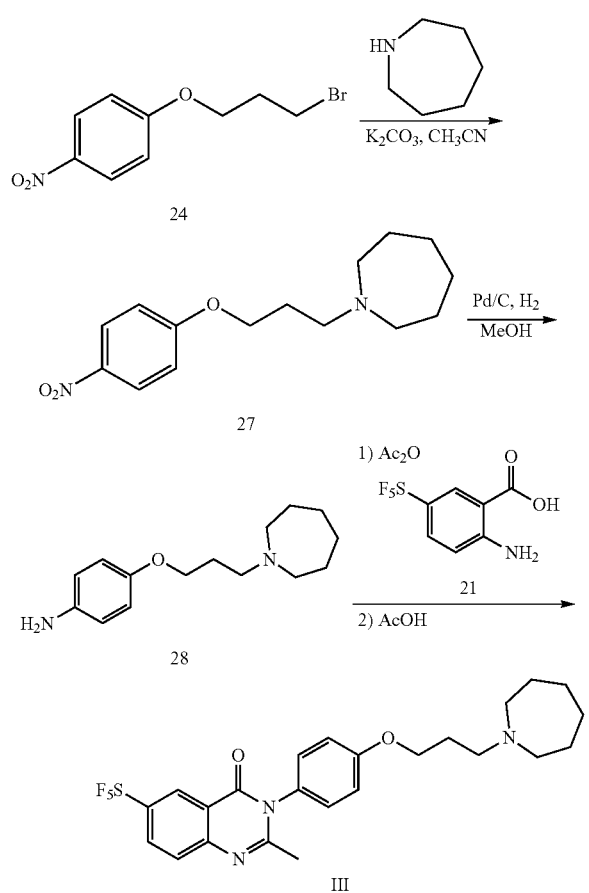

Step 1: 1-(3-(4-nitrophenoxy)propyl)azepane (27)

To a stirred suspension of 1-(3-bromopropoxy)-4-nitrobenzene (24) (260 mg, 1.0 mmol) in $CH_3CN$ (4 mL) were added $K_2CO_3$ (276 mg, 2.0 mmol) and azepane (198 mg, 2.0 mmol) at 25° C. The reaction was stirred at 80° C. for 16 h and then concentrated. The residue was partitioned between EA (10 mL) and water (5 mL). The organic phase was washed with brine (5 mL), dried over anhydrous $Na_2SO_4$, filtered and concentrated. The residue was purified by column chromatography (silica gel, DCM/MeOH=10:1) to afford the titled compound 27 (217 mg, 78%) as a yellow oil. MS (ESI): [M+H$^+$]=278.9.

Step 2: 4-(3-(azepan-1-yl)propoxy)aniline (28)

To a stirred suspension of 1-(3-(4-nitrophenoxy)propyl)azepane (27) (217 mg, 0.8 mmol) in MeOH (5 mL) was added Pd/C (20 mg, 10%) in one portion at 25° C. The reaction was stirred at 25° C. under $H_2$ atmosphere for 16 h. The resulting mixture was filtered through Celite®. The filtered cake was washed with MeOH (5 mL). The combined filtrate was concentrated to afford the titled compound 28 (193 mg, 100%) as a red oil. MS (ESI): [M+H$^+$]=248.9.

Step 3: 3-(4-(3-(azepan-1-yl)propoxy)phenyl)-2-methyl-6-(pentafluorosulfanyl) quinazolin-4(3H)-one (III)

A solution of 2-amino-5-(pentafluorosulfanyl)benzoic acid (21) (50 mg, 0.2 mmol) in $Ac_2O$ (1 mL) was heated under reflux for 4 h and then concentrated. To the residue were added 4-(3-(azepan-1-yl)propoxy)aniline (28) (57 mg, 0.2 mmol) and AcOH (1 mL) at 25° C. The reaction was stirred at 80° C. for 1 h and then concentrated. The residue was partitioned between EA (10 mL) and saturated aqueous $NaHCO_3$ solution (5 mL). The organic phase was washed with brine (5 mL), dried over anhydrous $Na_2SO_4$, filtered and concentrated. The residue was purified by prep-HPLC to afford the titled compound III (50 mg in HCl salt, 45%) as a brown solid. $^1$H-NMR (400 MHz, DMSO-$d_6$) δ=10.37 (br. s., 1H), 8.42 (d, J=2.4 Hz, 1H), 8.32 (dd, J=2.6, 9.0 Hz, 1H), 7.86 (d, J=8.8 Hz, 1H), 7.40 (d, J=8.8 Hz, 2H), 7.12 (d, J=8.8 Hz, 2H), 4.14 (t, J=5.8 Hz, 2H), 3.42-3.36 (m, 2H), 3.27-3.22 (m, 2H), 3.18-3.10 (m, 2H), 2.28-2.21 (in, 2H), 2.18 (s, 3H), 1.89-1.77 (m, 4H), 1.69-1.55 (in, 4H); MS (ESI): [M+H$^+$]=518.1.

Example 4

(R)-2-methyl-3-(4-(3-(2-methylpyrrolidin-1-yl)propoxy)phenyl)-6-(pentafluorosulfanyl)quinazolin-4(3H)-one (IV)

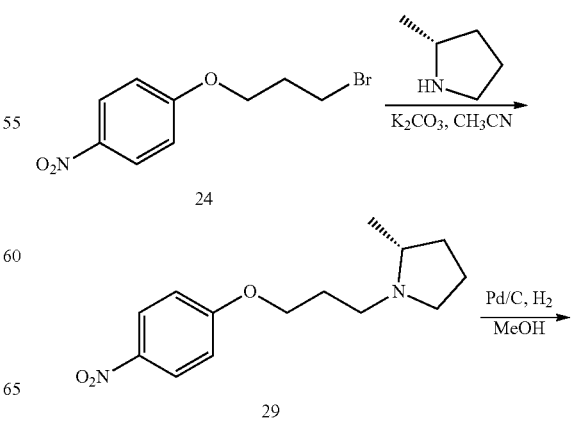

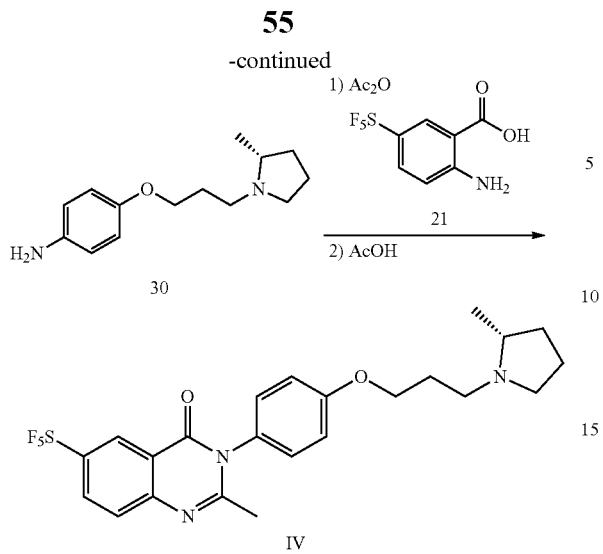

Step 1: (R)-2-methyl-1-(3-(4-nitrophenoxy)propyl) pyrrolidine (29)

To a stirred suspension of 1-(3-bromopropoxy)-4-nitrobenzene (24) (130 mg, 0.5 mmol) in CH$_3$CN (2 mL) were added K$_2$CO$_3$ (138 mg, 1.0 mmol) and (R)-2-methylpyrrolidine (85 mg, 1.0 mmol) at 25° C. The reaction was stirred at 80° C. for 16 h and then concentrated. The residue was partitioned between EA (10 mL) and water (5 mL). The organic phase was washed with brine (5 mL), dried over anhydrous Na$_2$SO$_4$, filtered and concentrated. The residue was purified by column chromatography (silica gel, DCM/MeOH=10:1) to afford the titled compound 29 (100 mg, 76%) as a yellow oil. MS (ESI): [M+H$^+$]=264.9.

Step 2: (R)-4-(3-(2-methylpyrrolidin-1-yl)propoxy) aniline (30)

To a stirred suspension of (R)-2-methyl-1-(3-(4-nitrophenoxy)propyl)pyrrolidine (29) (100 mg, 0.38 mmol) in MeOH (3 mL) was added Pd/C (10 mg, 10%) in one portion at 25° C. The reaction was stirred at 25° C. under H$_2$ atmosphere for 16 h and then filtered through Celite®. The filtered cake was washed with MeOH (3 mL). The combined filtrate was concentrated to afford the titled compound 30 (89 mg, crude) as a brown oil, which was used for the next step directly without further purification. MS (ESI): [M+H$^+$]=234.9.

Step 3: (R)-2-methyl-3-(4-(3-(2-methylpyrrolidin-1-yl)propoxy)phenyl)-6-(pentafluorosulfanyl)quinazolin-4(3H)-one (IV)

A solution of 2-amino-5-(pentafluorosulfanyl)benzoic acid (21) (50 mg, 0.2 mmol) in Ac$_2$O (1 mL) was heated under reflux for 4 h and then concentrated. To the residue were added (R)-4-(3-(2-methylpyrrolidin-1-yl)propoxy)aniline (30) (89 mg, 0.4 mmol) and AcOH (1 mL) at 25° C. The reaction was stirred at 80° C. for 1 h. After that, the resulting mixture was concentrated. The residue was partitioned between EA (10 mL) and saturated aqueous NaHCO$_3$ solution (5 mL). The organic phase was washed with brine (5 mL), dried over anhydrous Na$_2$SO$_4$, filtered and concentrated. The residue was purified by prep-HPLC to afford the titled compound IV (50 mg in HCl salt, 43%) as a brown solid. $^1$H]NMR (400 MHz, DMSO-d$_6$) δ=10.50 (br. s., 1H), 8.42 (d, J=2.4 Hz, 1H), 8.32 (dd, J=2.4, 9.2 Hz, 1H), 7.86 (d, J=9.2 Hz, 1H), 7.40 (d, J=8.8 Hz, 2H), 7.13 (d, J=8.8 Hz, 2H), 4.16 (br. s., 2H), 3.67-3.60 (m, 2H), 3.48-3.36 (m, 2H), 3.16-3.00 (m, 2H), 2.23-2.16 (m, 5H), 2.04-1.87 (m, 2H), 1.67-1.62 (m, 1H), 1.41 (d, J=6.4 Hz, 3H); MS (ESI): [M+H$^+$]=504.0.

Example 5

(S)-2-methyl-3-(4-(3-(3-methylpiperidin-1-yl) propoxy)phenyl)-6-(pentafluorosulfanyl)quinazolin-4(3H)-one (V)

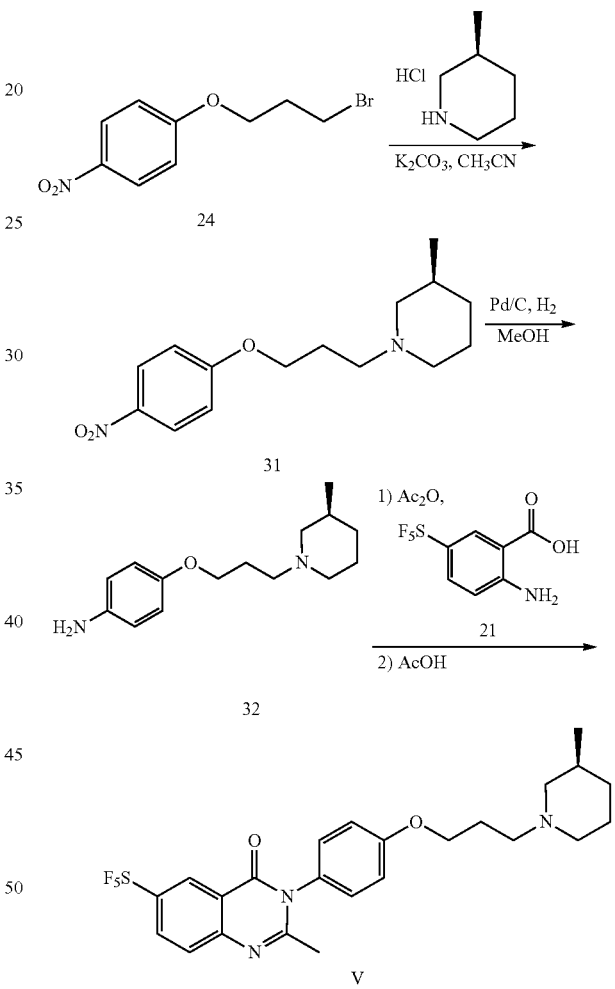

Step 1: (S)-3-methyl-1-(3-(4-nitrophenoxy)propyl) piperidine (31)

To a stirred suspension of 1-(3-bromopropoxy)-4-nitrobenzene (24) (260 mg, 1.0 mmol) in CH$_3$CN (6 mL) were added K$_2$CO$_3$ (552 mg, 4.0 mmol) and (S)-3-methylpiperidine hydrochloride (270 mg, 2.0 mmol) at 25° C. The reaction was stirred at 80° C. for 16 h and then concentrated. The residue was partitioned between EA (20 mL) and water (10 mL). The organic phase was washed with brine (10 mL), dried over anhydrous Na$_2$SO$_4$, filtered and concentrated.

The residue was purified by column chromatography (silica gel, DCM/MeOH=10:1) to afford the titled compound 31 (248 mg, 89%) as a yellow oil. MS (ESI): [M+H$^+$]=278.9.

Step 2: (S)-4-(3-(3-methylpiperidin-1-yl)propoxy)aniline (32)

To a stirred suspension of (S)-3-methyl-1-(3-(4-nitrophenoxy)propyl)piperidine (31) (248 mg, 0.9 mmol) in MeOH (5 mL) was added palladium on carbon (25 mg, 10%) in one portion at 25° C. The reaction was stirred at 25° C. under H$_2$ atmosphere for 16 h and then filtered through Celite®. The filtered cake was washed with MeOH (5 mL). The combined filtrate was concentrated to afford the titled compound 32 (221 mg, 100%) as a red oil. MS (ESI): [M+H$^+$]=248.9.

Step 3: (S)-2-methyl-3-(4-(3-(3-methylpiperidin-1-yl)propoxy)phenyl)-6-(pentafluorosulfanyl)quinazolin-4(3H)-one (V)

A solution of 2-amino-5-(pentafluorosulfanyl)benzoic acid (21) (50 mg, 0.2 mmol) in Ac$_2$O (1 mL) was heated under reflux for 4 h and then concentrated. To the residue were added (S)-4-(3-(3-methylpiperidin-1-yl)propoxy)aniline (32) (57 mg, 0.23 mmol) and AcOH (1 mL) at 25° C. The reaction was stirred at 80° C. for 1 h. After that, the resulting mixture was concentrated. The residue was partitioned between EA (10 mL) and saturated aqueous NaHCO$_3$ solution (5 mL). The organic phase was washed with brine (5 mL), dried over anhydrous Na$_2$SO$_4$, filtered and concentrated. The residue was purified by prep-HPLC to afford the titled compound V (50 mg in HCl salt, 45%) as a brown solid. $^1$H\NMR (400 MHz, DMSO-d$_6$) δ=10.36 (br. s., 1H), 8.42 (d, J=2.4 Hz, 1H), 8.32 (dd, J=2.6, 9.0 Hz, 1H), 7.86 (d, J=8.8 Hz, 1H), 7.40 (d, J=8.8 Hz, 2H), 7.12 (d, J=8.8 Hz, 2H), 4.14 (t, J=5.8 Hz, 2H), 3.50-3.39 (m, 2H), 3.22-3.14 (m, 2H), 2.83-2.75 (m, 1H), 2.60-2.52 (m, 1H), 2.31-2.21 (m, 2H), 2.18 (s, 3H), 1.98-1.73 (m, 5H), 0.90 (d, J=6.8 Hz, 3H); MS (ESI): [M+H$^+$]=518.1.

Example 6

3-(2-methoxy-4-(3-(pyrrolidin-1-yl)propoxy)phenyl)-2-methyl-6-(pentafluorosulfanyl)quinazolin-4(3H)-one (VI)

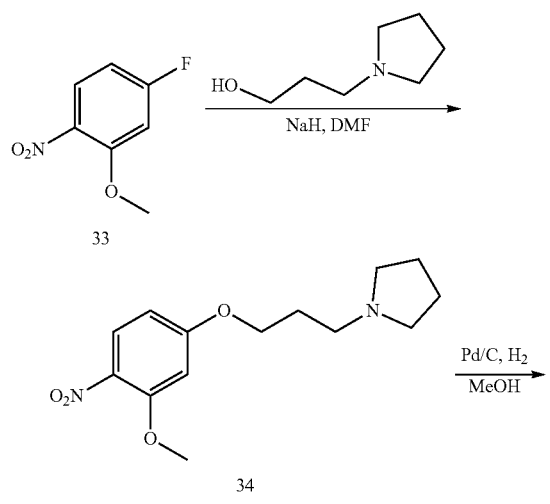

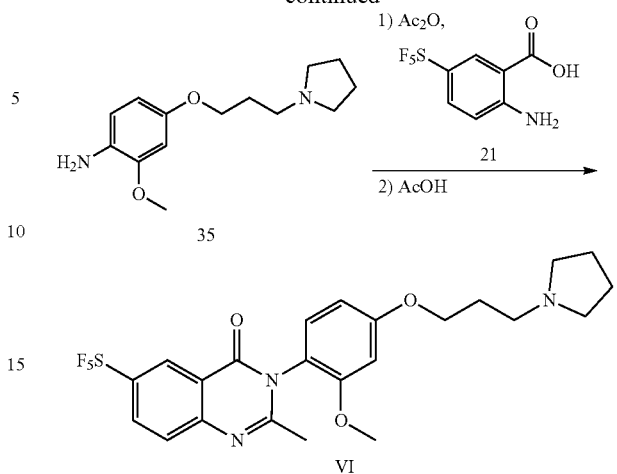

Step 1: 1-(3-(3-methoxy-4-nitrophenoxy)propyl)pyrrolidine (34)

To a stirred solution of 3-(pyrrolidin-1-yl)propan-1-ol (142 mg, 1.1 mmol) in DMF (3 mL) was added NaH (48 mg, 1.2 mmol, 60% in mineral oil) at 0° C. The reaction was stirred at 0° C. for 30 min and followed by addition of 4-fluoro-2-methoxy-1-nitrobenzene (33) (171 mg, 1.0 mmol). The reaction mixture was stirred at 0° C.-25° C. for 16 h. The resulting mixture was diluted with EA (10 mL) and water (3 mL). The organic phase was washed with brine (3 mL), dried over anhydrous Na$_2$SO$_4$, filtered and concentrated. The residue was purified by column chromatography (silica gel, PE/EA=1:1 and DCM/MeOH=10:1) to afford the titled compound 34 (200 mg, 71%) as a yellow oil. MS (ESI): [M+H$^+$]=280.9.

Step 2: 2-methoxy-4-(3-(pyrrolidin-1-yl)propoxy)aniline (35)

To a stirred suspension of 1-(3-(3-methoxy-4-nitrophenoxy)propyl)pyrrolidine (34) (200 mg, 0.7 mmol) in MeOH (5 mL) was added Pd/C (20 mg, 10%) in one portion at 25° C. The reaction was stirred at 25° C. under H$_2$ atmosphere for 16 h and then filtered through Celite®. The filtered cake was washed with MeOH (5 mL). The combined filtrate was concentrated to afford the titled compound 35 (178 mg, 100%) as a red oil. MS (ESI): [M+H$^+$]=250.9.

Step 3: 3-(2-methoxy-4-(3-(pyrrolidin-1-yl)propoxy)phenyl)-2-methyl-6-(pentafluorosulfanyl)quinazolin-4(3H)-one (VI)

A solution of 2-amino-5-(pentafluorosulfanyl)benzoic acid (21) (50 mg, 0.2 mmol) in Ac$_2$O (1 mL) was heated under reflux for 4 h and then concentrated. To the residue were added 2-methoxy-4-(3-(pyrrolidin-1-yl)propoxy)aniline (35) (57 mg, 0.2 mmol) and AcOH (1 mL) at 25° C. The reaction was stirred at 80° C. for 1 h. After that, the resulting mixture was concentrated. The residue was partitioned between EA (10 mL) and saturated aqueous NaHCO$_3$ solution (5 mL). The organic phase was washed with brine (5 mL), dried over anhydrous Na$_2$SO$_4$, filtered and concentrated. The residue was purified by prep-HPLC to afford the titled compound VI (50 mg in HCl salt, 45%) as a brown solid. $^1$H[NMR (400 MHz, DMSO-d$_6$) δ=10.94 (br. s., 1H), 8.41 (d, J=2.8 Hz, 1H), 8.32 (dd, J=2.6, 9.0 Hz, 1H), 7.85 (d, J=9.2 Hz, 1H), 7.34 (d, J=8.8 Hz, 1H), 6.81 (d, J=2.4 Hz, 1H), 6.71 (dd, J=2.2, 8.6 Hz, 1H), 4.18 (t, J=5.8 Hz, 2H), 3.75 (s, 3H), 3.59-3.53 (m, 2H), 3.33-3.26 (m, 2H), 3.05-2.96 (m, 2H), 2.25-2.18 (m, 2H), 2.16 (s, 3H), 2.04-1.97 (m, 2H), 1.94-1.83 (m, 2H); MS (ESI): [M+H$^+$]=520.0.

Example 7

2-methyl-3-(4-(3-(3-methylpyrrolidin-1-yl)propoxy)phenyl)-6-(pentafluorosulfanyl)quinazolin-4(3H)-one (VII)

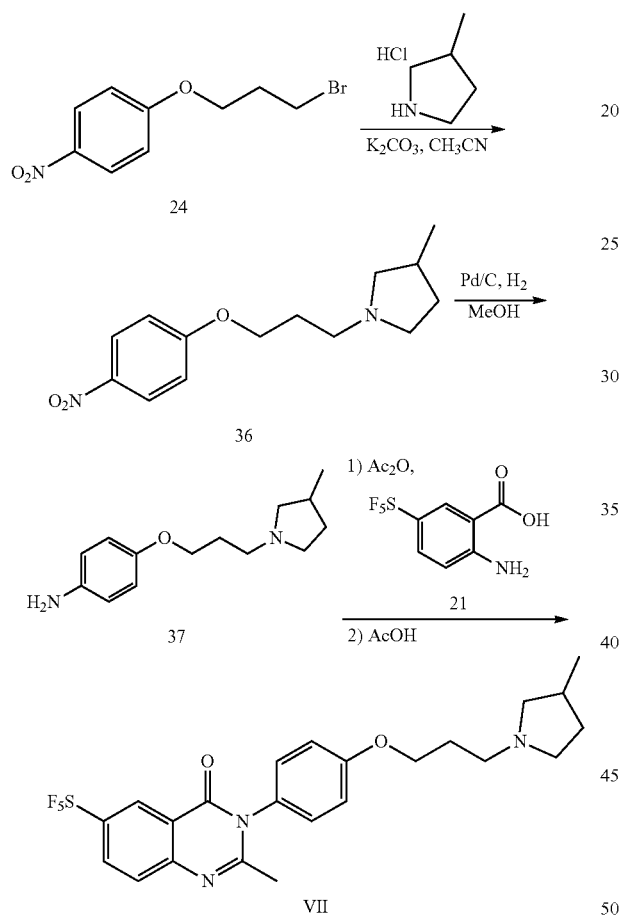

Step 1: 3-methyl-1-(3-(4-nitrophenoxy)propyl)pyrrolidine (36)

To a stirred suspension of 1-(3-bromopropoxy)-4-nitrobenzene (24) (130 mg, 0.5 mmol) in CH$_3$CN (3 mL) was added K$_2$CO$_3$ (207 mg, 1.5 mmol) and 3-methylpyrrolidine hydrochloride (122 mg, 1.0 mmol) at 25° C. The reaction was stirred at 80° C. for 16 h and then concentrated. The residue was partitioned between EA (10 mL) and water (5 mL). The organic phase was washed with brine (5 mL), dried over anhydrous Na$_2$SO$_4$, filtered and concentrated. The residue was purified by column chromatography (silica gel, DCM/MeOH=10:1) to afford the titled compound 36 (110 mg, 83%) as a yellow oil. MS (ESI): [M+H$^+$]=264.9.

Step 2: 4-(3-(3-methylpyrrolidin-1-yl)propoxy)aniline (37)

To a stirred suspension of 3-methyl-1-(3-(4-nitrophenoxy)propyl)pyrrolidine (36) (110 mg, 0.4 mmol) in MeOH (3 mL) was added Pd/C (10 mg, 10%) in one portion at 25° C. The reaction was stirred at 25° C. under H$_2$ atmosphere for 16 h and then filtered through Celite®. The filtered cake was washed with MeOH (3 mL). The combined filtrate was concentrated to afford the titled compound 37 (98 mg, crude) as a brown oil, which was used for the next step directly without further purification. MS (ESI): [M+H$^+$]=234.9.

Step 3: 2-methyl-3-(4-(3-(3-methylpyrrolidin-1-yl)propoxy)phenyl)-6-(pentafluorosulfanyl)quinazolin-4(3H)-one (VII)

A solution of 2-amino-5-(pentafluorosulfanyl)benzoic acid (21) (50 mg, 0.19 mmol) in Ac$_2$O (1 mL) was heated under reflux for 4 h and then concentrated. To the residue were added 4-(3-(3-methylpyrrolidin-1-yl)propoxy)aniline (37) (89 mg, 0.38 mmol) and AcOH (1 mL) at 25° C. The reaction was stirred at 80° C. for 1 h. After that, the resulting mixture was concentrated. The residue was partitioned between EA (10 mL) and saturated aqueous NaHCO$_3$ solution (5 mL). The organic phase was washed with brine (5 mL), dried over anhydrous Na$_2$SO$_4$, filtered and concentrated. The residue was purified by prep-HPLC to afford the titled compound VII (57 mg in HCl salt, 56%) as a brown solid. $^1$H[NMR (400 MHz, DMSO-d$_6$) δ=10.97 (br. s., 1H), 8.42 (d, J=2.4 Hz, 1H), 8.32 (dd, J=2.4, 9.2 Hz, 1H), 7.86 (d, J=9.2 Hz, 1H), 7.40 (d, J=8.8 Hz, 2H), 7.12 (d, J=9.2 Hz, 2H), 4.15 (t, J=6.0 Hz, 2H), 3.67-3.51 (m, 1.5H), 3.33-3.00 (m, 4H), 2.67-2.57 (m, 0.5H), 2.38-2.04 (m, 7H), 1.68-1.46 (m, 1H), 1.07 (dd, J=2.6, 6.6 Hz, 3H); MS (ESI): [M+H$^+$]=504.0.

Example 8

3-(2-hydroxy-4-(3-(pyrrolidin-1-yl)propoxy)phenyl)-2-methyl-6-(pentafluoro-λ6-sulfaneyl)quinazolin-4(3H)-one (VIII)

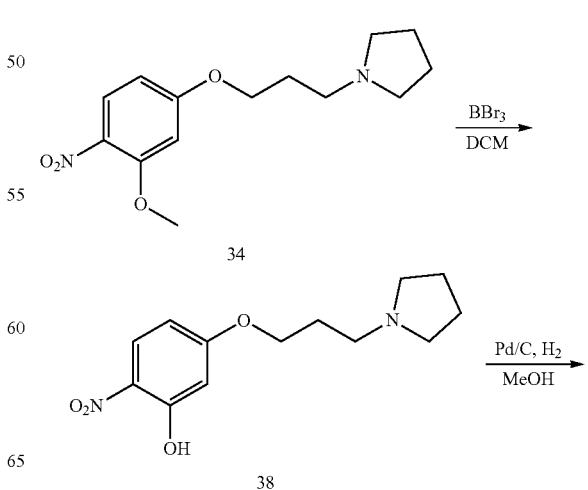

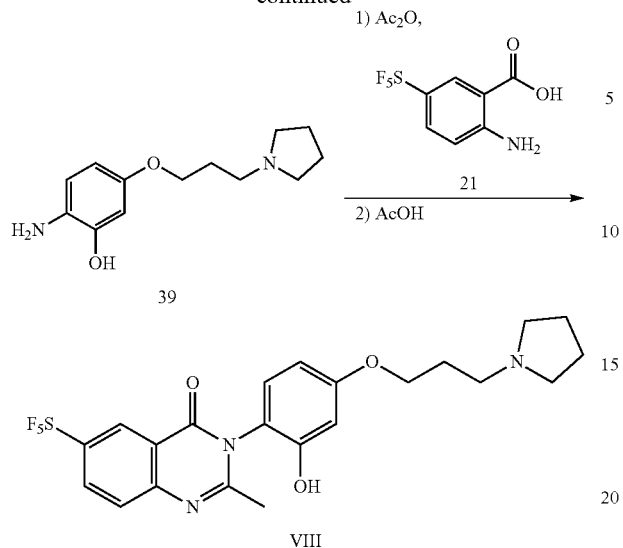

Step 1: 2-nitro-5-(3-(pyrrolidin-1-yl)propoxy)phenol (38)

To a stirred solution of 1-(3-(3-methoxy-4-nitrophenoxy)propyl)pyrrolidine (34) (0.7 g, 2.5 mmol) in DCM (10 mL) was added BBr$_3$ (1.9 g, 7.5 mmol) dropwise at −78° C. The reaction was stirred for 4 h and gradually was allowed to warm up to 0° C. The reaction mixture was quenched with MeOH (10 mL) at −10° C. and then diluted with saturated aqueous NaHCO$_3$ solution (20 mL). The resulting mixture was extracted with EA (2×20 mL). The combined organic phase was washed with brine (30 mL), dried with anhydrous Na$_2$SO$_4$, filtered and concentrated. The residue was purified by prep-HPLC to afford the titled compound 38 (90 mg, 14%) as an off-white solid. $^1$H[NMR (400 MHz, CD$_3$OD) δ=8.09 (d, J=9.2 Hz, 1H), 6.72-6.58 (m, 2H), 4.21 (t, J=5.6 Hz, 2H), 3.79-3.64 (m, 2H), 3.47-3.36 (m, 2H), 3.21-3.06 (m, 2H), 2.34-2.13 (m, 4H), 2.11-1.96 (m, 2H); MS (ESI): [M+H]$^+$=266.9.

Step 2: 2-amino-5-(3-(pyrrolidin-1-yl)propoxy)phenol (39)

To a stirred solution of 2-nitro-5-(3-(pyrrolidin-1-yl)propoxy)phenol (38) (90 mg, 0.34 mmol) in MeOH (1 mL) was added Pd/C (10 mg, 10%). The reaction was stirred under H$_2$ atmosphere at 25° C. for 16 h and then filtered. The filtrate was concentrated to afford the titled compound 39 (80 mg, crude) as an off-white oil, which was used for next step without further purification. MS (ESI): [M+H]$^+$=236.9.

Step 3: 3-(2-hydroxy-4-(3-(pyrrolidin-1-yl)propoxy)phenyl)-2-methyl-6-(pentafluoro-λ6-sulfaneyl)quinazolin-4(3H)-one (VIII)

A solution of 2-amino-5-(pentafluorosulfanyl)benzoic acid (21) (50 mg, 0.2 mmol) in Ac$_2$O (1 mL) was heated under reflux for 2 h and then concentrated. To the residue were added 2-amino-5-(3-(pyrrolidin-1-yl)propoxy)phenol (39) (54 mg, 0.2 mmol) and AcOH (1 mL). The reaction was stirred at 80° C. for 1 h and then concentrated. The residue was purified by prep-HPLC to afford the titled compound VIII (25 mg, 26%) as an off-white solid. $^1$H-NMR (400 MHz, CD$_3$OD) δ=8.66 (d, J=2.0 Hz, 1H), 8.42 (d, J=9.2 Hz, 1H), 7.92 (d, J=9.2 Hz, 1H), 7.24 (d, J=8.4 Hz, 1H), 6.76-6.59 (m, 2H), 4.26-4.10 (m, 2H), 3.83-3.65 (m, 2H), 3.54-3.38 (m, 2H), 3.23-3.06 (m, 2H), 2.52 (s, 3H), 2.38-2.14 (m, 4H), 2.13-1.97 (m, 3H); MS (ESI): [M+H]$^+$=506.0.

Example 9

(S)-3-(2-methoxy-4-(3-(3-methylpiperidin-1-yl)propoxy)phenyl)-2-methyl-6-(pentafluorosulfanyl)quinazolin-4(3H)-one (IX)

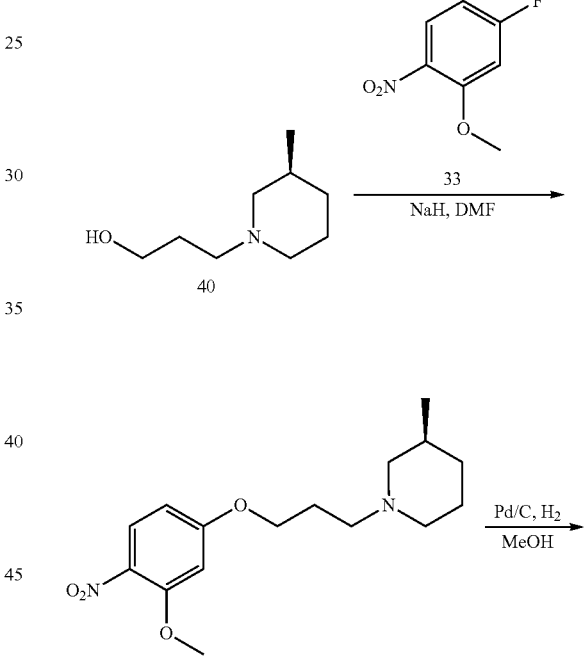

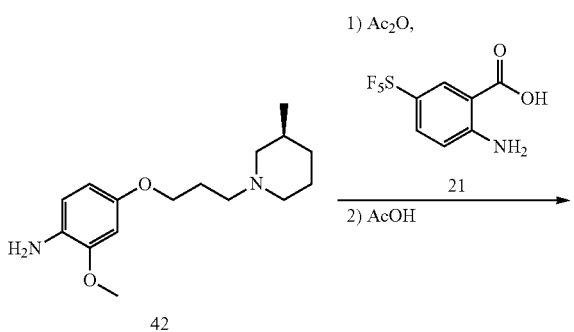

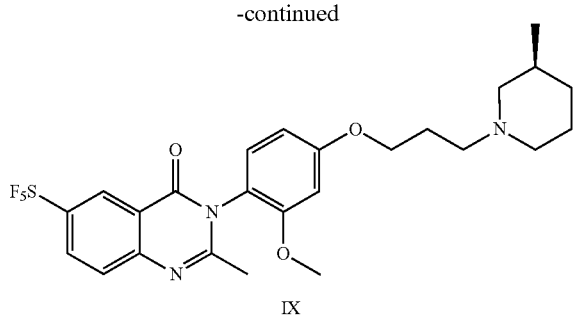

IX

Step 1: (S)-3-(3-methylpiperidin-1-yl)propan-1-ol (40)

To a stirred suspension of 3-bromopropan-1-ol (300 mg, 2.2 mmol) in THF (10 mL) were added $K_2CO_3$ (1191 mg, 8.6 mmol) and (S)-3-methylpiperidine hydrochloride (587 mg, 4.3 mmol) at 0° C. The reaction was stirred at 0° C.-25° C. for 16 h. The resulting mixture was diluted with EA (15 mL) and filtered through Celite®. The filtered cake was washed with EA (10 mL). The combined filtrate was washed with water (10 mL) and brine (10 mL), dried over anhydrous $Na_2SO_4$, filtered and concentrated to afford the titled compound 40 (350 mg, crude) as a colorless oil, which was used for the next step without further purification.

Step 2: (S)-1-(3-(3-methoxy-4-nitrophenoxy)propyl)-3-methylpiperidine (41)

To a stirred solution of (S)-3-(3-methylpiperidin-1-yl)propan-1-ol (40) (350 mg, 2.2 mmol) in DMF (4 mL) was added NaH (97 mg, 2.4 mmol, 60% in mineral oil) at 0° C. The reaction was stirred at 0° C. for 0.5 h and followed by the addition of 4-fluoro-2-methoxy-1-nitrobenzene (33) (347 mg, 2.0 mmol). The reaction mixture was stirred at 0-25° C. for 16 h. The resulting mixture was diluted with EA (30 mL) and water (5 mL). The organic phase was washed with brine (5 mL), dried over anhydrous $Na_2SO_4$, filtered and concentrated. The residue was purified by column chromatography (silica gel, PE/EA=1:1 and DCM/MeOH=10:1) to afford the titled compound 41 (300 mg, 45% for two steps) as a yellow oil. MS (ESI): [M+H$^+$]= 308.9.

Step 3: (S)-2-methoxy-4-(3-(3-methylpiperidin-1-yl)propoxy)aniline (42)

To a stirred suspension of (S)-1-(3-(3-methoxy-4-nitrophenoxy)propyl)-3-methylpiperidine (41) (300 mg, 1.0 mmol) in MeOH (4 mL) was added Pd/C (30 mg, 10%) in one portion at 25° C. The reaction was stirred at 25° C. under $H_2$ atmosphere for 16 h and then filtered through Celite®. The filtered cake was washed with MeOH (5 mL). The combined filtrate was concentrated to afford the titled compound 42 (270 mg, crude) as a black oil, which was used for the next step without further purification. MS (ESI): [M+H$^+$]=278.9.

Step 4: (S)-3-(2-methoxy-4-(3-(3-methylpiperidin-1-yl)propoxy)phenyl)-2-methyl-6-(pentafluorosulfanyl)quinazolin-4(3H)-one (IX)

A solution of 2-amino-5-(pentafluorosulfanyl)benzoic acid (21) (50 mg, 0.2 mmol) in $Ac_2O$ (1 mL) was heated under reflux for 4 h and then concentrated. To the residue were added (S)-2-methoxy-4-(3-(3-methylpiperidin-1-yl)propoxy)aniline (42) (64 mg, 0.23 mmol) and AcOH (1 mL) at 25° C. The reaction was stirred at 80° C. for 1 h. After that, the resulting mixture was concentrated. The residue was partitioned between EA (10 mL) and saturated aqueous $NaHCO_3$ solution (5 mL). The organic phase was washed with brine (5 mL), dried over anhydrous $Na_2SO_4$, filtered and concentrated. The residue was purified by prep-HPLC to afford the titled compound IX (40 mg in HCl salt, 30%) as an off-white solid. $^1$H-NMR (400 MHz, DMSO-d$_6$) δ=10.54 (br. s., 1H), 8.42 (d, J=2.4 Hz, 1H), 8.32 (dd, J=2.2, 9.0 Hz, 1H), 7.85 (d, J=9.2 Hz, 1H), 7.34 (d, J=8.8 Hz, 1H), 6.80 (d, J=2.0 Hz, 1H), 6.71 (dd, J=2.0, 8.8 Hz, 1H), 4.17 (t, J=5.6 Hz, 2H), 3.75 (s, 3H), 3.49-3.38 (m, 2H), 3.23-3.13 (m, 2H), 2.88-2.71 (m, 1H), 2.59-2.52 (m, 1H), 2.32-2.21 (m, 2H), 2.16 (s, 3H), 2.07-1.95 (m, 1H), 1.88-1.73 (m, 3H), 1.12-1.03 (m, 1H), 0.90 (d, J=6.8 Hz, 3H); MS (ESI): [M+H$^+$]= 548.1.

Example 10

(R)-3-(2-methoxy-4-(3-(2-methylpyrrolidin-1-yl)propoxy)phenyl)-2-methyl-6-(pentafluorosulfanyl)quinazolin-4(3H)-one (X)

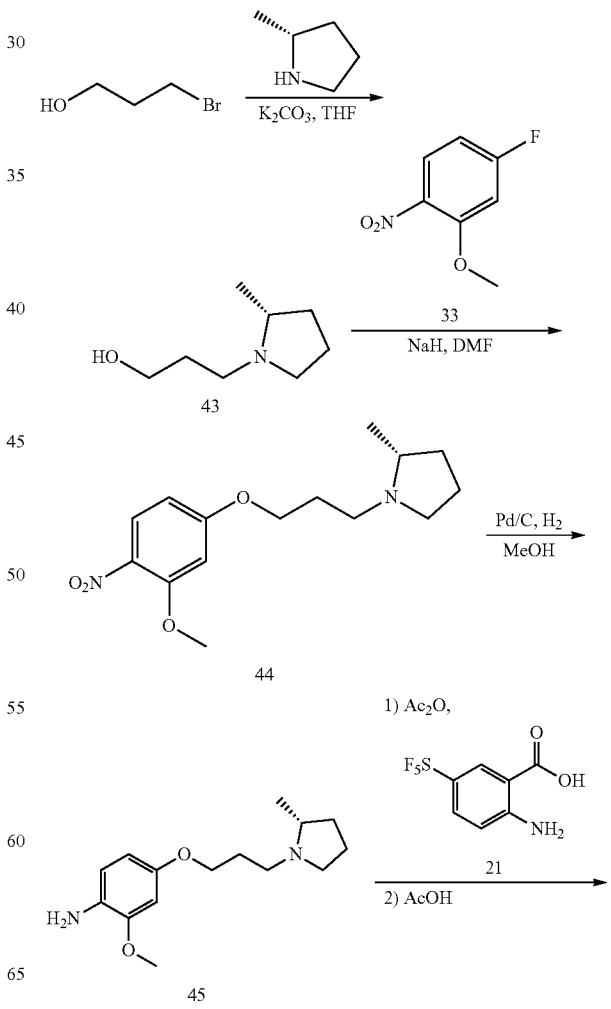

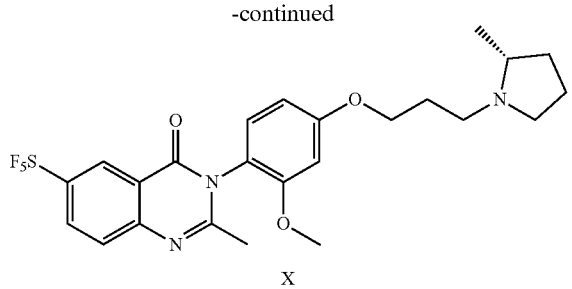

X

Step 1: (R)-3-(2-methylpyrrolidin-1-yl)propan-1-ol (43)

To a stirred suspension of 3-bromopropan-1-ol (192 mg, 1.4 mmol) in THF (3 mL) was added $K_2CO_3$ (381 mg, 2.8 mmol) and (R)-2-methylpyrrolidine (43) (200 mg, 2.4 mmol) at 0° C. The reaction was stirred at 0-25° C. for 16 h. The resulting mixture was diluted with EA (5 mL) and filtered through Celite®. The filtered cake was washed with EA (5 mL). The combined filtrate was washed with water (5 mL) and brine (5 mL), dried over anhydrous $Na_2SO_4$, filtered and concentrated to afford the titled compound 44 (127 mg, 64%) as a yellow oil, which was used for the next step without further purification.

Step 2: (R)-1-(3-(3-methoxy-4-nitrophenoxy)propyl)-2-methylpyrrolidine (44)

To a stirred solution of (R)-3-(2-methylpyrrolidin-1-yl)propan-1-ol (43) (127 mg, 0.9 mmol) in DMF (2 mL) was added NaH (39 mg, 1.0 mmol, 60% in mineral oil) at 0° C. The reaction was stirred at 0° C. for 30 min and followed by the addition of 4-fluoro-2-methoxy-1-nitrobenzene (33) (138 mg, 0.8 mmol). The reaction mixture was stirred at 0° C.-25° C. for 16 h. The resulting mixture was diluted with EA (10 mL) and water (2 mL). The organic phase was washed with brine (2 mL), dried over anhydrous $Na_2SO_4$, filtered and concentrated. The residue was purified by column chromatography (silica gel, PE/EA=1:1 and DCM/MeOH=10:1) to afford the titled compound 44 (81 mg, 34%, two steps) as a yellow oil. MS (ESI): $[M+H^+]=294.9$.

Step 3: (R)-2-methoxy-4-(3-(2-methylpyrrolidin-1-yl)propoxy)aniline (45)

To a stirred suspension of (R)-1-(3-(3-methoxy-4-nitrophenoxy)propyl)-2-methylpyrrolidine (44) (81 mg, 0.3 mmol) in MeOH (1 mL) was added Pd/C (8 mg, 10%) in one portion at 25° C. The reaction was stirred at 25° C. under $H_2$ atmosphere for 16 h and then filtered through Celite®. The filtered cake was washed with MeOH (5 mL). The combined filtrate was concentrated to afford the titled compound 45 (73 mg, crude) as a violet oil which was used for the next step without further purification. MS (ESI): $[M+H^+]=264.9$.

Step 4: (R)-3-(2-methoxy-4-(3-(2-methylpyrrolidin-1-yl)propoxy)phenyl)-2-methyl-6-(pentafluorosulfanyl)quinazolin-4(3H)-one (X)

A solution of 2-amino-5-(pentafluorosulfanyl)benzoic acid (21) (50 mg, 0.2 mmol) in $Ac_2O$ (1 mL) was heated to reflux for 4 h and then concentrated. To the residue were added (R)-2-methoxy-4-(3-(2-methylpyrrolidin-1-yl) propoxy)aniline (45) (61 mg, 0.2 mmol) and AcOH (1 mL) 25° C. The reaction was stirred at 80° C. for 1 h. After that, the resulting mixture was concentrated. The residue was partitioned between EA (10 mL) and saturated aqueous $NaHCO_3$ solution (5 mL). The aqueous phase was separated. The organic phase was washed with brine (5 mL), dried over anhydrous $Na_2SO_4$, filtered and concentrated. The residue was purified by prep-HPLC to afford the titled compound X (30 mg in HCl salt, 23%) as a brown solid. $^1$H-NMR (400 MHz, DMSO-$d_6$) δ=10.74 (br. s., 1H), 8.41 (d, J=2.4 Hz, 1H), 8.33 (dd, J=2.2, 9.0 Hz, 1H), 7.86 (d, J=9.2 Hz, 1H), 7.34 (d, J=8.4 Hz, 1H), 6.82 (s, 1H), 6.72 (dd, J=1.6, 8.8 Hz, 1H), 4.19 (br. s., 2H), 3.75 (s, 3H), 3.65-3.58 (m, 1H), 3.50-3.34 (m, 2H), 3.13-3.02 (m, 2H), 2.31-2.17 (m, 3H), 2.17 (s, 3H), 2.01-1.90 (m, 2H), 1.72-1.60 (m, 1H), 1.42 (d, J=6.0 Hz, 3H); MS (ESI): $[M+H^+]=534.1$.

Example 11

3-(3-methoxy-4-(3-(pyrrolidin-1-yl)propoxy)phenyl)-2-methyl-6-(pentafluorosulfanyl)quinazolin-4(3H)-one (XI)

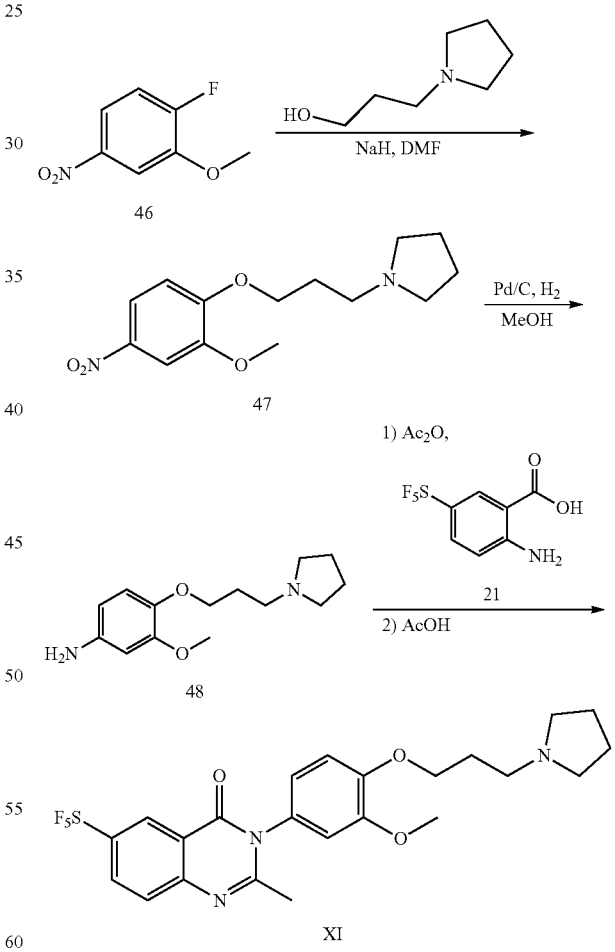

Step 1: 1-(3-(2-methoxy-4-nitrophenoxy)propyl)pyrrolidine (47)

To a stirred solution of 3-(pyrrolidin-1-yl)propan-1-ol (142 mg, 1.1 mmol) in DMF (3 mL) was added NaH (48 mg, 1.2 mmol, 60% in mineral oil) at 0° C. The reaction was stirred at 0° C. for 0.5 h and then followed by addition of 1-fluoro-2-methoxy-4-nitrobenzene (46) (171 mg, 1.0 mmol). The reaction was stirred at 0° C.-25° C. for 16 h. The resulting mixture was diluted with EA (10 mL) and water (3 mL). The organic phase was washed with brine (3 mL), dried over anhydrous Na$_2$SO$_4$, filtered and concentrated. The residue was purified by column chromatography (silica gel, PE/EA=1:1 and DCM/MeOH=10:1) to afford the titled compound 47 (170 mg, 61%) as a yellow oil. MS (ESI): [M+H$^+$]=280.9.

Step 2: 3-methoxy-4-(3-(pyrrolidin-1-yl)propoxy) aniline (48)

To a stirred suspension of 1-(3-(2-methoxy-4-nitrophenoxy)propyl)pyrrolidine (47) (170 mg, 0.6 mmol) in MeOH (5 mL) was added Pd/C (20 mg, 10%) in one portion at 25° C. The reaction was stirred at 25° C. under H$_2$ atmosphere for 16 h and then filtered through Celite®. The filtered cake was washed with MeOH (5 mL). The combined filtrate was concentrated to afford the titled compound 48 (152 mg, 100%) as a red oil. MS (ESI): [M+H$^+$]=250.9.

Step 3: 3-(3-methoxy-4-(3-(pyrrolidin-1-yl)propoxy) phenyl)-2-methyl-6-(pentafluorosulfanyl)quinazolin-4(3H)-one (XI)

A solution of 2-amino-5-(pentafluorosulfanyl)benzoic acid (21) (50 mg, 0.2 mmol) in Ac$_2$O (1 mL) was heated to reflux for 4 h and then concentrated. To the residue were added 3-methoxy-4-(3-(pyrrolidin-1-yl)propoxy)aniline (48) (57 mg, 0.2 mmol) and AcOH (1 mL) at 25° C. The reaction was stirred at 80° C. for 1 h. After that, the resulting mixture was concentrated. The residue was partitioned between EA (10 mL) and saturated aqueous NaHCO$_3$ solution (5 mL). The organic phase was washed with brine (5 mL), dried over anhydrous Na$_2$SO$_4$, filtered and concentrated. The residue was purified by prep-HPLC to afford the titled compound XI (50 mg in HCl salt, 40%) as a brown solid. $^1$H-NMR (400 MHz, DMSO-d$_6$) δ=10.55 (br. s., 1H), 8.43 (d, J=2.4 Hz, 1H), 8.32 (dd, J=2.6, 9.0 Hz, 1H), 7.86 (d, J=9.2 Hz, 1H), 7.18-7.11 (m, 2H), 7.00 (dd, J=2.2, 8.6 Hz, 1H), 4.14 (t, J=5.8 Hz, 2H), 3.76 (s, 3H), 3.63-3.58 (m, 2H), 3.32-3.26 (m, 2H), 3.06-2.98 (m, 2H), 2.23 (s, 3H), 2.21-2.14 (m, 2H), 2.05-1.97 (m, 2H), 1.93-1.85 (m, 2H); MS (ESI): [M+H$^+$]=520.0.

Example 12

3-(2-methoxy-4-(3-(3-methylpyrrolidin-1-yl) propoxy)phenyl)-2-methyl-6-(pentafluorosulfanyl) quinazolin-4(3H)-one (XII)

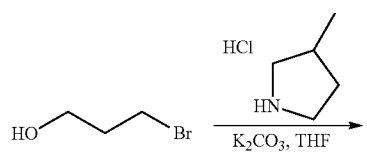

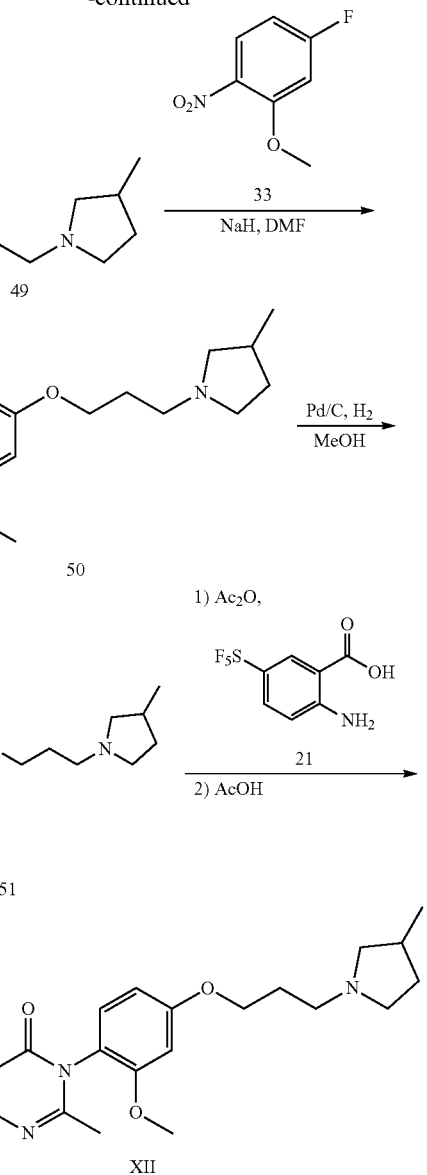

Step 1: 3-(3-methylpyrrolidin-1-yl)propan-1-ol (49)

To a stirred suspension of 3-bromopropan-1-ol (134 mg, 1.0 mmol) in THF (3 mL) were added K$_2$CO$_3$ (532 mg, 3.9 mmol) and 3-methylpyrrolidine hydrochloride (200 mg, 1.6 mmol) at 0° C. The reaction was stirred at 0° C.-25° C. for 16 h. The resulting mixture was diluted with EA (5 mL), filtered through Celite®. The filtered cake was washed with EA (5 mL). The combined filtrate was washed with water (5 mL) and brine (5 mL), dried over anhydrous Na$_2$SO$_4$, filtered and concentrated to afford the titled compound 49 (86 mg, 62%) as a yellow oil.

Step 2: 1-(3-(3-methoxy-4-nitrophenoxy)propyl)-3-methylpyrrolidine (50)

To a stirred solution of 3-(3-methylpyrrolidin-1-yl)propan-1-ol (49) (86 mg, 0.6 mmol) in DMF (2 mL) was added NaH (26 mg, 0.7 mmol, 60% in mineral oil) at 0° C. The reaction was stirred at 0° C. for 30 min and followed by the addition of 4-fluoro-2-methoxy-1-nitrobenzene (33) (93 mg, 0.6 mmol). The reaction mixture was stirred at 0° C.-25° C. for 16 h. The resulting mixture was diluted with EA (10 mL) and water (2 mL). The organic phase was washed with brine (2 mL), dried over anhydrous $Na_2SO_4$, filtered and concentrated. The residue was purified by column chromatography (silica gel, PE/EA=1:1 and DCM/MeOH=10:1) to afford the titled compound 50 (38 mg, 21%) as a yellow oil. MS (ESI): $[M+H^+]$=294.9.

Step 3: 2-methoxy-4-(3-(3-methylpyrrolidin-1-yl)propoxy)aniline (51)

To a stirred suspension of 1-(3-(3-methoxy-4-nitrophenoxy)propyl)-3-methylpyrrolidine (50) (38 mg, 0.1 mmol) in MeOH (1 mL) was added Pd/C (4 mg, 10%) in one portion at 25° C. The reaction was stirred at 25° C. under $H_2$ atmosphere for 16 h and then filtered through Celite®. The filtered cake was washed with MeOH (5 mL). The combined filtrate was concentrated to afford the titled compound 51 (34 mg, crude) as an oil, which was used for the next step directly without further purification. MS (ESI): $[M+H^+]$=264.9.

Step 4: 3-(2-methoxy-4-(3-(3-methylpyrrolidin-1-yl)propoxy)phenyl)-2-methyl-6-(pentafluorosulfanyl)quinazolin-4(3H)-one (XII)

A solution of 2-amino-5-(pentafluorosulfanyl)benzoic acid (21) (25 mg, 0.1 mmol) in $Ac_2O$ (1 mL) was heated under reflux for 4 h and then concentrated. To the residue were added 2-methoxy-4-(3-(3-methylpyrrolidin-1-yl)propoxy)aniline (51) (34 mg, 0.1 mmol) and AcOH (1 mL) at 25° C. The reaction was stirred at 80° C. for 1 h. After that, the resulting mixture was concentrated. The residue was partitioned between EA (10 mL) and saturated aqueous $NaHCO_3$ solution (5 mL). The aqueous phase was separated. The organic phase was washed with brine (5 mL), dried over anhydrous $Na_2SO_4$, filtered and concentrated. The residue was purified by prep-HPLC to afford the titled compound XII (33 mg in HCl salt, 45%) as a brown solid. $^1$H-NMR (400 MHz, DMSO-$d_6$) δ=11.12 (br. s., 1H), 8.42 (d, J=2.4 Hz, 1H), 8.33 (dd, J=2.2, 9.0 Hz, 1H), 7.85 (d, J=9.2 Hz, 1H), 7.34 (d, J=8.8 Hz, 1H), 6.81 (d, J=1.6 Hz, 1H), 6.71 (dd, J=2.0, 8.8 Hz, 1H), 4.17 (t, J=5.8 Hz, 2H), 3.75 (br. s., 3H), 3.66-3.53 (m, 2H), 3.33-3.07 (m, 4H), 2.66-2.57 (m, 0.5H), 2.37-2.29 (m, 0.5H), 2.25-2.18 (m, 2H), 2.16 (s, 3H), 2.15-2.04 (m, 1H), 1.67-1.47 (m, 1H), 1.07 (dd, J=4.6, 6.2 Hz, 3H); MS (ESI): $[M+H^+]$=534.1.

Example 13

(S)-3-(2-methoxy-4-(3-(2-methylpyrrolidin-1-yl)propoxy)phenyl)-2-methyl-6-(pentafluorosulfanyl)quinazolin-4(3H)-one (XIII

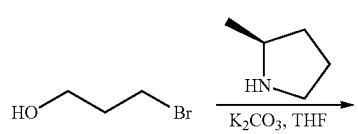

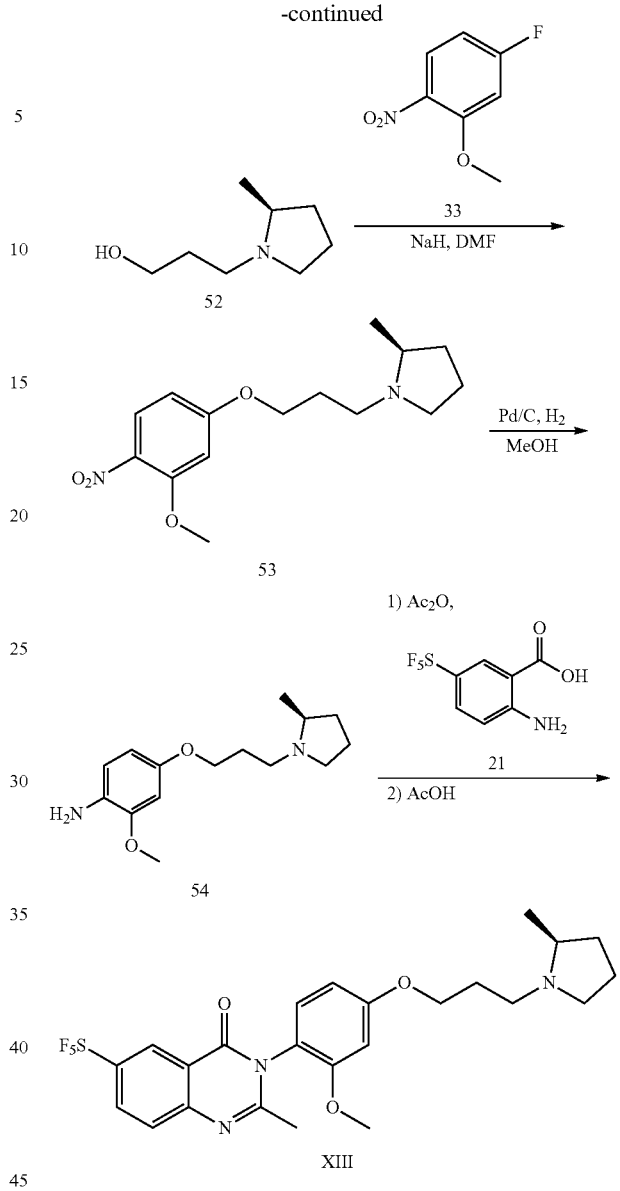

Step 1: (S)-3-(2-methylpyrrolidin-1-yl)propan-1-ol (52)

To a stirred suspension of 3-bromopropan-1-ol (300 mg, 2.2 mmol) in THF (2 mL) were added $K_2CO_3$ (417 mg, 3.0 mmol) and (S)-2-methylpyrrolidine (312 mg, 3.7 mmol) at 0° C. The reaction was stirred at 0° C.-25° C. for 16 h. The resulting mixture was diluted with EA (10 mL) and filtered through Celite®. The filtered cake was washed with EA (10 mL). The combined filtrate was washed with water (5 mL) and brine (5 mL), dried over anhydrous $Na_2SO_4$, filtered and concentrated to afford the titled compound 52 (363 mg, crude) as a colorless oil, which was used for the next step without further purification.

Step 2: (S)-1-(3-(3-methoxy-4-nitrophenoxy)propyl)-2-methylpyrrolidine (53)

To a stirred solution of (S)-3-(2-methylpyrrolidin-1-yl)propan-1-ol (52) (363 mg, crude) in DMF (4 mL) was added NaH (111 mg, 2.8 mmol, 60% in mineral oil) at 0° C. The reaction was stirred at 0° C. for 0.5 h and followed by the addition of 4-fluoro-2-methoxy-1-nitrobenzene (33) (395 mg, 2.3 mmol). The reaction was stirred at 0° C.-25° C. for 16 h. The resulting mixture was diluted with EA (30 mL) and water (5 mL). The organic phase was washed with brine (5 mL), dried over anhydrous Na$_2$SO$_4$, filtered and concentrated. The residue was purified by column chromatography (silica gel, PE/EA=1:1 and DCM/MeOH=10:1) to afford the titled compound 53 (370 mg, 58% for two steps) as a yellow oil. MS (ESI): [M+H$^+$]=294.9.

Step 3: (S)-2-methoxy-4-(3-(2-methylpyrrolidin-1-yl)propoxy)aniline (54)

To a stirred suspension of (S)-1-(3-(3-methoxy-4-nitrophenoxy)propyl)-2-methylpyrrolidine (53) (370 mg, 1.3 mmol) in MeOH (4 mL) was added Pd/C (40 mg, 10%) in one portion at 25° C. The reaction was stirred at 25° C. under H$_2$ atmosphere for 16 h and then filtered through Celite®. The filtered cake was washed with MeOH (5 mL). The combined filtrate was concentrated to afford the titled compound 54 (330 mg, crude) as a black oil, which was used for the next step without further purification. MS (ESI): [M+H$^+$]=264.9.

Step 4: (S)-3-(2-methoxy-4-(3-(2-methylpyrrolidin-1-yl)propoxy)phenyl)-2-methyl-6-(pentafluorosulfanyl)quinazolin-4(3H)-one (XIII)

A solution of 2-amino-5-(pentafluorosulfanyl)benzoic acid (21) (50 mg, 0.2 mmol) in Ac$_2$O (1 mL) was heated to reflux for 4 h and then concentrated. To the residue were added (S)-2-methoxy-4-(3-(2-methylpyrrolidin-1-yl)propoxy)aniline (54) (101 mg, 0.4 mmol) and AcOH (1 mL) at 25° C. The reaction was stirred at 80° C. for 1 h. After that, the resulting mixture was concentrated. The residue was partitioned between EA (10 mL) and saturated aqueous NaHCO$_3$ solution (5 mL). The organic phase was washed with brine (5 mL), dried over anhydrous Na$_2$SO$_4$, filtered and concentrated. The residue was purified by prep-HPLC to afford the titled compound XIII (24 mg in HCl salt, 22%) as a brown solid. $^1$H-NMR (400 MHz, DMSO-d$_6$) δ=10.73 (br. s., 1H), 8.41 (br. s., 1H), 8.33 (d, J=8.0 Hz, 1H), 7.85 (d, J=8.8 Hz, 1H), 7.34 (d, J=8.8 Hz, 1H), 6.82 (br. s., 1H), 6.72 (d, J=8.0 Hz, 1H), 4.19 (br. s., 2H), 3.75 (br. s., 3H), 3.45-3.40 (m, 2H), 3.15-3.02 (m, 2H), 2.36-2.07 (m, 7H), 1.95 (br. s., 2H), 1.73-1.58 (m, 1H), 1.42 (d, J=5.6 Hz, 3H); MS (ESI): [M+H$^+$]=534.1.

Example 14

3-(4-((1-cyclopropylpiperidin-4-yl)oxy)phenyl)-2-methyl-6-(pentafluorosulfanyl) quinazolin-4(3H)-one (XIV)

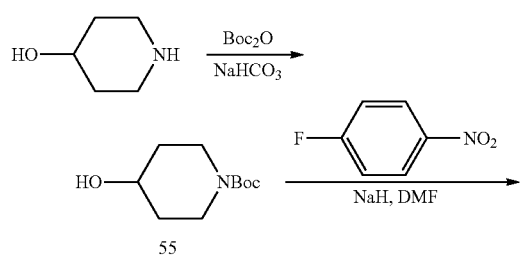

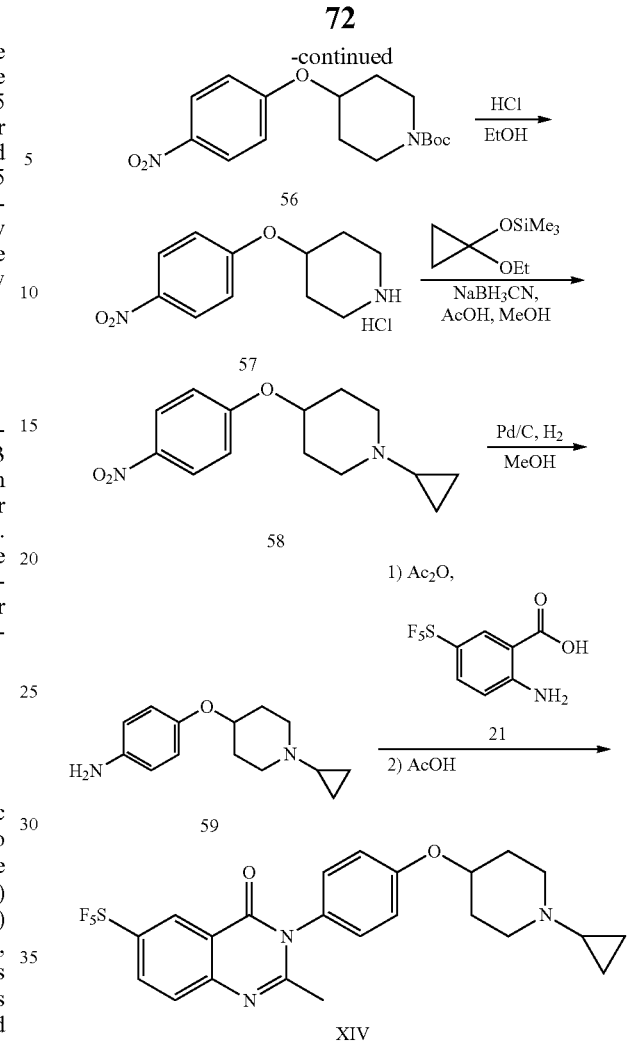

Step 1: tert-butyl 4-hydroxypiperidine-1-carboxylate (55)

To a stirred slurry of piperidin-4-ol (3.0 g, 21.8 mmol) in DCM (30 mL) was added Boc$_2$O (9.5 g, 43.6 mmol). The resulting mixture was stirred for 1 h at 25° C. and then followed by the addition of saturated NaHCO$_3$ (30 mL). The reaction was stirred at 25° C. for 16 h and then separated. The organic phase was washed with brine (30 mL), dried over anhydrous Na$_2$SO$_4$, filtered and concentrated to afford the titled compound 55 (4.0 g, 91%) as a white solid.

Step 2: tert-butyl 4-(4-nitrophenoxy)piperidine-1-carboxylate (56)

To a stirred solution of tert-butyl 4-hydroxypiperidine-1-carboxylate (55) (2.0 g, 9.9 mmol) in DMF (20 mL) was added NaH (0.5 g, 11.9 mmol, 60% in mineral oil) at 0° C. The resulting slurry was stirred for 30 min at 0° C. and followed by the addition of 1-fluoro-4-nitrobenzene (1.7 g, 11.9 mmol). The resulting mixture was stirred at 25° C. for 16 h and then quenched with water (60 mL) and extracted with EA (2×20 mL). The combined organic phase was washed with brine (2×30 mL), dried over anhydrous Na$_2$SO$_4$, filtered and concentrated. The residue was purified by column chromatography (silica gel, PE/EA=20:1-10:1)

to afford the titled compound 56 (2.0 g, 62%) as a pale-yellow solid. $^1$H-NMR (400 MHz, CDCl$_3$) δ=8.20 (d, J=9.2 Hz, 2H), 6.95 (d, J=9.2 Hz, 2H), 4.65-4.53 (m, 1H), 3.78-3.60 (m, 2H), 3.46-3.31 (m, 2H), 2.05-1.89 (m, 2H), 1.88-1.69 (m, 2H), 1.47 (s, 9H).

Step 3: 4-(4-nitrophenoxy)piperidine hydrochloride (57)

To a stirred solution of tert-butyl 4-(4-nitrophenoxy)piperidine-1-carboxylate (56) (2.0 g, 6.2 mmol) in EtOH (10 mL) was added concentrated HCl aqueous solution (10 mL). The resulting mixture was stirred at 25° C. for 4 h and then concentrated to afford the titled compound 57 (1.6 g, 99%) as a yellow solid. MS (ESI): [M+H]$^+$=222.9.

Step 4: 1-cyclopropyl-4-(4-nitrophenoxy)piperidine (58)

To a stirred solution of 4-(4-nitrophenoxy)piperidine hydrochloride (57) (0.5 g, 2.3 mmol) and (1-ethoxycyclopropoxy)trimethylsilane (0.6 g, 3.4 mmol) in AcOH (5 mL) and MeOH (5 mL) was added NaBH$_3$CN (0.3 g, 4.5 mmol). The reaction was heated to 65° C., stirred for 18 h and then concentrated. The residue was dissolved in EA (20 mL) and washed with aqueous NaOH solution (20 mL, 1 M). The organic phase was dried over anhydrous MgSO$_4$, filtered and concentrated to afford the titled compound 58 (0.6 g, crude) as an off-white oil. The crude product was used for next step without further purification. MS (ESI): [M+H]$^+$=262.9.

Step 5: 4-((1-cyclopropylpiperidin-4-yl)oxy)aniline (59)

To a stirred solution of 1-cyclopropyl-4-(4-nitrophenoxy)piperidine (58) (0.3 g, 1.2 mmol) in MeOH was added Pd/C (30 mg, 10%). The reaction was stirred under H$_2$ at 25° C. for 16 h and then filtered. The filtrate was concentrated to afford the titled compound 59 (0.2 g, crude) as an off-white oil. The crude product was used for the next step without further purification. MS (ESI): [M+H]$^+$=232.9.

Step 6: 3-(4-((1-cyclopropylpiperidin-4-yl)oxy)phenyl)-2-methyl-6-(pentafluorosulfanyl)quinazolin-4(3H)-one (XIV)

A solution of 2-amino-5-(pentafluorosulfanyl)benzoic acid (21) (50 mg, 0.2 mmol) in Ac$_2$O (1 mL) was heated under reflux for 2 h and then concentrated. To the residue were added 4-((1-cyclopropylpiperidin-4-yl)oxy)aniline (59) (50 mg, 0.2 mmol) and AcOH (1 mL). The reaction was stirred at 80° C. for 2 h and then concentrated. The residue was purified by prep-HPLC to afford the titled compound XIV (40 mg, 42%) as an off-white solid. $^1$H-NMR (400 MHz, CD$_3$OD) δ=8.64 (s, 1H), 8.46-8.35 (m, 1H), 7.98-7.87 (m, 1H), 7.51-7.36 (m, 2H), 7.35-7.22 (m, 2H), 4.87-4.72 (m, 1H), 3.77 (d, J=12.3 Hz, 1H), 3.64-3.54 (m, 2H), 3.49-3.37 (m, 1H), 3.02-2.88 (m, 1H), 2.54-2.40 (m, 3H), 2.39-2.10 (m, 3H), 2.08-1.87 (m, 1H), 1.22-0.92 (m, 4H); MS (ESI): [M+H]$^+$=502.1.

Example 15

3-(4-((1-cyclobutylpiperidin-4-yl)oxy)phenyl)-2-methyl-6-(pentafluorosulfanyl) quinazolin-4(3H)-one (XV)

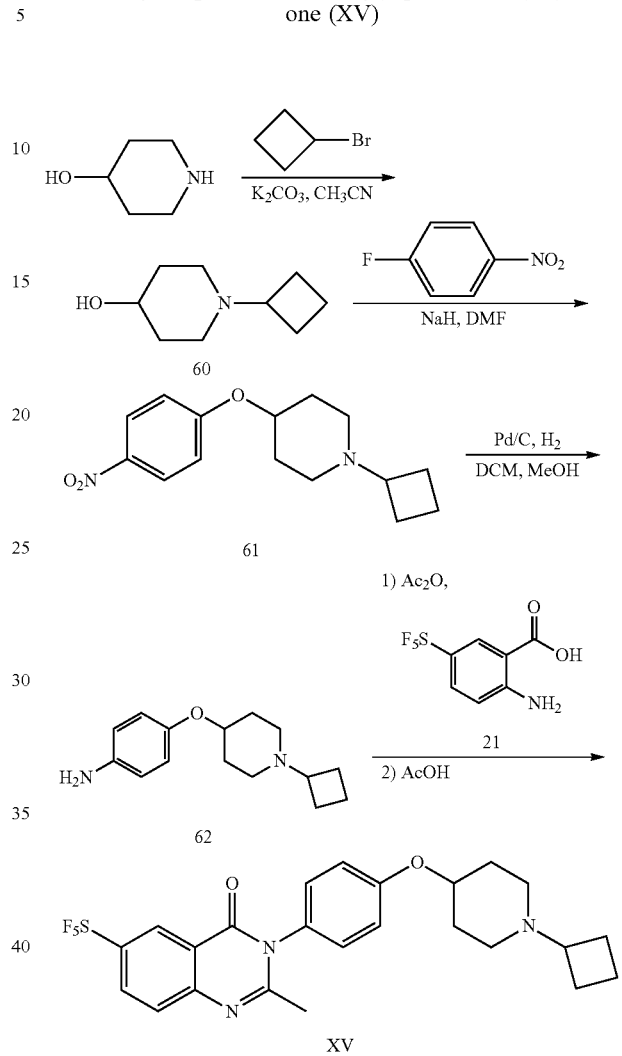

Step 1: 1-cyclobutylpiperidin-4-ol (60)

To a stirred slurry of piperidin-4-ol (1.0 g, 9.9 mmol) and bromocyclobutane (1.6 g, 11.9 mmol) in CH$_3$CN (20 mL) was added K$_2$CO$_3$ (3.4 g, 24.7 mmol). The reaction was heated under reflux for 48 h and then cooled to 25° C. The resulting mixture was filtered and the filter cake was washed with CH$_3$CN (30 mL). The combined filtrate was concentrated to afford the titled compound 60 (1.4 g, crude) as an off-white oil. The crude product was used for the next step without further purification. $^1$H-NMR (400 MHz, CDCl$_3$) δ=3.79-3.61 (m, 1H), 3.09 (d, J=13.8 Hz, 1H), 2.74-2.55 (m, 2H), 2.08-1.82 (m, 6H), 1.79-1.48 (m, 5H), 1.46-1.31 (m, 1H).

Step 2: 1-cyclobutyl-4-(4-nitrophenoxy)piperidine (61)

To a stirred solution of 1-cyclobutylpiperidin-4-ol (60) (1.4 g, 9.0 mmol) in DMF (20 mL) was added NaH (0.7 g, 18.0 mmol, 60% in mineral oil) at 0° C. The resulting mixture was stirred for 30 min at 0° C. and followed by the addition of 1-fluoro-4-nitrobenzene (1.3 g, 9.0 mmol). The resulting mixture was stirred at 25° C. for 16 h and then quenched with water (60 mL) and extracted with EA (2×20 mL). The combined organic phase was washed with brine (2×30 mL), dried over anhydrous $Na_2SO_4$, filtered and concentrated. The residue was purified by column chromatography (silica gel, DCM/MeOH=100:1-20:1) to afford the titled compound 61 (0.8 g, 32%) as a yellow solid. $^1$H-NMR (400 MHz, $CDCl_3$) δ=8.18 (d, J=9.2 Hz, 2H), 6.94 (d, J=9.2 Hz, 2H), 4.46 (d, J=3.2 Hz, 1H), 2.80-2.69 (m, 1H), 2.68-2.51 (m, 2H), 2.27-2.13 (m, 2H), 2.12-1.96 (m, 4H), 1.96-1.78 (m, 4H), 1.77-1.56 (m, 2H); MS(ESI): $[M+H]^+$=276.9.

Step 3: 4-((1-cyclobutylpiperidin-4-yl)oxy)aniline (62)

To a stirred solution of 1-cyclobutyl-4-(4-nitrophenoxy) piperidine (61) (0.7 g, 2.5 mmol) in MeOH (15 mL) was added Pd/C (70 mg, 10%). The reaction was stirred under $H_2$ atmosphere for 16 h at 25° C. and then filtered. The filtrate was concentrated to afford the titled compound 62 (0.6 g, 96%) as a brown solid. $^1$H-NMR (400 MHz, $CDCl_3$) δ=6.75 (d, J=8.8 Hz, 2H), 6.62 (d, J=8.8 Hz, 2H), 4.13 (br. s., 1H), 3.43 (br. s., 2H), 2.78-2.68 (m, 1H), 2.68-2.52 (m, 2H), 2.25-2.09 (m, 2H), 2.06-1.88 (m, 4H), 1.84-1.74 (m, 2H), 1.73-1.57 (m, 2H); MS (ESI): $[M+H]^+$=246.9.

Step 4: 3-(4-((1-cyclobutylpiperidin-4-yl)oxy)phenyl)-2-methyl-6-(pentafluorosulfanyl) quinazolin-4(3H)-one (XV)

A solution of 2-amino-5-(pentafluorosulfanyl)benzoic acid (21) (0.1 g, 0.4 mmol) in $Ac_2O$ (1 mL) was heated under reflux for 2 h and then concentrated. To the residue were added 4-((1-cyclobutylpiperidin-4-yl)oxy)aniline (62) (86 mg, 0.35 mmol) and AcOH (1 mL). The reaction was stirred at 80° C. for 2 h and then concentrated. The residue was purified by prep-HPLC to afford the titled compound XV (90 mg, 50%) as an off-white solid. $^1$H-NMR (400 MHz, $CD_3OD$) δ=8.65 (s, 1H), 8.43 (d, J=8.4 Hz, 1H), 7.94 (d, J=9.2 Hz, 1H), 7.48-7.36 (m, 2H), 7.35-7.21 (m, 2H), 4.82-4.69 (m, 1H), 3.83-3.70 (m, 1H), 3.60 (d, J=12.5 Hz, 1H), 3.41 (d, J=12.1 Hz, 1H), 3.21-3.11 (m, 1H), 3.10-2.93 (m, 1H), 2.50 (s, 3H), 2.45-2.27 (m, 5H), 2.27-2.10 (m, 2H), 2.06-1.73 (m, 3H); MS (ESI): $[M+H]^+$=516.1.

Example 16

3-(4-((1-cyclopentylpiperidin-4-yl)oxy)phenyl)-2-methyl-6-(pentafluorosulfanyl) quinazolin-4(3H)-one (XVI)

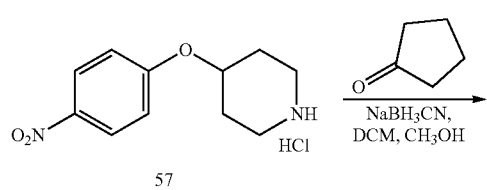

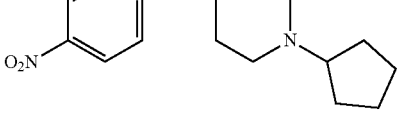

Step 1: 1-cyclopentyl-4-(4-nitrophenoxy)piperidine (63)

To a stirred solution of 4-(4-nitrophenoxy)piperidine hydrochloride (57) (0.2 g, 0.9 mmol) and cyclopentanone (0.1 g, 1.1 mmol) in DCM (2 mL) was added one drop AcOH and then stirred at 25° C. for 1 h. To the reaction were added MeOH (2 mL) and $NaBH_3CN$ (68 mg, 1.1 mmol). The reaction was stirred for 2 h at 25° C. and then quenched with saturated aqueous $NH_4Cl$ solution (5 mL). The resulting mixture was extracted with EA (2×5 mL). The combined organic phase was washed with brine (5 mL), dried over anhydrous $Na_2SO_4$, filtered and concentrated to afford the titled compound 63 (260 mg, crude) as a brown oil. The crude product was used for the next step without further purification. MS (ESI): $[M+H]^+$=290.9.

Step 2: (4-(4-aminophenoxy)piperidin-1-yl)(cyclopentyl)methanone (64)

To a stirred solution of cyclopentyl(4-(4-nitrophenoxy) piperidin-1-yl)methanone (63) (260 mg, 0.9 mmol) in MeOH (3 mL) was added Pd/C (30 mg, 10%). The reaction was stirred under $H_2$ atmosphere at 25° C. for 16 h and then filtered. The filtrate was concentrated to afford the titled compound 64 (230 mg, crude) as an off-white oil. The crude product was used for the next step without further purification. MS (ESI): $[M+H]^+$=260.9.

Step 3: 3-(4-((1-(cyclopentanecarbonyl)piperidin-4-yl)oxy)phenyl)-2-methyl-6-(pentafluorosulfanyl) quinazolin-4(3H)-one (XVI)

A solution of 2-amino-5-(pentafluorosulfanyl)benzoic acid (21) (50 mg, 0.2 mmol) in $Ac_2O$ (1 mL) was heated under reflux for 2 h and then concentrated. To the residue were added (4-(4-aminophenoxy)piperidin-1-yl)(cyclopentyl)methanone (64) (70 mg, 0.2 mmol) and AcOH (1 mL).

The reaction was stirred at 80° C. for 2 h and then concentrated. The residue was purified by prep-HPLC to afford the titled compound XVI (30 mg, 28%) as an off-white solid. $^1$H-NMR (400 MHz, CD$_3$OD) δ=8.60 (d, J=2.4 Hz, 1H), 8.29 (dd, J=2.4, 9.2 Hz, 1H), 7.84 (d, J=9.2 Hz, 1H), 7.42-7.32 (m, 2H), 7.30-7.18 (m, 2H), 3.79-3.70 (m, 1H), 3.69-3.46 (m, 3H), 3.42-3.35 (m, 2H), 3.24-3.12 (m, 1H), 2.53-2.43 (m, 1H), 2.33 (s, 3H), 2.29-2.04 (m, 4H), 2.02-1.82 (m, 3H), 1.79-1.68 (m, 3H); MS (ESI): [M+H]$^+$=530.1.

Example 17

2-methyl-7-(pentafluorosulfanyl)-3-{4-[3-(pyrrolidin-1-yl)-propoxy]phenyl}-3,4-dihydroquinazolin-4-one (XVII)

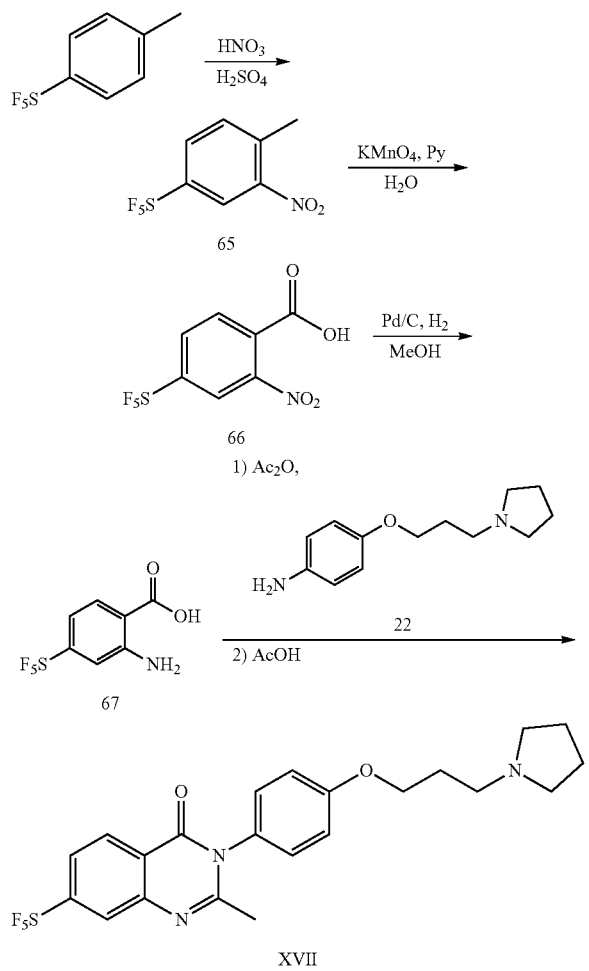

Step 1: 1-methyl-2-nitro-4-(pentafluorosulfanyl)benzene (65)

To a stirred solution of 1-methyl-4-(pentafluorosulfanyl)benzene (500 mg, 2.3 mmol) in H$_2$SO$_4$ (2 mL) was added a mixture of H$_2$SO$_4$ (2 mL) and HNO$_3$ (2 mL) at 0° C. The reaction was stirred at 25° C. for 3 h and then poured into water (20 mL). The resulting mixture was extracted with EA (20 mL). The organic phase was washed with H$_2$O (3×20 mL), dried over anhydrous Na$_2$SO$_4$, filtered and concentrated. The residue phase was purified by column chromatography (silica gel, PE and PE/DCM=–2:1) to afford the titled compound 65 (581 mg, 96%) as a light-yellow oil. $^1$H-NMR (400 MHz, CDCl$_3$) δ=8.39 (s, 1H), 7.89 (d, J=6.0 Hz, 1H), 7.49 (d, J=8.8 Hz, 1H), 2.68 (s, 3H).

Step 2: 1-methyl-2-nitro-4-(pentafluorosulfanyl)benzene (66)

To a stirred solution of 1-methyl-2-nitro-4-(pentafluorosulfanyl)benzene (65) (581 mg, 2.2 mmol) in pyridine (5 mL) and H$_2$O (10 mL) was added KMnO$_4$ (2.1 g, 13.3 mmol). The reaction was stirred at 95° C. for 48 h and then additional KMnO$_4$ (2.1 g, 13.3 mmol) was added. The mixture was stirred at 95° C. for 12 h. The resulting mixture was acidified by aqueous HCl solution (1 M) until pH=1 and extracted with EA (50 mL). The organic phase was washed with brine (3×50 mL) and concentrated. The residue was purified by column chromatography (silica gel, DCM/MeOH=10:1) to afford the titled compound 66 (450 mg, 70%) as a white solid. MS (ESI): [M–H$^+$]=291.9.

Step 3: 2-amino-4-(pentafluorosulfanyl)benzoic acid (67)

To a stirred solution of 1-methyl-2-nitro-4-(pentafluorosulfanyl)benzene (66) (450 mg, 1.54 mmol) in MeOH (15 mL) was added Pd/C (50 mg, 10%). The reaction was stirred at 25° C. under H$_2$ atmosphere for 10 h and then filtered. The filtrate was concentrated to afford the titled compound 67 (350 mg, 86%) as a pale-yellow solid. MS (ESI): [M+H$^+$]=263.8.

Step 4: 2-methyl-3-(4-(3-(pyrrolidin-1-yl)propoxy)phenyl)-7-(pentafluorosulfanyl) quinazolin-4(3H)-one (XVII)

A solution of 2-amino-5-(pentafluorosulfanyl)benzoic acid (21) (200 mg, 0.8 mmol) in Ac$_2$O (2 mL) was heated under reflux for 2 h and then concentrated. To the residue were added 2-amino-4-(pentafluorosulfanyl)benzoic acid (67)(235 mg, 1.07 mmol) and AcOH (2 mL). The mixture was stirred at 80° C. for 1 h and then concentrated. The residue was purified by prep-HPLC to afford the titled compound XVII (330 mg, 63%) as an off-white solid. $^1$H-NMR (400 MHz, CD$_3$OD) δ=8.38 (d, J=8.4 Hz, 1H), 8.11 (s, 1H), 7.99 (d, J=8.4 Hz, 1H), 7.34 (d, J=8.8 Hz, 2H), 7.18 (d, J=8.4 Hz, 2H), 4.22 (t, J=5.8 Hz, 2H), 3.72-3.69 (m, 2H), 3.46 (t, J=5.8 Hz, 2H), 3.17-3.11 (m, 2H), 2.31 (s, 3H), 2.29-2.25 (m, 2H), 2.21-2.15 (m, 2H), 2.06-2.01 (m, 2H); MS (ESI): [M+H$^+$]=490.1.

Example 18

3-(4-((1-(cyclopentanecarbonyl)piperidin-4-yl)oxy)phenyl)-2-methyl-6-(pentafluorosulfanyl)quinazolin-4(3H)-one (XVIII)

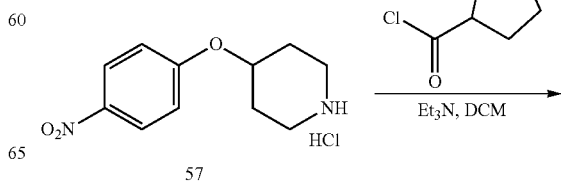

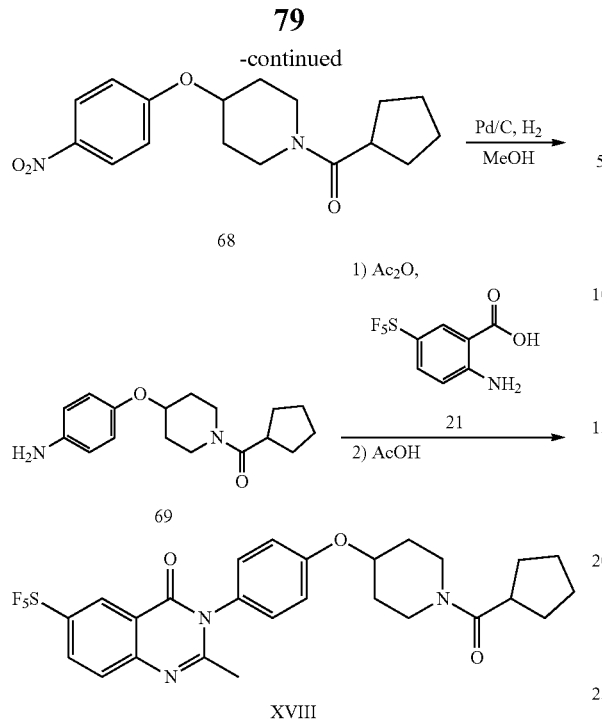

J=2.4 Hz, 1H), 8.24 (dd, J=2.4, 9.2 Hz, 1H), 7.81 (d, J=9.2 Hz, 1H), 7.31 (d, J=8.8 Hz, 2H), 7.19 (d, J=8.8 Hz, 2H), 4.79-4.72 (m, 1H), 4.62 (br. s., 1H), 3.95-3.82 (m, 2H), 3.64-3.53 (m, 2H), 3.16-3.06 (m, 1H), 2.38-2.21 (m, 3H), 2.12-1.97 (m, 2H), 1.91-1.57 (m, 9H); MS(ESI): [M+H]$^+$=558.1.

Example 19

3-(4-((1-(cyclohexanecarbonyl)piperidin-4-yl)oxy)phenyl)-2-methyl-6-(pentafluorosulfanyl)quinazolin-4(3H)-one (XIX)

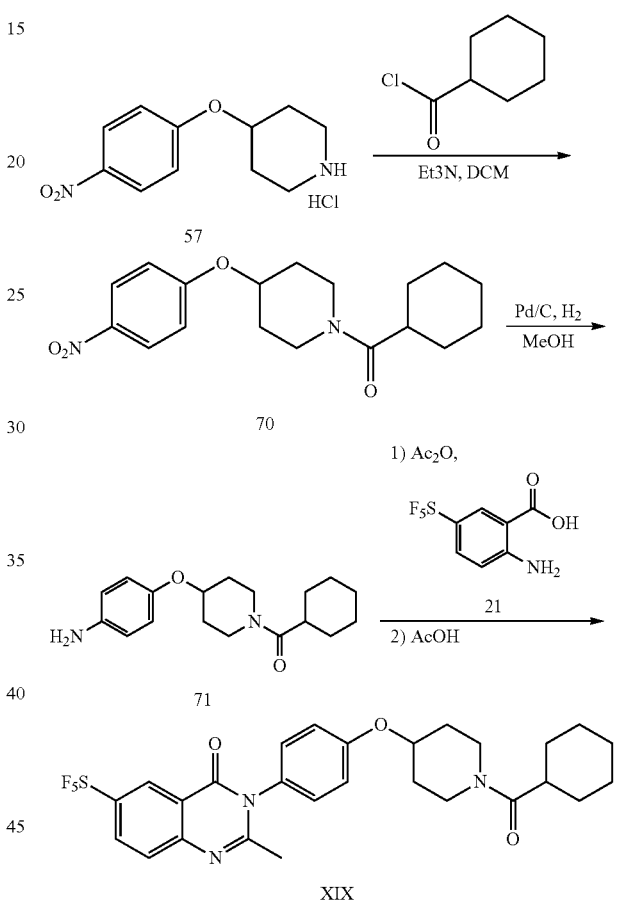

Step 1: cyclopentyl(4-(4-nitrophenoxy)piperidin-1-yl)methanone (68)

To a stirred solution of 4-(4-nitrophenoxy)piperidine hydrochloride (57) (100 mg, 0.39 mmol) were added Et$_3$N (117 mg, 1.2 mmol) and cyclopentanecarbonyl chloride (56 mg, 0.43 mmol) at 0° C. The reaction was stirred for 2 h at 25° C. and then diluted with DCM (4 mL). The resulting mixture was washed with brine (5 mL), dried over anhydrous Na$_2$SO$_4$, filtered and concentrated to afford the titled compound 68 (120 mg, 98%) as a brown oil, which was used for the next step without further purification. MS (ESI): [M+H]$^+$=318.9.

Step 2: (4-(4-aminophenoxy)piperidin-1-yl)(cyclopentyl)methanone (69)

To a stirred solution of cyclopentyl(4-(4-nitrophenoxy)piperidin-1-yl)methanone (68) (120 mg, 0.38 mmol) in MeOH (2 mL) was added Pd/C (10 mg, 10%). The reaction was stirred under H$_2$ atmosphere at 25° C. for 16 h and then filtered. The filtrate was concentrated to afford the titled compound 69 (100 mg, 92%) as a brown oil, which was used for the next without further purification. MS (ESI): [M+H]$^+$=288.9.

Step 3: 3-(4-((1-(cyclopentanecarbonyl)piperidin-4-yl)oxy)phenyl)-2-methyl-6-(pentafluorosulfanyl)quinazolin-4(3H)-one (XVIII)

A solution of 2-amino-5-(pentafluorosulfanyl)benzoic acid (21) (50 mg, 0.2 mmol) in Ac$_2$O (1 mL) was heated to reflux for 2 h and then concentrated to dryness. To the residue were added (4-(4-aminophenoxy)piperidin-1-yl)(cyclopentyl)methanone (69) (70 mg, 0.2 mmol) and AcOH (1 mL). The reaction was stirred at 80° C. for 2 h and then concentrated. The residue was purified by prep-HPLC to afford the titled compound XVIII (30 mg, 28%) as an off-white solid. $^1$H-NMR (400 MHz, CD$_3$OD) δ=8.58 (d, Step 1: cyclohexyl(4-(4-nitrophenoxy)piperidin-1-yl)methanone (70)

To a stirred solution of 4-(4-nitrophenoxy)piperidine hydrochloride (57) (250 mg, 0.9 mmol) and Et$_3$N (117 mg, 1.2 mmol) in DCM (3 mL) was added cyclohexanecarbonyl chloride (170 mg, 1.2 mmol) at 25° C. The reaction was stirred for 16 h at 25° C. and then diluted with DCM (6 mL). The reaction was washed with brine (5 mL), dried over anhydrous Na$_2$SO$_4$, filtered and concentrated to afford the titled compound 70 (300 mg, 93%) as a brown oil. MS (ESI): [M+H]$^+$=332.9.

Step 2: (4-(4-aminophenoxy)piperidin-1-yl)(cyclopentyl)methanone (71)

To a stirred solution of cyclohexyl(4-(4-nitrophenoxy)piperidin-1-yl)methanone (70) (300 mg, 0.9 mmol) in MeOH (6 mL) was added Pd/C (30 mg, 10%). The reaction was stirred under H₂ atmosphere at 25° C. for 16 h and then filtered. The filtrate was concentrated to afford the titled compound 71 (250 mg, 92%) as a brown oil. ¹H-NMR (400 MHz, CD₃OD) δ=6.92 (d, J=8.4 Hz, 2H), 6.79 (d, J=8.8 Hz, 2H), 4.42-4.34 (m, 1H), 3.62-3.50 (m, 2H), 3.48-3.33 (m, 2H), 2.36-2.25 (m, 1H), 1.98-1.86 (m, 4H), 1.57-1.45 (m, 4H), 1.30-1.18 (m, 6H).

Step 3: 3-(4-((1-(cyclohexanecarbonyl)piperidin-4-yl)oxy)phenyl)-2-methyl-6-(pentafluorosulfanyl)quinazolin-4(3H)-one (XIX)

A solution of 2-amino-5-(pentafluorosulfanyl)benzoic acid (21) (50 mg, 0.2 mmol) in Ac₂O (1 mL) was heated under reflux for 2 h and then concentrated. To the residue were added (4-(4-aminophenoxy)piperidin-1-yl)(cyclohexyl)methanone (71) (70 mg, 0.2 mmol) and AcOH (1 mL). The reaction was stirred at 80° C. for 1 h and then concentrated. The residue was purified by prep-HPLC to afford the titled compound XIX (20 mg, 18%) as an off-white solid. ¹H-NMR (400 MHz, CD₃OD) δ=8.66 (s, 1H), 8.12 (d, J=7.6 Hz, 1H), 7.91 (d, J=8.0 Hz, 1H), 7.25-7.13 (m, 2H), 7.13-7.00 (m, 2H), 4.62 (s, 1H), 3.91-3.72 (m, 2H), 3.71-3.59 (m, 1H), 3.57-3.40 (m, 1H), 2.56-2.47 (m, 1H), 2.41 (s, 3H), 2.06-1.94 (m, 2H), 1.93-1.78 (m, 4H), 1.78-1.64 (m, 3H), 1.62-1.47 (m, 2H), 1.38-1.17 (m, 3H); MS (ESI): [M+H]⁺= 572.1.

Example 20

2-methyl-3-(4-((1-(1-methylpiperidine-4-carbonyl)piperidin-4-yl)oxy)phenyl)-6-(pentafluorosulfanyl)quinazolin-4(3H)-one (XX)

Step 1: (1-methylpiperidin-4-yl)(4-(4-nitrophenoxy)piperidin-1-yl)methanone (72)

To a stirred suspension of 4-(4-nitrophenoxy)piperidine hydrochloride (57) (163 mg, 0.6 mmol) in DCM (3 mL) were added Et₃N (254 mg, 2.5 mmol) and 1-methylpiperidine-4-carbonyl chloride (122 mg, 0.8 mmol) in one portion at 0° C. The reaction was stirred at 0° C.-25° C. for 16 h. The mixture was partitioned between DCM (10 mL) and water (5 mL). The organic phase was washed with brine (3 mL), dried over anhydrous Na₂SO₄, filtered and concentrated. The residue was purified by prep-HPLC to afford the titled compound 72 (100 mg, 46%) as a white solid. MS (ESI): [M+H⁺]=347.9.

Step 2: (4-(4-aminophenoxy)piperidin-1-yl)(1-methylpiperidin-4-yl)methanone (73)

To a stirred suspension of (1-methylpiperidin-4-yl)(4-(4-nitrophenoxy)piperidin-1-yl)methanone (72) (100 mg, 0.3 mmol) in MeOH (4 mL) was added Pd/C (10 mg, 10%) in one portion at 25° C. The reaction was stirred at 25° C. under H₂ atmosphere for 16 h and then filtered through Celite®. The filtered cake was washed with MeOH (5 mL). The combined filtrate was concentrated to afford the titled compound 73 (91 mg, crude) as an oil, which was used for the next step without further purification. MS (ESI): [M+H⁺]= 317.9.

Step 4: 2-methyl-3-(4-((1-(1-methylpiperidine-4-carbonyl)piperidin-4-yl)oxy)phenyl)-6-(pentafluorosulfanyl)quinazolin-4(3H)-one (XX)

A solution of 2-amino-5-(pentafluorosulfanyl)benzoic acid (21) (50 mg, 0.2 mmol) in Ac₂O (1 mL) was heated

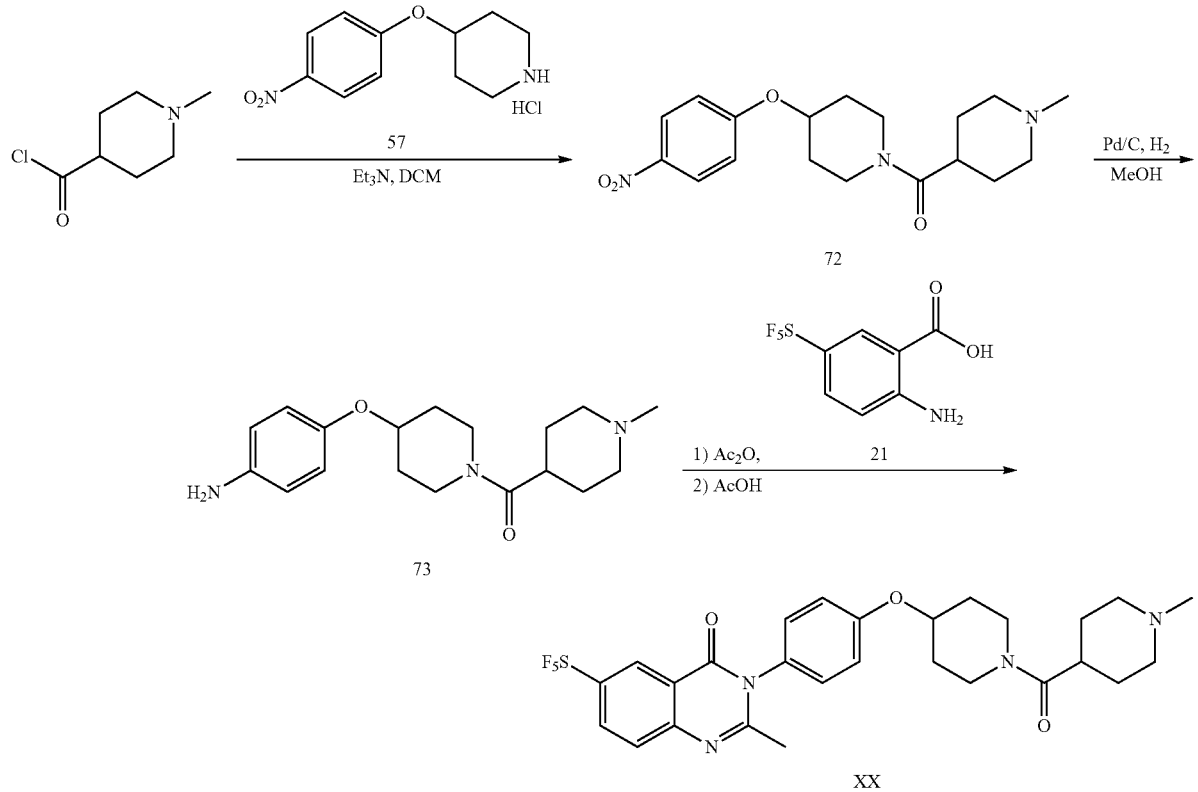

under reflux for 2 h and then concentrated. To the residue were added (4-(4-aminophenoxy)piperidin-1-yl)(1-methylpiperidin-4-yl)methanone (73) (73 mg, 0.2 mmol) and AcOH (1 mL) at 25° C. The reaction was stirred at 80° C. for 1 h. After that, the resulting mixture was concentrated. The residue was partitioned between EA (10 mL) and saturated aqueous NaHCO$_3$ solution (5 mL). The organic phase was washed with brine (5 mL), dried over anhydrous Na$_2$SO$_4$, filtered and concentrated. The residue was purified by prep-HPLC to afford the titled compound XX (37 mg in HCl salt, 26%) as a brown solid. $^1$H-NMR (400 MHz, DMSO-d$_6$) δ=10.42 (br. s., 1H), 8.43 (d, J=2.4 Hz, 1H), 8.34 (dd, J=2.4, 8.8 Hz, 1H), 7.88 (d, J=8.4 Hz, 1H), 7.38 (d, J=8.4 Hz, 2H), 7.17 (d, J=7.2 Hz, 2H), 4.73 (br. s., 1H), 4.00-3.88 (m, 2H), 3.49-3.34 (m, 3H), 3.27-3.12 (m, 2H), 2.98-2.90 (m, 2H), 2.72-2.66 (m, 3H), 2.21 (s, 3H), 2.07-1.79 (m, 6H), 1.66-1.53 (m, 2H); MS (ESI): [M+H$^+$]=587.1.

Example 21

2-methyl-3-(4-((1-(tetrahydro-2H-pyran-4-carbonyl)piperidin-4-yl)oxy)phenyl)-6-(pentafluorosulfanyl)quinazolin-4(3H)-one (XXI)

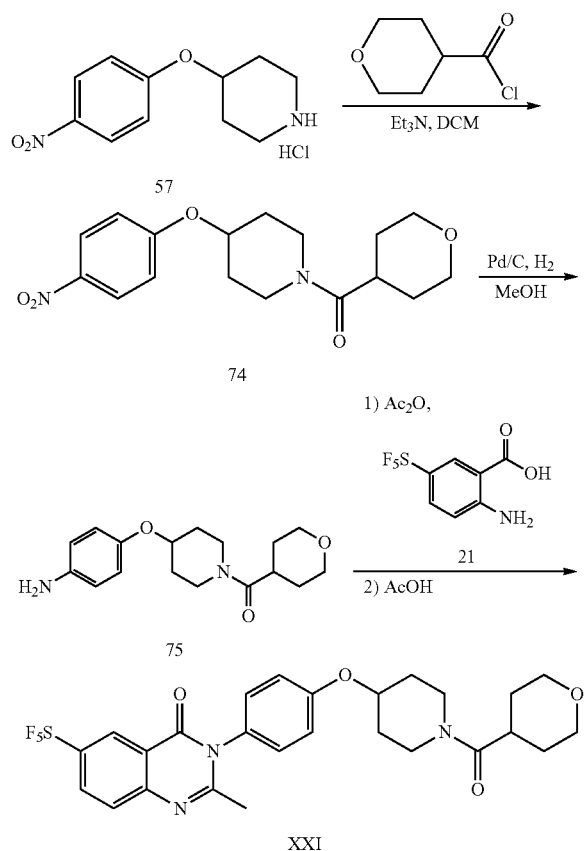

Step 1: (4-(4-nitrophenoxy)piperidin-1-yl)(tetrahydro-2H-pyran-4-yl)methanone (74)

To a solution of 4-(4-nitrophenoxy)piperidine hydrochloride (57) (0.2 g, 0.8 mmol) in Et$_3$N (235.0 mg, 2.3 mmol) was added tetrahydro-2H-pyran-4-carbonyl chloride (126.0 mg, 0.8 mmol) dropwise at 0° C. The reaction was stirred for 30 min and then was allowed to warm up to 25° C., followed by dilution with DCM (4 mL). The resulting mixture was washed with brine (5 mL), dried over anhydrous Na$_2$SO$_4$, filtered and concentrated to afford the titled compound 74 (250 mg, 97%) as a brown oil. MS (ESI): [M+H]$^+$=334.9.

Step 2: (4-(4-aminophenoxy)piperidin-1-yl)(tetrahydro-2H-pyran-4-yl)methanone (75)

To a stirred solution of (4-(4-nitrophenoxy)piperidin-1-yl)(tetrahydro-2H-pyran-4-yl)methanone (74) (250 mg, 0.7 mmol) in MeOH was added Pd/C (25 mg, 10%). The reaction was stirred under H$_2$ atmosphere at 25° C. for 16 h and then filtered. The filtrate was concentrated to afford the titled compound 75 (230 mg, crude) as a brown oil. The crude product was used for the next step without further purification. MS (ESI): [M+H]$^+$=305.0.

Step 3: 2-methyl-3-(4-((1-(tetrahydro-2H-pyran-4-carbonyl)piperidin-4-yl)oxy)phenyl)-6-(pentafluorosulfanyl)quinazolin-4(3H)-one (XXI)

A solution of 2-amino-5-(pentafluorosulfanyl)benzoic acid (21) (50 mg, 0.2 mmol) in Ac$_2$O (1 mL) was heated under reflux for 2 h and then concentrated. To the residue were added (4-(4-aminophenoxy)piperidin-1-yl)(tetrahydro-2H-pyran-4-yl)methanone (75) (70 mg, 0.2 mmol) and AcOH (1 mL). The reaction was stirred at 80° C. for 2 h and then concentrated. The residue was purified by prep-HPLC to afford the titled compound XXI (15 mg, 14%) as an off-white solid. $^1$H-NMR (400 MHz, CD$_3$OD) δ=8.59 (d, J=2.0 Hz, 1H), 8.26 (dd, J=2.0, 9.2 Hz, 1H), 7.82 (d, J=9.2 Hz, 1H), 7.32 (d, J=8.4 Hz, 2H), 7.19 (d, J=8.0 Hz, 2H), 4.76 (d, J=3.2 Hz, 1H), 3.97 (d, J=9.2 Hz, 2H), 3.94-3.79 (m, 2H), 3.66-3.56 (m, 2H), 3.56-3.46 (m, 2H), 3.35 (s, 3H), 3.06-2.97 (m, 1H), 2.17-1.94 (m, 2H), 1.92-1.72 (m, 4H), 1.64 (d, J=12.8 Hz, 2H); MS (ESI): [M+H]$^+$=574.2.

Example 22

3-(2-methoxy-4-((1-(tetrahydro-2H-pyran-4-carbonyl)piperidin-4-yl)oxy)phenyl)-2-methyl-6-(pentafluorosulfanyl)quinazolin-4(3H)-one (XXII)

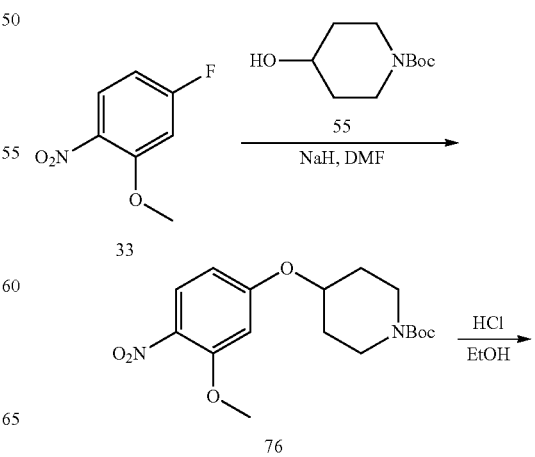

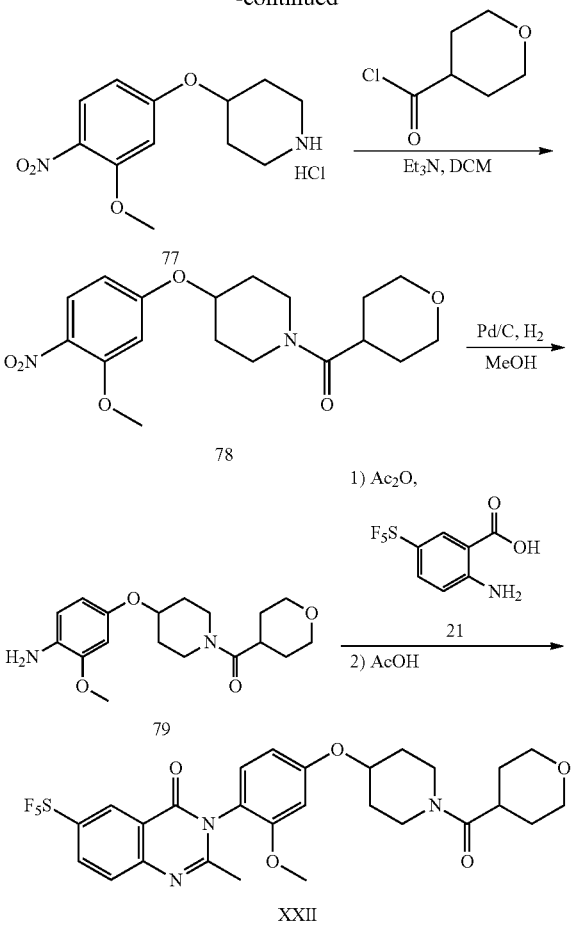

Step 1: tert-butyl 4-(3-methoxy-4-nitrophenoxy)piperidine-1-carboxylate (76)

To a stirred solution of tert-butyl 4-hydroxypiperidine-1-carboxylate (55) (1.4 g, 7.0 mmol) in DMF (10 mL) was added NaH (0.5 g, 11.7 mmol) in portions at 0° C. over 0.5 h, and then followed by the addition of 4-fluoro-2-methoxy-1-nitrobenzene (33) (1.0 g, 5.8 mmol). The reaction was stirred for 16 h at 25° C. The reaction mixture was quenched with saturated aqueous NH₄Cl solution (20 mL) and extracted with EA (2×20 mL). The combined organic phase was washed with brine (2×20 mL), dried over anhydrous Na₂SO₄, filtered and concentrated. The residue was purified by column chromatography (silica gel, PE/EA=100:1-5:1) to afford the titled compound 76 (1.7 g, 83%) as a yellow solid. $^1$H-NMR (400 MHz, CDCl$_3$) δ=8.00 (d, J=8.8 Hz, 1H), 6.54 (s, 1H), 6.50 (d, J=9.2 Hz, 1H), 4.62-4.50 (m, 1H), 3.94 (s, 3H), 3.74-3.63 (m, 2H), 3.44-3.30 (m, 2H), 2.00-1.90 (m, 2H), 1.84-1.72 (m, 2H), 1.47 (s, 9H).

Step 2: 4-(3-methoxy-4-nitrophenoxy)piperidine hydrochloride (77)

To a stirred solution of tert-butyl 4-(3-methoxy-4-nitrophenoxy)piperidine-1-carboxylate (76) (1.7 g, 4.8 mmol) in EtOH (20 mL) was added concentrated aqueous HCl solution (10 mL). The reaction was heated under reflux for 2 h and then concentrated to afford the titled compound 77 (1.3 g, 93%) as a yellow solid. $^1$H-NMR (400 MHz, CD$_3$OD) δ=7.94 (d, J=9.2 Hz, 1H), 6.82 (d, J=2.0 Hz, 1H), 6.71 (dd, J=2.0, 9.2 Hz, 1H), 4.90-4.86 (m, 1H), 3.95 (s, 3H), 3.47-3.37 (m, 2H), 3.30-3.22 (m, 2H), 2.30-2.18 (m, 2H), 2.12-2.00 (m, 2H); MS (ESI): [M+CH$_3$CN+H]$^+$=293.9.

Step 3: (4-(3-methoxy-4-nitrophenoxy)piperidin-1-yl)(tetrahydro-2H-pyran-4-yl)methanone (78)

To a stirred solution of 4-(3-methoxy-4-nitrophenoxy)piperidine hydrochloride (77) (0.4 g, 1.4 mmol) and Et$_3$N (0.4 g, 4.2 mmol) in DCM (5 mL) was added tetrahydro-2H-pyran-4-carbonyl chloride (247 mg, 1.7 mmol) dropwise at 0° C. The reaction was stirred for 1 h at 25° C. and then diluted with EA (15 mL) followed by saturated aqueous NH$_4$Cl solution (10 mL). The organic phase was washed with brine (10 mL), dried over anhydrous Na$_2$SO$_4$, filtered and concentrated to afford the titled compound 78 (0.4 g, 79%) as a yellow oil. MS (ESI): [M+H]$^+$=364.9.

Step 4: (4-(4-amino-3-methoxyphenoxy)piperidin-1-yl)(tetrahydro-2H-pyran-4-yl) methanone (79)

To a stirred solution of (4-(3-methoxy-4-nitrophenoxy)piperidin-1-yl)(tetrahydro-2H-pyran-4-yl)methanone (78) (0.4 g, 1.1 mmol) in MeOH (4 mL) was added Pd/C (40 mg, 10%). The reaction was stirred under H$_2$ atmosphere at 25° C. for 16 h and then filtered. The filtrate was concentrated to afford the titled compound 79 (360 mg, 98%) as an oil. MS (ESI): [M+H]$^+$=334.9.

Step 5: 3-(2-methoxy-4-((1-(tetrahydro-2H-pyran-4-carbonyl)piperidin-4-yl)oxy)phenyl)-2-methyl-6-(pentafluorosulfanyl)quinazolin-4(3H)-one (XXII)

A solution of 2-amino-5-(pentafluorosulfanyl)benzoic acid (21) (50 mg, 0.2 mmol) in Ac$_2$O (1 mL) was heated under reflux for 2 h and then concentrated. To the residue were added (4-(4-amino-3-methoxyphenoxy)piperidin-1-yl)(tetrahydro-2H-pyran-4-yl)methanone (79) (76 mg, 0.2 mmol) and AcOH (1 mL). The reaction was stirred at 80° C. for 1 h and then concentrated. The residue was purified by prep-HPLC to afford the titled compound XXII (20 mg, 17%) as an off-white solid. $^1$H-NMR (400 MHz, CD$_3$OD) δ=8.59 (d, J=2.4 Hz, 1H), 8.31 (dd, J=2.2, 9.0 Hz, 1H), 7.84 (d, J=8.8 Hz, 1H), 7.26 (d, J=8.4 Hz, 1H), 6.85 (s, 1H), 6.79 (d, J=8.8 Hz, 1H), 4.83-4.73 (m, 1H), 4.05-3.93 (m, 2H), 3.93-3.84 (m, 2H), 3.82 (s, 3H), 3.72-3.58 (m, 2H), 3.57-3.45 (m, 2H), 3.07-2.96 (m, 1H), 2.34 (s, 3H), 2.13-1.95 (m, 2H), 1.94-1.70 (m, 4H), 1.69-1.57 (m, 2H); MS (ESI): [M+H]$^+$=604.1.

Example 23

Pharmacological Studies

In the example, the pharmacological properties are described in detail with the compound having formula I-XXII.

Evaluation of Histamine H3 Receptor GTPγS Binding Affinity

Figure 1A:
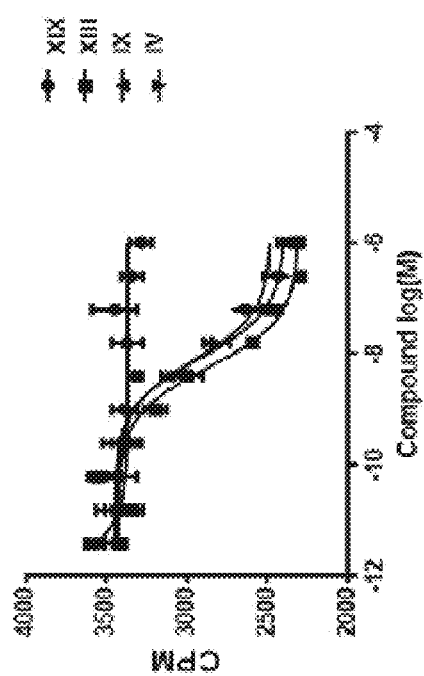
Figure 2B:
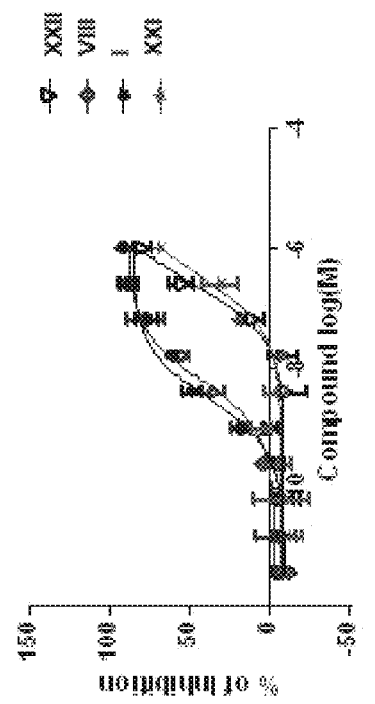
FIG. 2A and FIG. 2B show histamine H3 GTPγS binding curves and % inhibition curves in the antagonist mode for Compounds (I), (VIII), (XXI), and (XXII), respectively.
Figure 2A:
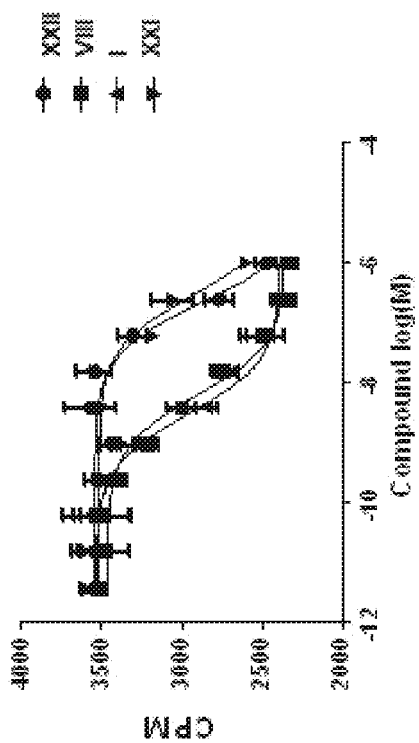
Figure 3B:
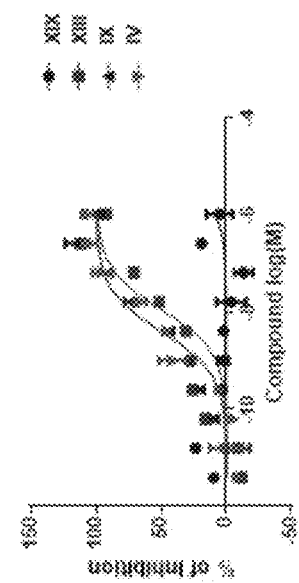
FIG. 3A and FIG. 3B show histamine H3 GTPγS binding curves and % inhibition curves in the antagonist mode for Compounds (IV), (XIII), (IX), and (XIX), respectively.
Figure 3A:
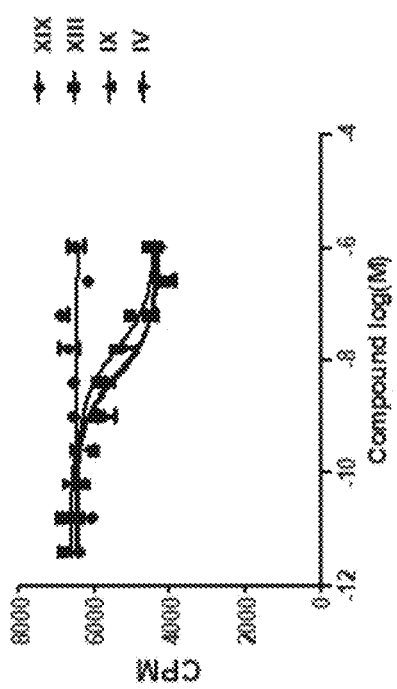
Figures 4A, 4B:
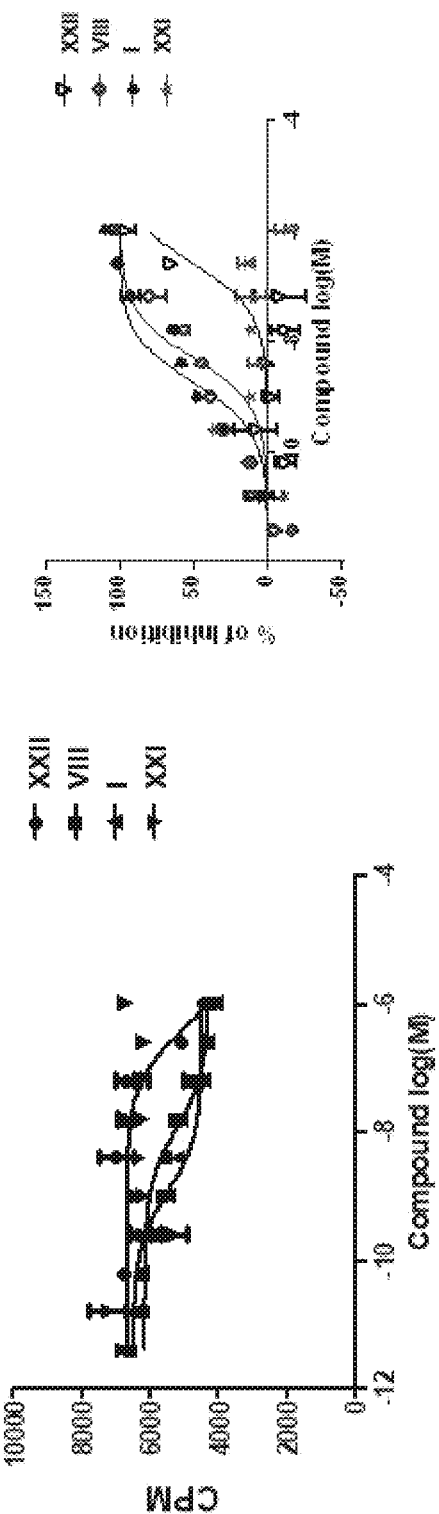
FIG. 4A and FIG. 4B show histamine H3 GTPγS binding curves and % inhibition curves in the antagonist mode for Compounds (I), (VIII), (XXI), and (XXII), respectively.

The histamine H3 receptors mediate the histamine signals in CNS and peripheral nervous system. Histamine H3 receptors couple directly to a Gi/Go, resulting in subsequent GTPγS binding. Although GTPγS binding assays are carried out using membrane preparations in the similar way as radioligand binding assays, these are functional assays and can be used to differentiate agonist, antagonist, and inverse agonist activities. Such assays are carried out using [$^{35}$S]-guanosine-5'-O-(3-thio)triphosphate which provides a radio-active ligand with high affinity for G-protein a subunits that is highly resistant to the inherent GTPase activity of a subunits, such that it remains bound for sufficient periods of time to allow counting of radioactivity. The GTPγS binding assay was performed using HEK293/Ga15/hH3R cell line with high histamine H3 receptors expression to determine H3 receptor GTPγS binding affinity of representative compounds. The results of inverse agonist and antagonist activities are shown in the Table 1, while the H3R GTPγS binding affinity and % inhibition curves for representative compounds are shown in FIGS. 1A, 1B, 2A and 2B; and FIGS. 3A, 3B, 4A, and 4B for inverse agonist mode and antagonist mode, respectively.

1. [$^{35}$S]-GTPγS binding assay for determining antagonist and inverse agonist pharmacological parameters of histamine H3 receptor ligands:

Materials: GTPγS, [35S] (PerkinElmer, Cat #NEG030H001MC), DMSO (Amresco, Cat #0231), MicroScint™-20 (PerkinElmer, Cat #6013621), CelLytic™ M Cell Lysis Reagent (Sigma, Cat #C2978-250ML), (R)(−)-α-Methylhistamine (Sigma, Cat #H128), GDP (Sigma, Cat #G7127), GF/C plate (PE, CAT #6005174).

Experimental procedure: 1) Membrane preparation for HEK293/Ga15/hH3R; 2) Standard binding assay. Briefly, for membrane parathion, HEK293/Ga15/hH3R cells were grown to confluence, harvested and the cell pellets were suspended in TEL buffer (50 mM Tris-HCl buffer, 1 mM EGTA, 0.1 mM PMSF). Homogenate and centrifuge at 1,000 g for 10 min. Centrifuge the supernatant at 46,000 g for 30 min. Suspend the membrane pellet in 50 mM Tris with 0.32 M sucrose, pH 7.0. Aliquot at 1 mg protein/mL. Keep frozen and store at −80° C. until use. All compounds were prepared by dissolving in DMSO to make 10 mM stock. The 10 mM stock was used as top concentration (1 μM) to carry out 10-points, 3-fold dilution scheme using DMSO in a 96-well plate to make the compound dose plate. H3R GTPγS binding assay was performed as followings: thaw the membrane at 37° C., chill on ice, add GDP and the membrane to assay buffer (50 mM Tris-HCl, 100 mM NaCl, 5 mM MgCl$_2$, pH 7.4, and 0.2%, BSA). Stay on ice for 20 min. For inverse agonist mode: Add 20 μL testing compound (10 points, 3-fold dilution from 1 μM), 20 uL buffer, 140 μL membrane solution (GDP 10 μM, membrane protein 20 μg/well) to the assay plate, and preincubate at room temperature for 30 min. Add 20 μL [$^{35}$S]-GTPγS (final 200 pM) and incubate at room temperature for 60 min. For antagonist mode: Add 20 μL agonist (R-alpha-methylhistamine, final concentration 1 μM), 20 μL testing compound (final top concentration 1 μM, 3-fold dilution, 10 points), 20 μL [$^{35}$S]-GTPγS (final 200 pM), 140 μL membrane solution (total 200 μL, GDP 10 μM, membrane protein 20 μg/well) to the assay plate. Incubate at room temperature for 60 min. Filter the assay plate on GF/C (non-PEI coated) plate to stop the assay. Dry GF/C plate for 1 h. Add 50 μL scintillation fluid and count on the MicroBeta.

Data Analysis: The CPM values were calculated into % of inhibition with the following formula:

For inverse agonist mode: % of inhibition=(DMSO control CPM−Compound CPM)/(DMSO control CPM−GTP control CPM)×100.

For antagonist mode: % of inhibition=(R-alpha-methyl-histamine control CPM−Compound CPM)/(R-alpha-methyl-histamine control CPM−DMSO control CPM)×100.

IC$_{50}$s were calculated using Prism5 with log(inhibitor) vs. response equation.

Experimental results are provided in Table 1.

TABLE 1

Data summary of IC$_{50}$s in HEK293/Ga15/hH3RGTPγS assay of representative compounds.

| Compound | Inverse Agonist Mode IC$_{50}$ (nM) | Antagonist Mode IC$_{50}$ (nM) |
|---|---|---|
| I | 3.051 | 1.73 |
| II | 3.181 | 3.63 |
| III | 39.61 | 21.23 |
| IV | 8.153 | 3.866 |
| V | 36.49 | 20.0 |
| VI | 5.50 | 5.36 |
| VII | 10.48 | 3.437 |
| VIII | 6.114 | 4.81 |
| IX | 7.699 | 3.828 |
| X | 9.096 | 52.48 |
| XII | 4.975 | 17.64 |
| XIII | 5.628 | 10.88 |
| XIV | 55.73 | 61.86 |
| XVI | 174.6 | 115.6 |
| XIX | >1000 | >1000 |
| XX | 50.49 | 814.1 |
| XXI | 286.5 | >1000 |
| XXII | 229.3 | 242.3 |

Finally, it should be noted that there are other ways to practice the invention. Accordingly, embodiments of the present invention are to be described as examples, but the present invention is not limited to the contents described, further modifications may be made within the scope of the present invention or the equivalents added in the claims.

All publications or patents cited herein are incorporated by reference in this invention.

Reference throughout this specification to "an embodiment", "some embodiments", "one embodiment", "another example", "an example", "a specific example" or "some examples" means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example, "in an example," "in a specific example," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A method of treating narcolepsy associated with a viral infection in a patient comprising administering to a patient in need of such treatment a therapeutically effective amount of a compound having the structure:

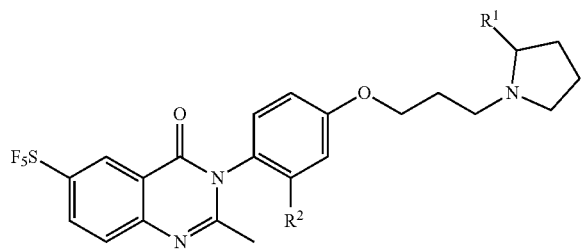

or a pharmaceutically acceptable salt thereof, wherein,
R¹ is selected from hydrogen and $C_{1-3}$ alkyl; and
R² is selected from hydrogen, hydroxyl, and $C_{1-3}$ alkoxy.

2. The method of claim 1, wherein,
R¹ is selected from hydrogen and methyl; and
R² is selected from hydrogen, hydroxyl, and methoxy.

3. The method of claim 1, wherein the compound is 2-methyl-3-(4-(3-(pyrrolidin-1-yl)propoxy)phenyl)-6-(pentafluorosulfanyl) quinazolin-4(3H)-one (I) or a pharmaceutically acceptable salt thereof:

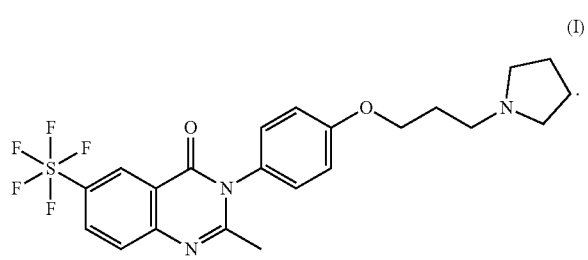 [SMILES: Cc1nc2ccc(S(F)(F)(F)(F)F)cc2c(=O)n1-c1ccc(OCCCN2CCCC2)cc1]

(I)

4. The method of claim 1, wherein the compound is selected from:

(S)-2-methyl-3-(4-(3-(2-methylpyrrolidin-1-yl)propoxy)phenyl)-6-(pentafluorosulfanyl)quinazolin-4(3H)-one (II);

(R)-2-methyl-3-(4-(3-(2-methylpyrrolidin-1-yl)propoxy)phenyl)-6-(pentafluorosulfanyl)quinazolin-4(3H)-one (IV);

3-(2-methoxy-4-(3-(pyrrolidin-1-yl)propoxy)phenyl)-2-methyl-6-(pentafluorosulfanyl)quinazolin-4(3H)-one (VI);

3-(2-hydroxy-4-(3-(pyrrolidin-1-yl)propoxy)phenyl)-2-methyl-6-(pentafluoro-16-sulfaneyl)quinazolin-4(3H)-one (VIII);

(R)-3-(2-methoxy-4-(3-(2-methylpyrrolidin-1-yl)propoxy)phenyl)-2-methyl-6-(pentafluorosulfanyl)quinazolin-4(3H)-one (X); and (S)-3-(2-methoxy-4-(3-(2-methylpyrrolidin-1-yl)propoxy)phenyl)-2-methyl-6-(pentafluorosulfanyl)quinazolin-4(3H)-one (XIII);

or a pharmaceutically acceptable salt of any of the foregoing.

5. The method of claim 1, wherein administering comprises administering a pharmaceutical composition comprising the compound having the structure:

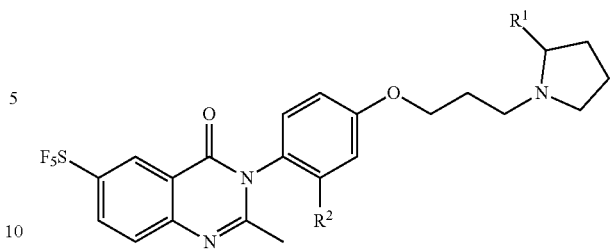

or a pharmaceutically acceptable salt thereof, wherein,
R¹ is selected from hydrogen and $C_{1-3}$ alkyl; and
R² is selected from hydrogen, hydroxyl, and $C_{1-3}$ alkoxy.

6. A method of enhancing cognitive function associated with a central nervous system disease in a patient comprising administering to a patient in need of such treatment thereof a therapeutically effective amount of a compound having the structure:

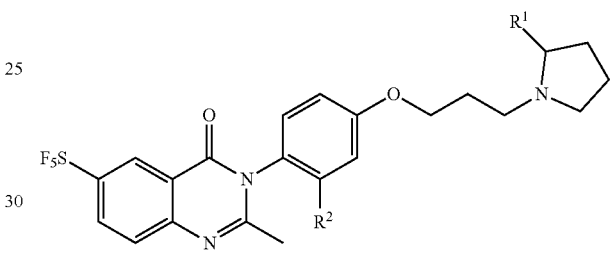

or a pharmaceutically acceptable salt thereof, wherein,
R¹ is selected from hydrogen and $C_{1-3}$ alkyl; and
R² is selected from hydrogen, hydroxyl, and $C_{1-3}$ alkoxy.

7. The method of claim 6, wherein,
R¹ is selected from hydrogen and methyl; and
R² is selected from hydrogen, hydroxyl, and methoxy.

8. The method of claim 6, wherein the compound is 2-methyl-3-(4-(3-(pyrrolidin-1-yl)propoxy)phenyl)-6-(pentafluorosulfanyl) quinazolin-4(3H)-one (I) or a pharmaceutically acceptable salt thereof:

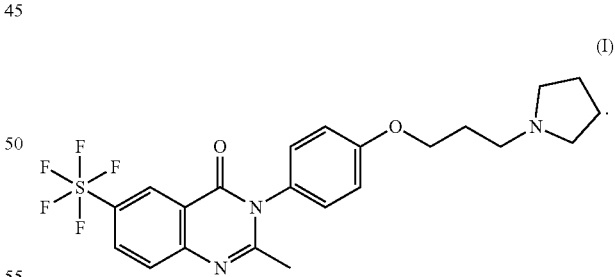

(I)

9. The method of claim 6, wherein the compound is selected from:

(S)-2-methyl-3-(4-(3-(2-methylpyrrolidin-1-yl)propoxy)phenyl)-6-(pentafluorosulfanyl)quinazolin-4(3H)-one (II);

(R)-2-methyl-3-(4-(3-(2-methylpyrrolidin-1-yl)propoxy)phenyl)-6-(pentafluorosulfanyl)quinazolin-4(3H)-one (IV);

3-(2-methoxy-4-(3-(pyrrolidin-1-yl)propoxy)phenyl)-2-methyl-6-(pentafluorosulfanyl)quinazolin-4(3H)-one (VI);

3-(2-hydroxy-4-(3-(pyrrolidin-1-yl)propoxy)phenyl)-2-methyl-6-(pentafluoro-16-sulfaneyl)quinazolin-4(3H)-one (VIII);

(R)-3-(2-methoxy-4-(3-(2-methylpyrrolidin-1-yl)propoxy)phenyl)-2-methyl-6-(pentafluorosulfanyl)quinazolin-4(3H)-one (X); and (S)-3-(2-methoxy-4-(3-(2-methylpyrrolidin-1-yl)propoxy)phenyl)-2-methyl-6-(pentafluorosulfanyl)quinazolin-4(3H)-one (XIII);

or a pharmaceutically acceptable salt of any of the foregoing.

10. The method of claim 6, wherein administering comprises administering a therapeutically effective amount of a pharmaceutical composition comprising the compound having the structure:

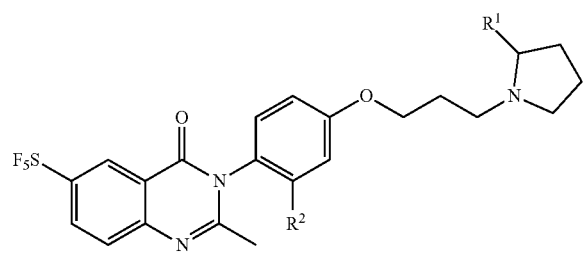

or a pharmaceutically acceptable salt thereof, wherein,
$R^1$ is selected from hydrogen and $C_{1-3}$ alkyl; and
$R^2$ is selected from hydrogen, hydroxyl, and $C_{1-3}$ alkoxy.

11. A method of treating narcolepsy associated with a viral infection in a patient comprising administering to a patient in need of such treatment a therapeutically effective amount of a compound selected from:

2-methyl-3-(4-3-(3-methylpyrrolidin-1-yl)propoxy)phenyl)-6-(pentafluorosulfanyl)quinazolin-4(3H)-one (VII);

3-(2-methoxy-4-(3-(3-methylpyrrolidin-1-yl)propoxy)phenyl)-2-methyl-6-(pentafluorosulfanyl)quinazolin-4(3H)-one (XII); and a pharmaceutically acceptable salt of any of the foregoing.

12. The method of claim 11, wherein administering comprises administering a therapeutically effective amount of a pharmaceutical composition comprising the compound.

13. A method of enhancing cognitive function associated with a central nervous system disease in a patient comprising administering to a patient in need of such treatment thereof a therapeutically effective amount of a compound selected from:

2-methyl-3-(4-3-(3-methylpyrrolidin-1-yl)propoxy)phenyl)-6-(pentafluorosulfanyl)quinazolin-4(3H)-one (VII);

3-(2-methoxy-4-(3-(3-methylpyrrolidin-1-yl)propoxy)phenyl)-2-methyl-6-(pentafluorosulfanyl)quinazolin-4(3H)-one (XII); and a pharmaceutically acceptable salt of any of the foregoing.

14. The method of claim 13, wherein administering comprises administering a therapeutically effective amount of a pharmaceutical composition comprising the compound.

* * * * *